United States Patent
Shen et al.

(10) Patent No.: US 11,312,726 B2
(45) Date of Patent: Apr. 26, 2022

(54) THIENODIAZEPINE DERIVATIVES AND APPLICATION THEREOF

(71) Applicant: CSPC ZHONGQI PHARMACEUTICAL TECHNOLOGY (SHIJIAZHUANG) CO., LTD., Hebei (CN)

(72) Inventors: Chunli Shen, Shanghai (CN); Chengde Wu, Shanghai (CN); Yong Liu, Shanghai (CN); Zhen Gong, Shanghai (CN); Jian Li, Shanghai (CN); Shuhui Chen, Shanghai (CN)

(73) Assignee: CSPC ZHONGQI PHARMACEUTICAL TECHNOLOGY (SHIJIAZHUANG) CO., LTD., Hebei (CN)

( * ) Notice: Subject to any disclaimer, the term of this patent is extended or adjusted under 35 U.S.C. 154(b) by 0 days.

(21) Appl. No.: 16/649,964

(22) PCT Filed: Sep. 6, 2018

(86) PCT No.: PCT/CN2018/104345
§ 371 (c)(1),
(2) Date: Mar. 23, 2020

(87) PCT Pub. No.: WO2019/056950
PCT Pub. Date: Mar. 28, 2019

(65) Prior Publication Data
US 2021/0017190 A1    Jan. 21, 2021

(30) Foreign Application Priority Data
Sep. 22, 2017   (CN) .......................... 201710867197.2

(51) Int. Cl.
| C07D 495/14 | (2006.01) |
| C07D 519/00 | (2006.01) |
| C07D 243/06 | (2006.01) |
| A61P 35/04  | (2006.01) |
| A61P 35/00  | (2006.01) |
| A61K 31/55  | (2006.01) |

(Continued)

(52) U.S. Cl.
CPC ............ C07D 495/14 (2013.01); A61P 35/04 (2018.01); C07D 519/00 (2013.01)

(58) Field of Classification Search
CPC .. C07D 495/14; C07D 519/00; C07D 243/06; A61P 35/04; A61P 35/00; A61P 43/00; A61K 31/55; A61K 45/00; A61K 31/551
See application file for complete search history.

(56) References Cited

U.S. PATENT DOCUMENTS 5,712,274 A    1/1998    Sueoka et al.
2010/0286127 A1    11/2010    Miyoshi et al.

FOREIGN PATENT DOCUMENTS

| CN | 101910182 | 7/2013 |
| EP | 2239264   | 10/2010 |

(Continued)

OTHER PUBLICATIONS

Legal Definition of Medical Treatment; Law Insider (https://www.lawinsider.com/dictionary/medical-treatment 2020; p. 1-9.*

(Continued)

*Primary Examiner* — John M Mauro
(74) *Attorney, Agent, or Firm* — Kilpatrick Townsend & Stockton LLP

(57) ABSTRACT

The present invention relates to a class of thienodiazepine derivatives and an application thereof in the preparation of a drug for the treatment of diseases associated with bromodomain and extra-terminal (BET) Bromodomain inhibitors. Specifically, the present invention relates to compounds represented by formulas (I) and (II), as well as pharmaceutically acceptable salts thereof.

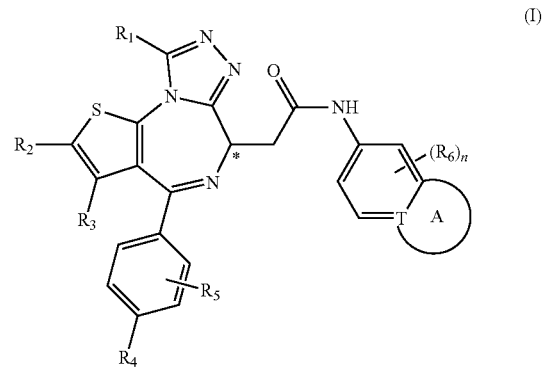

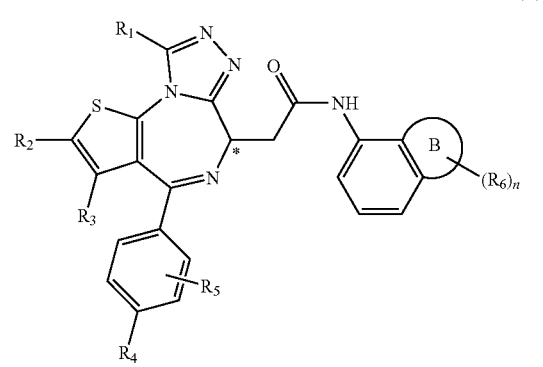

21 Claims, No Drawings

(51) Int. Cl.
*A61K 31/551* (2006.01)
*A61K 45/00* (2006.01)
*A61P 43/00* (2006.01)

(56) References Cited

FOREIGN PATENT DOCUMENTS

| WO | 2013030150 | 3/2013 |
|---|---|---|
| WO | 2015-018520 A1 | 2/2015 |
| WO | 2015018520 | 2/2015 |
| WO | 2017044792 | 3/2017 |
| WO | 2017044849 | 3/2017 |
| WO | 2017044849 | 9/2017 |
| WO | 2017044792 | 4/2018 |

OTHER PUBLICATIONS

Garnier, J-M., "BET bromodomain inhibitors: a patent review." Expert opinion on therapeutic patents 24.2 (2014): 185-199.*
Alqahtani, A., "Bromodomain and extra-terminal motif inhibitors: a review of preclinical and clinical advances in cancer therapy." Future science OA 5.3 (2019): FS0372.*
International Application No. PCT/CN2018/104345, International Preliminary Report on Patentability dated Apr. 2, 2020, 14 pages (5 pages of Original Document and 9 pages of English Translation).
International Application No. PCT/CN2018/104345, International Search Report and Written Opinion dated Nov. 26, 2018, 16 pages (8 pages of Original Document and 8 pages of English Translation).
Guo, et al. "Tetrandrine-induced autophagy in MDA-MB-231 triple-negative breast cancer cell through the inhibition of PI3K/AKT/mTOR signaling." Evidence-Based Complementary and Alternative Medicine 2019 (2019).
Hero, et al. "The triple-negative breast cancer cell line MDA-MB 231 is specifically inhibited by the ionophore salinomycin." Anti-cancer research 39.6 (2019): 2821-2827.
Jiang, et al. "cGAMP inhibits tumor growth in colorectal cancer metastasis through the STING/STAT3 axis in a zebrafish xenograft model." Fish & shellfish immunology 95 (2019): 220-226.
Jones, et al. "Radiation combined with macrophage depletion promotes adaptive immunity and potentiates checkpoint blockade." EMBO molecular medicine 10.12 (2018): e9342.
Lee, et al. "Differential effects of luteolin and its glycosides on invasion and apoptosis in MDA-MB-231 triple-negative breast cancer cells." EXCLI journal 18 (2019): 750.
European Application No. 18859140.8, Extended European Search Report dated Apr. 15, 2021, 10 pages.

* cited by examiner

THIENODIAZEPINE DERIVATIVES AND APPLICATION THEREOF

CROSS-REFERENCES TO RELATED APPLICATIONS

This application is a national phase entry under 35 USC § 371 of International Application PCT/CN2018/104345 filed Sep. 6, 2018, and entitled "THIENODIAZEPINE DERIVATIVES AND APPLICATION THEREOF", which claims priority to and benefits of Chinese Patent Application No. 201710867197.2 filed on Sep. 22, 2017, the disclosures of which are hereby incorporated in their entireties by this reference.

TECHNICAL FIELD

The present invention relates to a class of thienodiazepine derivatives and an application thereof in the preparation of a drug for the treatment of diseases associated with BET Bromodomain inhibitors. Specifically, the present invention relates to compounds represented by formulae (I) and (II), as well as pharmaceutically acceptable salts thereof.

BACKGROUND

The recognition of histone lysine acetylation is a key step in the epigenetic regulation taken part in by the histone acetylation. Acetylated histone lysine can be specifically recognized by the bromodomains (BRDs) domain, thereby recruiting chromatin regulatory factors to specific regions, and coordinating the gene expression regulation. The BRD domain acting on the bromodomain and extra-terminal (BET) protein family can regulate the expression of key oncogenes c-MYC and anti-apoptotic proteins. The study of specific inhibitors targeting BET bromodomain proteins has become a hotspot in the research of anticancer and anti-inflammatory drugs targeting epigenetic regulatory mechanisms. The BET bromodomain family includes four proteins with tandem Bromo domains: BRD2, BRD3, BRD4, and BRDT.

SUMMARY OF THE INVENTION

The present invention provides a compound represented by formula (I) or (II), an isomer thereof or a pharmaceutically acceptable salt thereof,

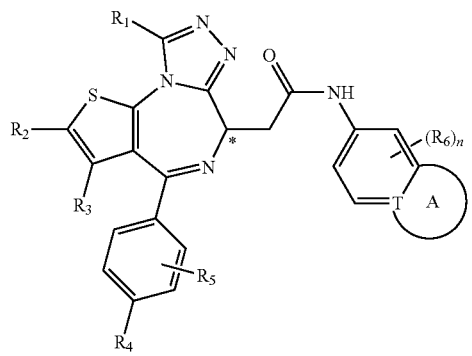

(I)

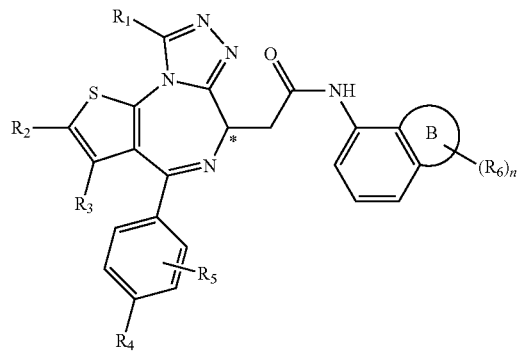

(II)

wherein,

T is selected from a group consisting of CH and N;

$R_1$ is selected from a group consisting of $C_{1-3}$alkyl and $C_{1-3}$alkoxyl, both of which are optionally substituted by 1, 2 or 3 R group(s);

$R_2$, $R_3$, and $R_4$ are separately and independently selected from a group consisting of H, F, Cl, Br, I, OH, $NH_2$ and CN, or separately and independently selected from a group consisting of $C_{1-6}$ alkyl and $C_{1-6}$heteroalkyl, both of which are optionally substituted by 1, 2 or 3 R group(s);

$R_5$ is H, or $C_{1-3}$alkyl that is optionally substituted by 1, 2 or 3 R group(s);

$R_6$ is separately and independently selected from a group consisting of H, F, Cl, Br, I, OH, $NH_2$ and CN, or separately and independently selected from a group consisting of $C_{1-6}$ alkyl and $C_{1-6}$heteroalkyl, both of which are optionally substituted by 1, 2 or 3 R group(s); or two $R_6$ groups attached to the same carbon atom form —C(=O) together with the carbon atom attached thereto;

ring A is selected from a group consisting of $C_{3-7}$ cycloalkyl, 5-12 membered heterocycloalkyl and 5-6 membered heteroaryl;

ring B is selected from a group consisting of 4-7 membered heterocycloalkyl;

and the structural unit

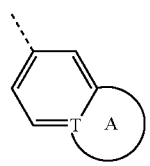

is not selected from a group consisting of

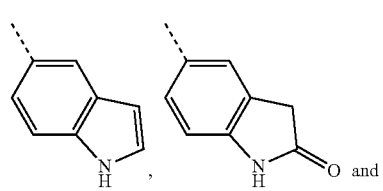

and

-continued

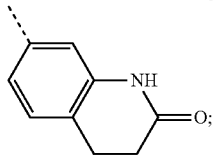

n is selected from a group consisting of 0, 1, 2, 3, 4, 5 and 6;

R is separately and independently selected from a group consisting of F, Cl, Br, I, OH, $NH_2$ and CN, or selected from a group consisting of $C_{1-6}$ alkyl and $C_{1-6}$heteroalkyl, both of which are optionally substituted by 1, 2 or 3 R' group(s);

R' is separately and independently selected from a group consisting of F, Cl, Br, I, OH, $NH_2$, CN and Me;

the carbon atom marked with "*" is a chiral carbon atom, which is present in the form of a single (R) or (S) enantiomer, or in the form of being enriched in one of two enantiomers;

the term "hetero" in the $C_{1-6}$heteroalkyl, the 5-12 membered heterocycloalkyl, the 5-6 membered heteroaryl, and the 4-7 membered heterocycloalkyl is selected from a group consisting of N, —O—, —S—, —NH—, —C(=O)NH—, —C(=O)—, —C(=O)O—, —S(=O)$_2$—, —S(=O)—, and —C(=O)S—;

the number of the above heteroatom or heteroatom group is separately and independently selected from a group consisting of 1, 2, 3 and 4.

In some embodiments of the present invention, the above-mentioned R is selected from a group consisting of F, Cl, Br, I, OH, $NH_2$, and CN, or selected from a group consisting of $C_{1-3}$alkyl and $C_{1-3}$alkoxy, both of which are optionally substituted by 1, 2 or 3 R' group(s), and other variables are as defined in the present invention.

In some embodiments of the present invention, the above-mentioned R is selected from a group consisting of F, Cl, Br, I, OH, $NH_2$, and CN, or selected from a group consisting of Me, Et, and

all of which are optionally substituted by 1, 2 or 3 R' group(s), and other variables are as defined in the present invention.

In some embodiments of the present invention, the above-mentioned R is selected from a group consisting of F, Cl, Br, I, OH, $NH_2$, CN, Me, $CF_3$, Et, and

and other variables are as defined in the present invention.

In some embodiments of the present invention, the above-mentioned $R_1$ is selected from a group consisting of Me, Et, and

all of which are optionally substituted by 1, 2 or 3 R group(s), and other variables are as defined in the present invention.

In some embodiments of the present invention, the above-mentioned $R_1$ is selected from a group consisting of Me, Et, $CF_3$, and

and other variables are as defined in the present invention.

In some embodiments of the present invention, the above-mentioned $R_2$, $R_3$, and $R_4$ are separately and independently selected from a group consisting of H, F, Cl, Br, I, OH, $NH_2$, and CN, or separately and independently selected from a group consisting of $C_{1-3}$alkyl and $C_{1-3}$alkoxy, both of which are optionally substituted by 1, 2 or 3 R group(s), and other variables are as defined in the present invention.

In some embodiments of the present invention, the above-mentioned $R_2$, $R_3$, and $R_4$ are separately and independently selected from a group consisting of H, F, Cl, Br, I, OH, $NH_2$, CN, Me, and

and other variables are as defined in the present invention.

In some embodiments of the present invention, the above-mentioned $R_5$ is selected from a group consisting of H and Me, and other variables are as defined in the present invention.

In some embodiments of the present invention, the above-mentioned $R_6$ is separately and independently selected from a group consisting of H, F, Cl, Br, I, OH, $NH_2$, and CN, or separately and independently selected from a group consisting of $C_{1-3}$alkyl and $C_{1-3}$heteroalkyl, both of which are optionally substituted by 1, 2 or 3 R group(s), and other variables are as defined in the present invention.

In some embodiments of the present invention, the above-mentioned $R_6$ is separately and independently selected from a group consisting of H, F, Cl, Br, I, OH, $NH_2$, and CN, or separately and independently selected from a group consisting of Me, Et,

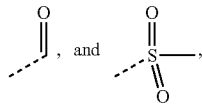

all of which are optionally substituted by 1, 2 or 3 R group(s), and other variables are as defined in the present invention.

In some embodiments of the present invention, the above-mentioned $R_6$ is separately and independently selected from a group consisting of H, F, Cl, Br, I, OH, $NH_2$, CN, Me, Et,

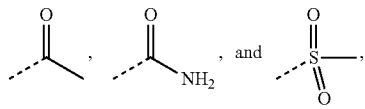

and other variables are as defined in the present invention.

In some embodiments of the present invention, the above-mentioned ring A is selected from a group consisting of $C_{4-6}$cycloalkyl, pyrrolidin-2-onyl, pyrimidin-4(3H)-onyl, 5-azaspiro[2.4]heptan-4-onyl, 4-azaspiro[2.4]heptan-5-onyl, tetrahydrothiophene-1,1-dioxide group, tetrahydrothiophene-1-oxide group, tetrahydrofuranyl, pyrrolidinyl, dihydrothiophene-2(3H)-onyl, 2-oxaspiro[3.4]octyl, dihydrofuran-2(3H)-onyl, 1,4,7,10-tetraoxacyclododecyl, 1,2,5-oxadiazolyl, 7-oxabicyclo-[2.2.1]heptane, pyrrolidin-2,5-dione, 5,5-dimethyl-dihydrofuran-2(3H)-onyl, and other variables are as defined in the present invention.

In some embodiments of the present invention, the above-mentioned structural unit

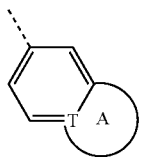

is selected from a group consisting of

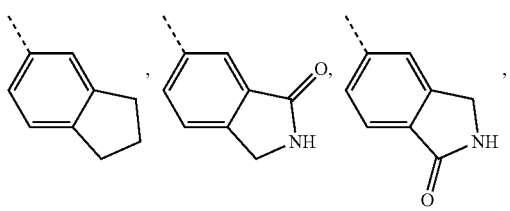

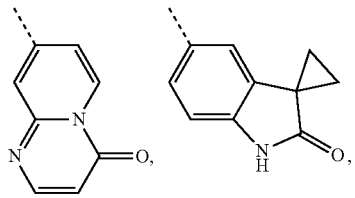

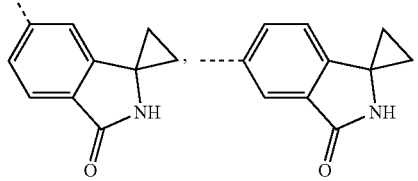

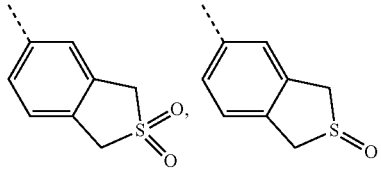

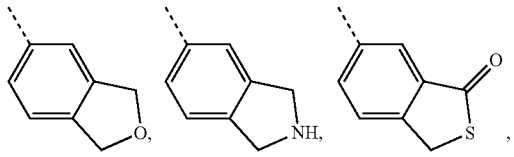

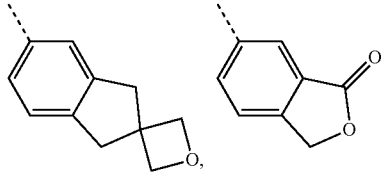

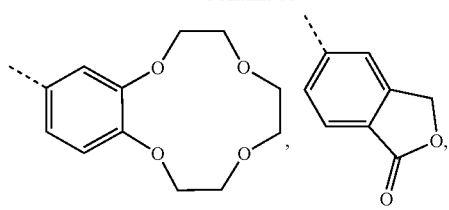

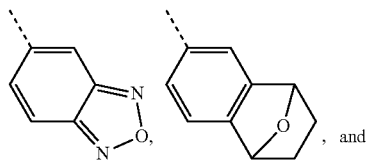

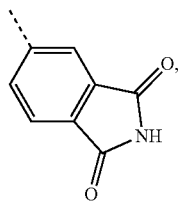

and other variables are as defined in the present invention.

In some embodiments of the present invention, the above-mentioned structural unit

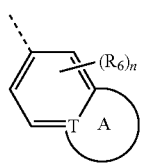

is selected from a group consisting of

7
-continued
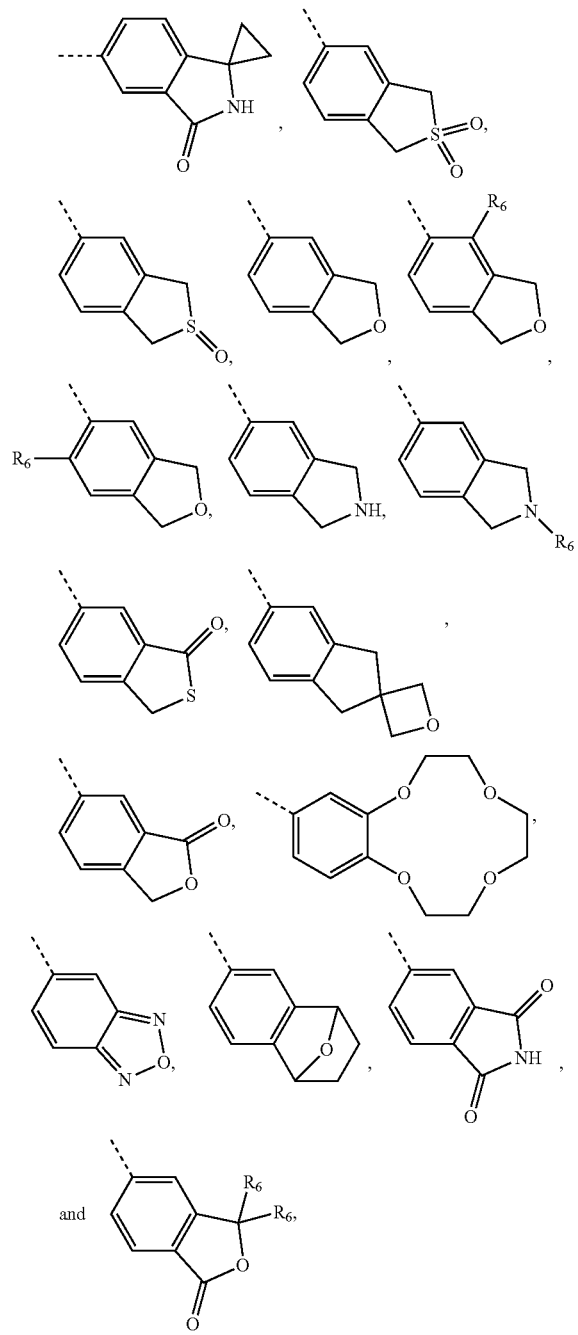
and other variables are as defined in the present invention.
In some embodiments of the present invention, the above-mentioned structural unit
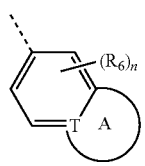
8
is selected from a group consisting of
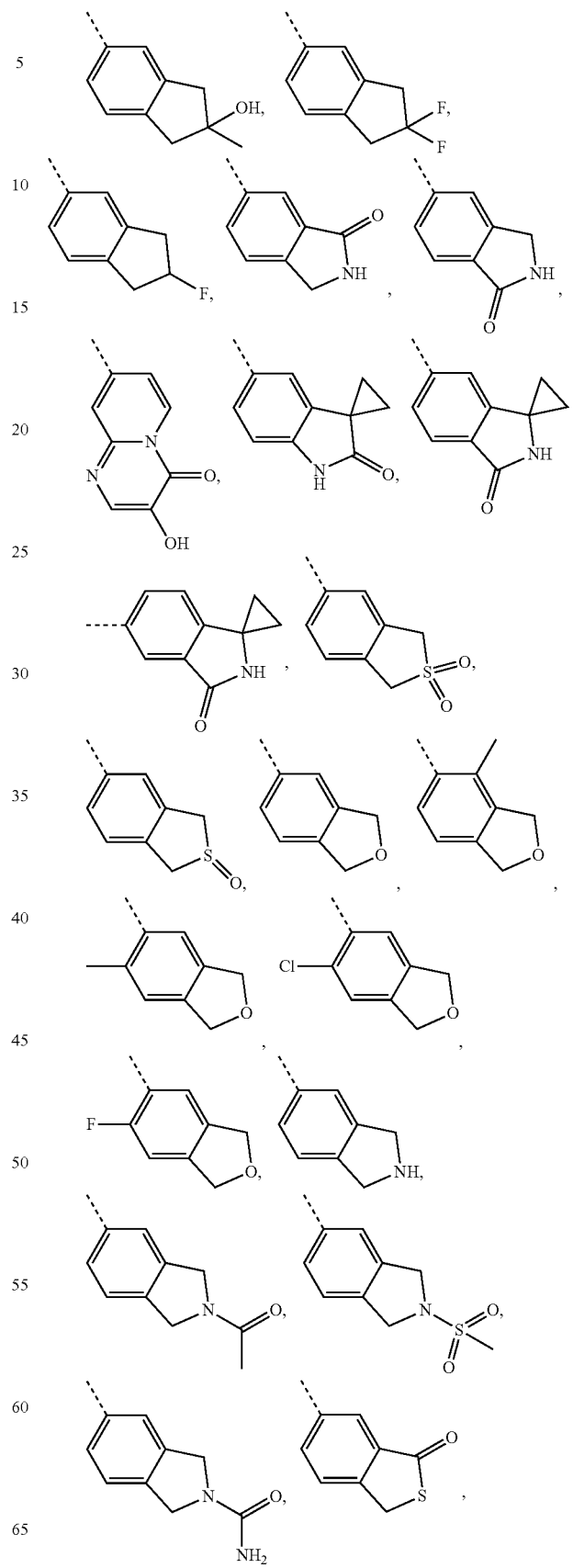

-continued

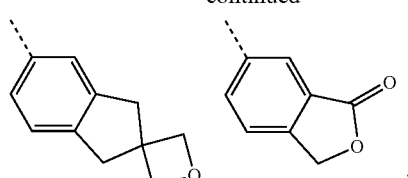

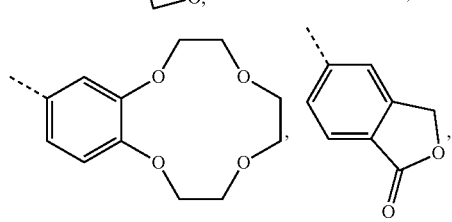

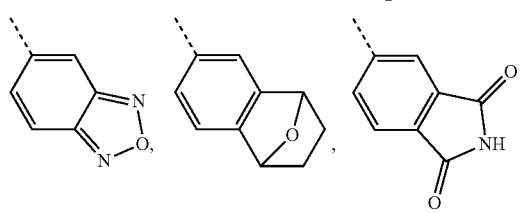

and 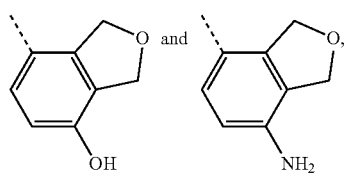

and other variables are as defined in the present invention.

In some embodiments of the present invention, the above-mentioned structural unit

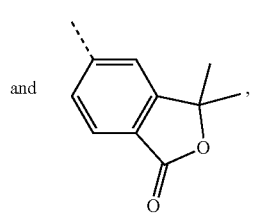

is selected from a group consisting of

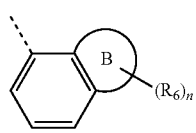

and other variables are as defined in the present invention.

The present invention also comprises some embodiments derived from any combination of the above-mentioned variables.

In some embodiments of the present invention, the above-mentioned compound, an isomer thereof or a pharmaceutically acceptable salt thereof, which is selected from a group consisting of

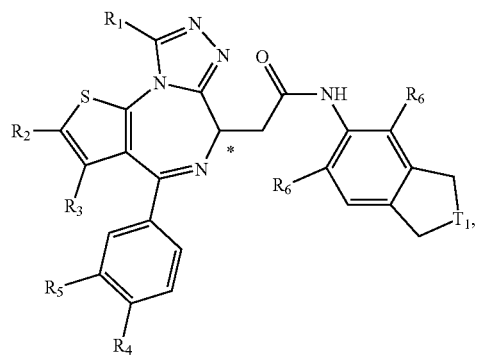

(I-1)

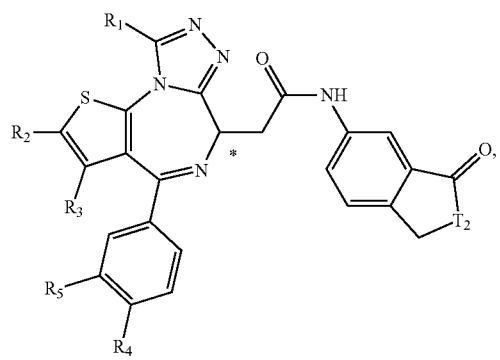

(I-2)

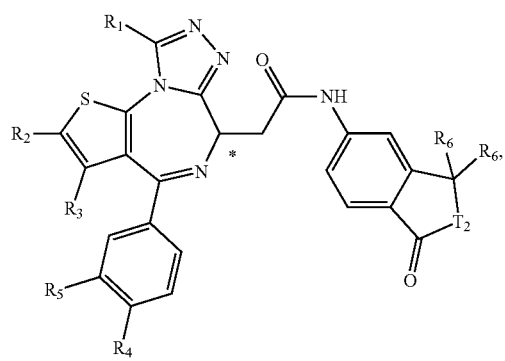

(I-3)

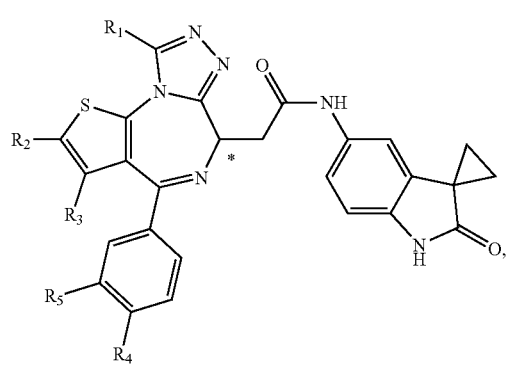

(I-4)

(I-5)
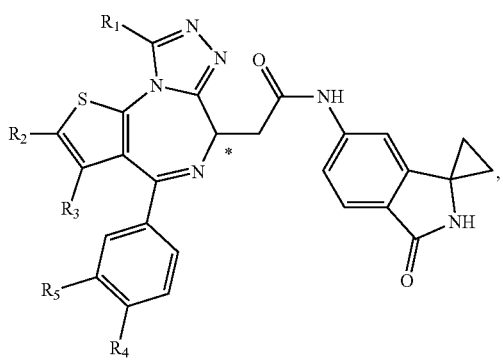

(I-6)
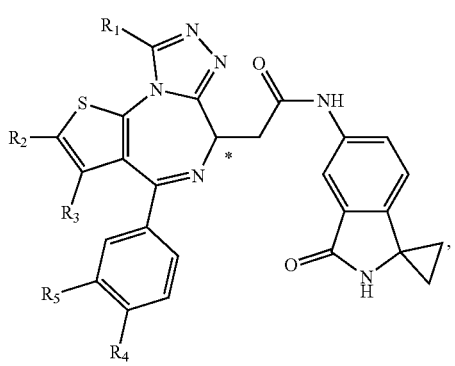

(I-7)
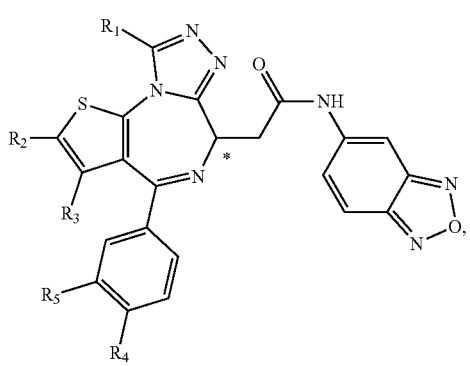

(I-8)
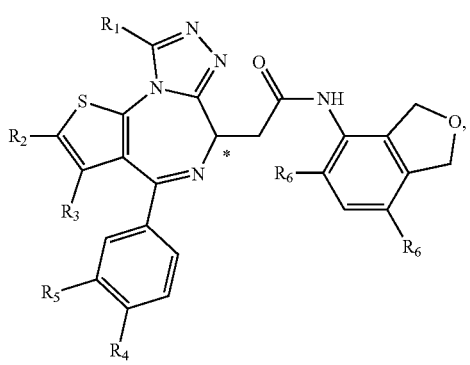

(I-9)
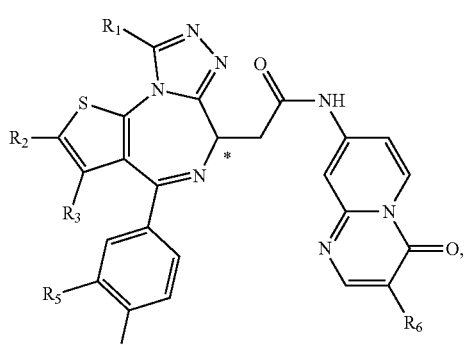

(I-10)
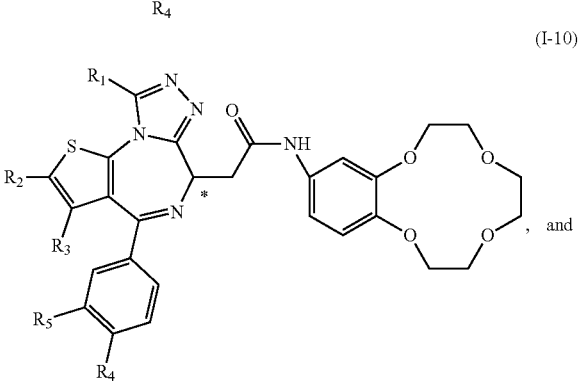
and (I-11)
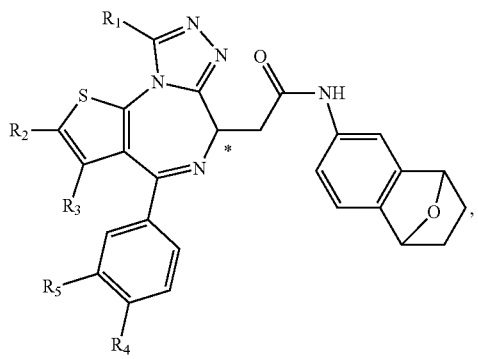

wherein, $T_1$ is selected from a group consisting of —S(=O)—, —S(=O)$_2$—, —N(R$_6$)—, —O—, —C(R$_6$)(R$_6$)—, and

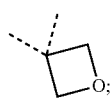

$T_2$ is separately and independently selected from a group consisting of —NH—, —O—, and —S—;

$R_1$-$R_6$ are as defined in the present invention;

the carbon atom marked with "*" is a chiral carbon atom, which is present in the form of a single (R) or (S) enantiomer, or in the form of being enriched in one of two enantiomers.

The present invention also provides a compound, an isomer thereof or a pharmaceutically acceptable salt thereof, which is selected from a group consisting of

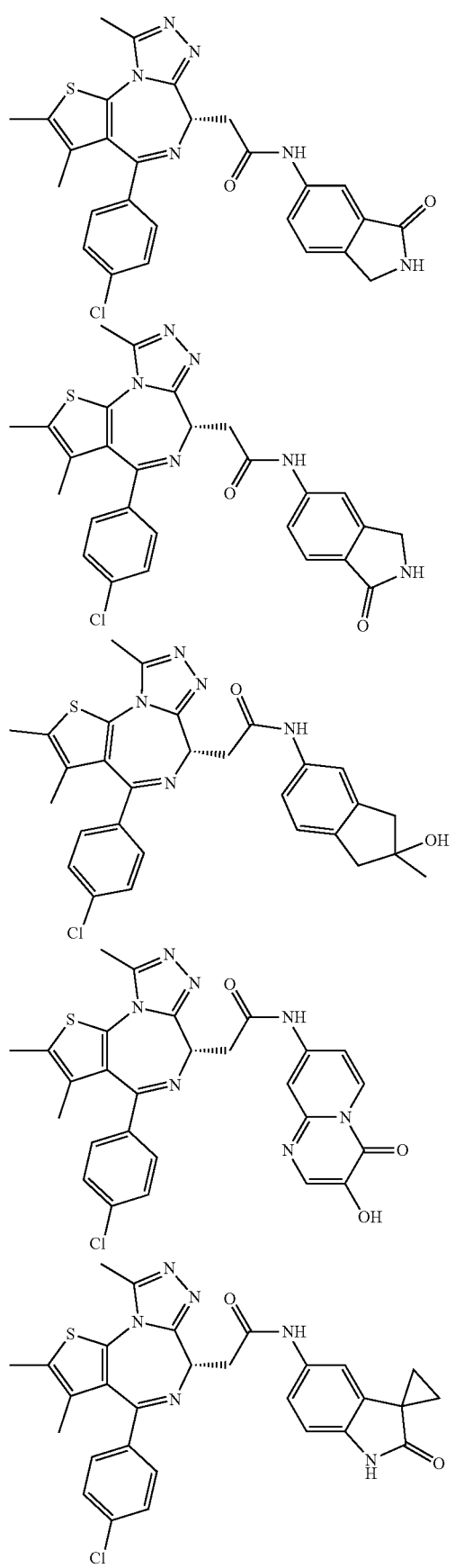
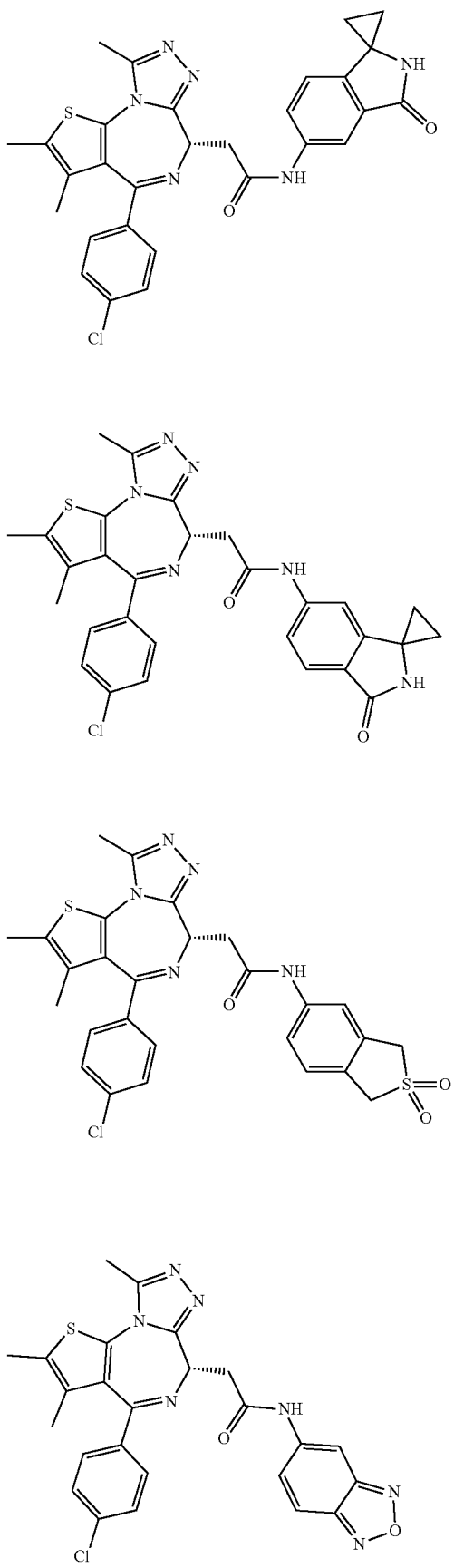

15
-continued
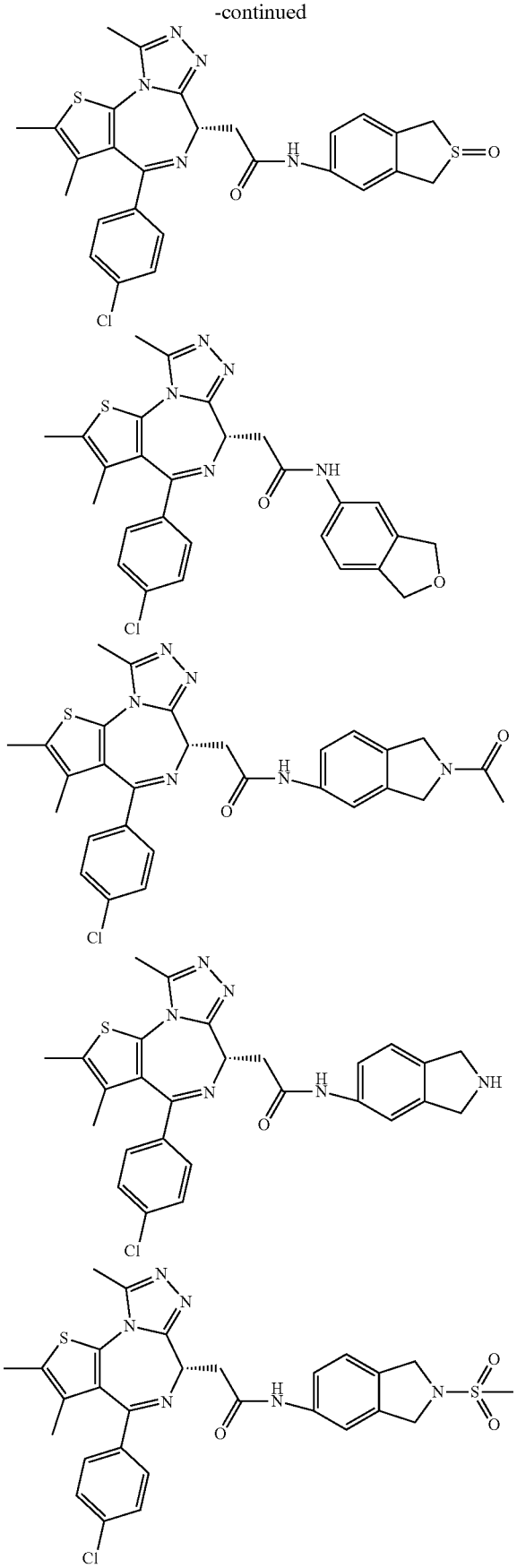
16
-continued
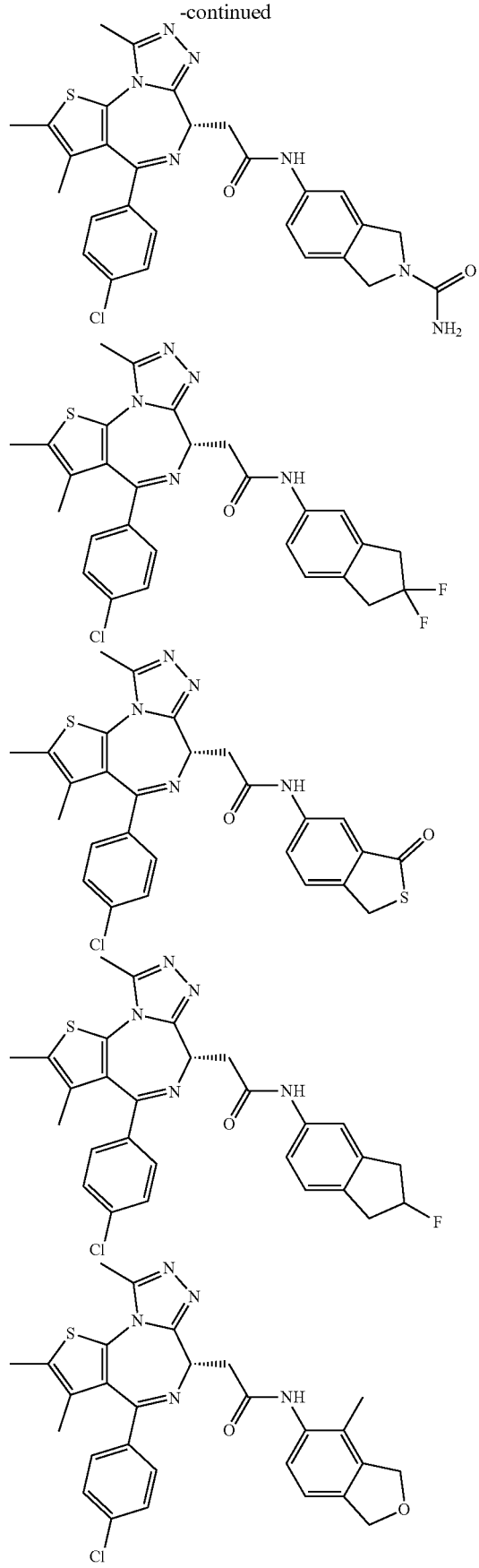

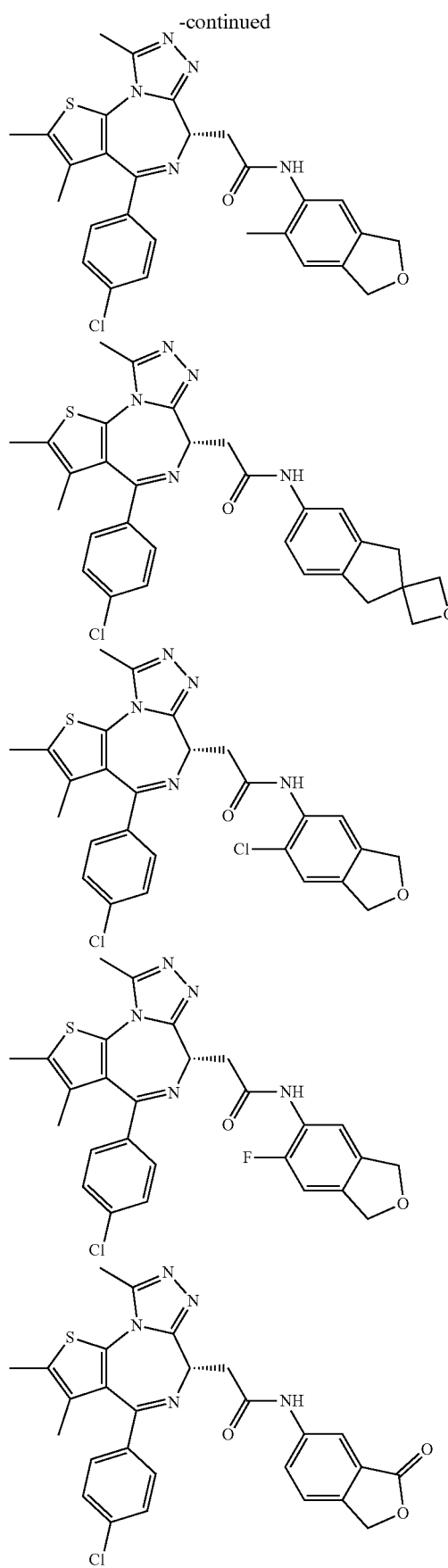
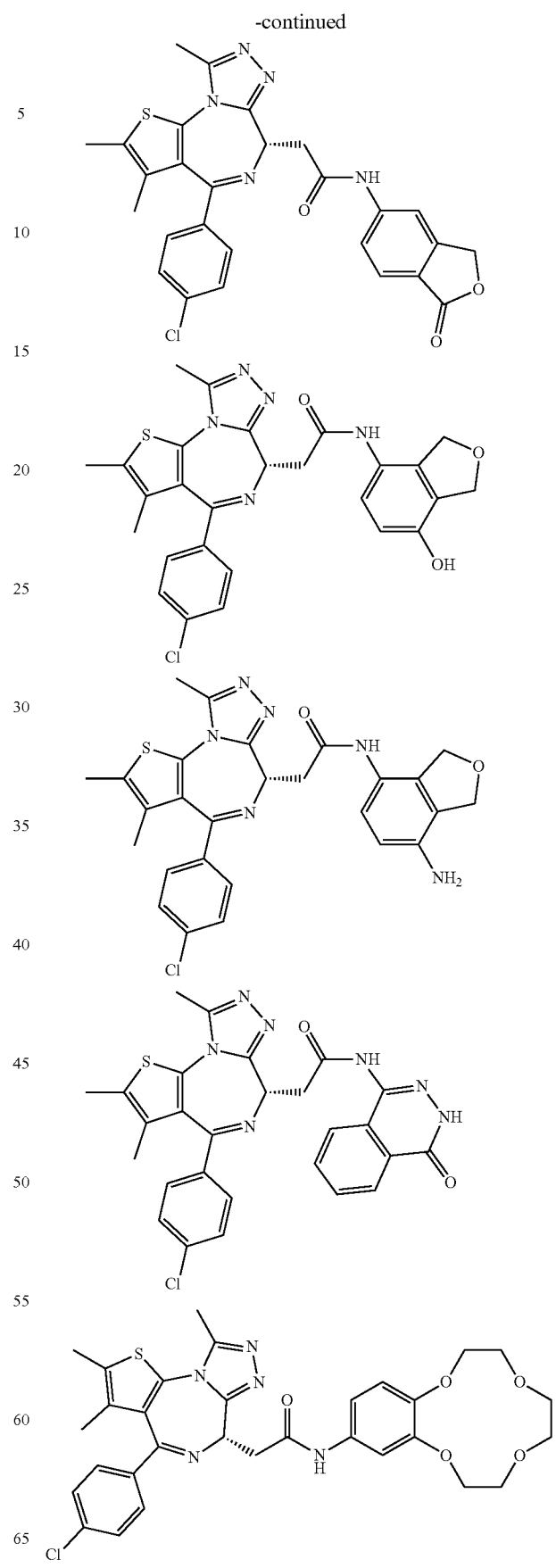

19
-continued
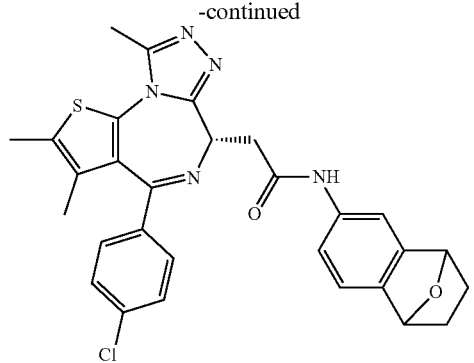
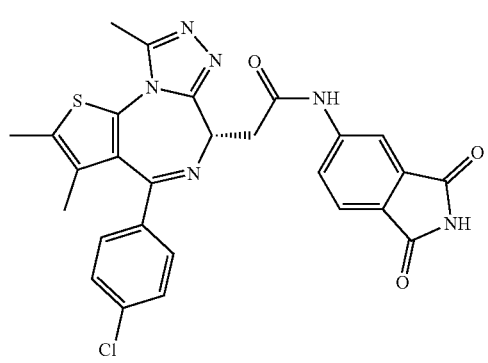
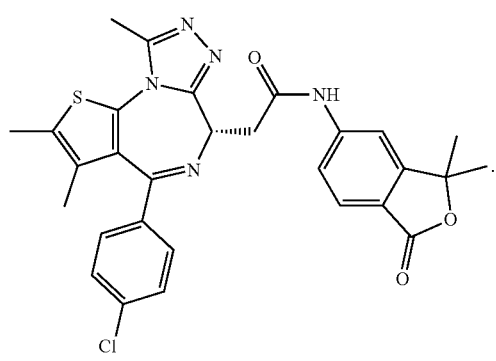
In some embodiments of the present invention, a compound, an isomer thereof or a pharmaceutically acceptable salt thereof, which is selected from a group consisting of
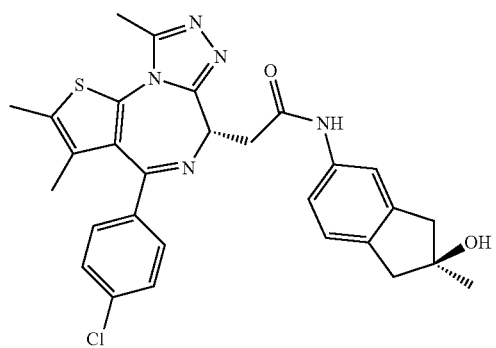
20
-continued
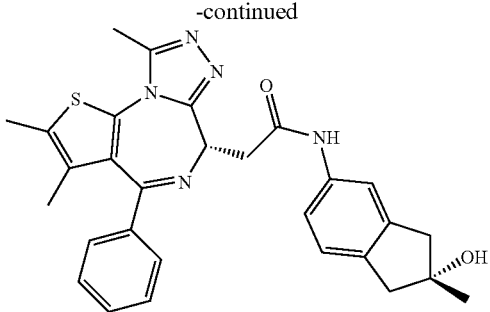
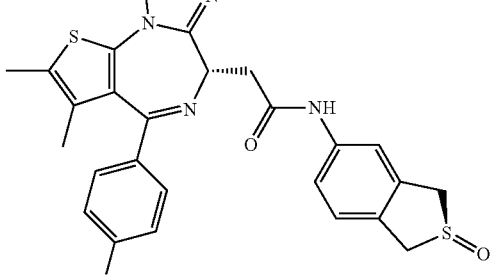
and
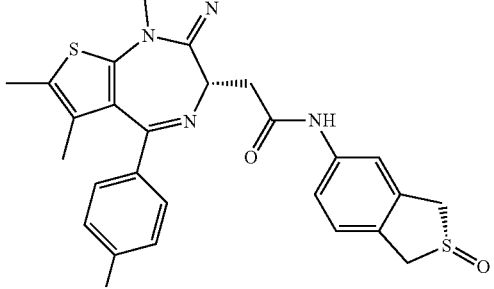
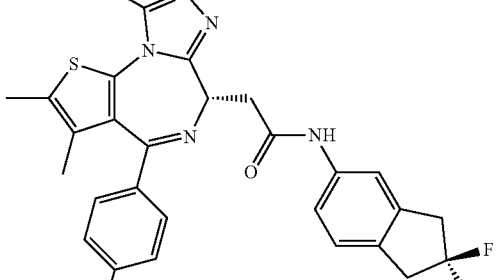
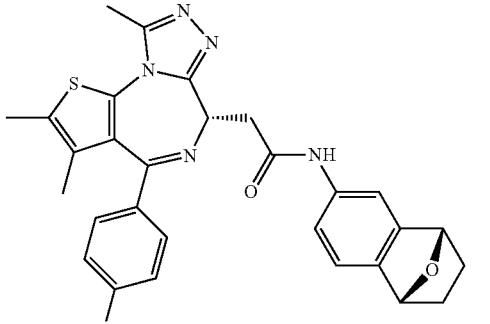

-continued

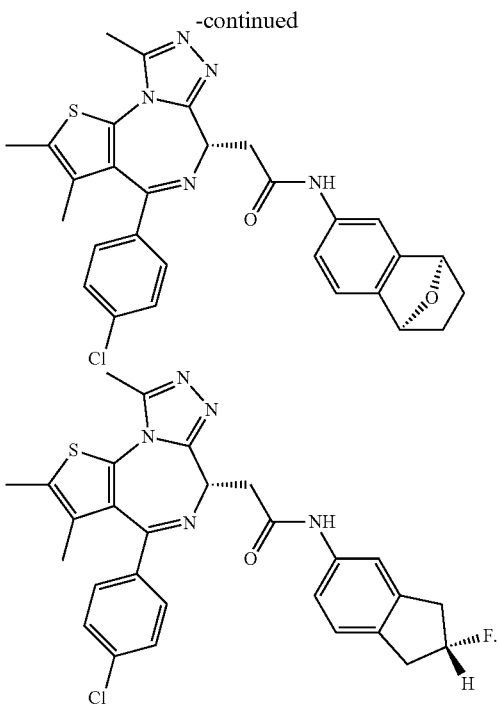

The present invention also provides a pharmaceutical composition, comprising a therapeutically effective amount of the above compound or a pharmaceutically acceptable salt thereof as an active ingredient and a pharmaceutically acceptable carrier.

The present invention also provides use of the above compound, an isomer thereof or a pharmaceutically acceptable salt thereof or the above composition in the manufacture of a BET Bromodomain inhibitor-related drug.

In some embodiments of the present invention, the above BET Bromodomain inhibitor-related drug is an antitumor drug.

Definition and Explanation

Unless otherwise stated, the following terms and phrases used herein are intended to have the following meanings. A particular term or phrase should not be considered uncertain or undistinct without a special definition but should be understood in its ordinary meaning. When a trading name appears herein, it is intended to refer to its corresponding commercial product or its active ingredient. The term "pharmaceutically acceptable" as used herein refers to those compounds, materials, compositions, and/or dosage forms which are, within the scope of sound medical judgment, suitable for use in contact with the tissues of humans and animals without undue toxicity, irritation, allergic response or other problems or complications, and are commensurate with a reasonable benefit/risk ratio.

The term "pharmaceutically acceptable salt" refers to a salt of the compound of the present invention, prepared from a compound having a specific substituent found in the present invention and a relatively non-toxic acid or base. When the compound of the present invention contains a relatively acidic functional group, a base addition salt can be obtained by contacting a sufficient amount of a base with a neutral form of such a compound in a pure solution or a suitable inert solvent. The pharmaceutically acceptable base addition salts include sodium, potassium, calcium, ammo- nium, organic amine or magnesium salts or similar salts. When the compound of the present invention contains a relatively basic functional group, an acid addition salt can be obtained by contacting a sufficient amount of an acid with a neutral form of such a compound in a pure solution or a suitable inert solvent. Examples of pharmaceutically acceptable acid addition salts include salts of inorganic acids, including, for example, hydrochloric acid, hydrobromic acid, nitric acid, carbonic acid, hydrocarbonate, phosphoric acid, monohydric phosphate, dihydric phosphate, sulfuric acid, hydrosulfate, hydroiodic acid, phosphorous acid, and the like; salts of organic acids, including, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid and the like; salts of amino acids (such as arginine); and salts of organic acids such as glucuronic acid. Certain specific compounds of the present invention contain both basic and acidic functionalities, and therefore can be converted into any of base or acid addition salts thereof.

The pharmaceutically acceptable salt of the present invention can be synthesized from the parent compound containing an acid group or a base group by a conventional chemical method. Generally, such salts are prepared by reacting these compounds in the form of free acid or base with a stoichiometric amount of an appropriate base or acid in water or an organic solvent or a mixture of the two.

The compounds of the present invention may exist in specific geometric or stereoisomeric forms. The present invention contemplates all such compounds, including cis- and trans-isomers, (−)- and (+)-pairs of enantiomers, (R)- and (S)-enantiomers, diastereoisomers, (D)-isomers, (L)- isomers, the racemic mixtures thereof, and other mixtures thereof, such as enantiomer or diastereoisomer-enriched mixtures, all of which fall within the scope of the invention. Additional asymmetric carbon atoms may be present in a substituent such as an alkyl group. All these isomers and their mixtures are included in the scope of the present invention.

Unless otherwise stated, the terms "enantiomers" or "optical isomers" refer to stereoisomers in mirror image relationship to each other.

Unless otherwise stated, the term "cis-trans isomer" or "geometric isomer" is caused by the inability of double bonds or single bonds of ring-forming carbon atoms to rotate freely.

Unless otherwise stated, the term "diastereoisomer" refers to a stereoisomer for which each of the molecules has two or more chiral centers and the molecules are in a non-mirror image relationship between each other.

Unless otherwise stated, "(D)" or "(+)" means the dextrorotation, "(L)" or "(−)" means the levorotation, and "(DL)" or "(±)" means the racemic.

Unless otherwise stated, the absolute configuration of a stereo-center is expressed with a wedge-shape solid line bond ( ) and a wedge-shape dashed line bond ( ), the relative configuration of a stereo-center is expressed with a straight-shape solid line bond ( ) and a straight-shape dashed line bond ( ), the wedge-shape solid line bond ( ) and/or the wedge-shape dashed line bond ( ) are expressed with a wavy line ( ), or the straight-shape solid line bond (⌁) and/or the straight-shape dashed line bond (⌁) are expressed with a wavy line (⌁).

The compounds of the present invention may exist in specific forms. Unless otherwise stated, the term "tautomer" or "tautomeric form" means that at room temperature, the isomers having different functional groups are in dynamic equilibrium and can be quickly converted to each other. If tautomers are possible (for example, in solution), the chemical equilibrium of the tautomers can be reached. For example, proton tautomers (also known as prototropic tautomers) include interconversions via proton migration, such as keto-enol isomerization and imine-enamine isomerization. Valence tautomers include the recombination of some bonding electrons for mutual conversion. Among others, a specific example of the keto-enol tautomerization is the interconversion between two tautomers of pentane-2,4-dione and 4-hydroxypent-3-en-2-one.

Unless otherwise stated, the term "enriched in an isomer", "isomerically enriched", "enriched in an enantiomer" or "enantiomerically enriched" refers to the content of an isomer or enantiomer is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term "isomer excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee value) is 80%.

Optically active (R)- and (S)-isomers, as well as D and L isomers, may be prepared with chiral synthesis, or chiral reagents, or other conventional techniques. If an enantiomer of the compound of the present invention is desired, it can be prepared by asymmetric synthesis or derivatization with a chiral auxiliary, in which the resulting diastereomeric mixture is separated and the auxiliary group is cleaved to provide the pure desired enantiomer. Alternatively, when the molecule contains a basic functional group (such as an amino group) or an acidic functional group (such as a carboxyl group), a diastereomeric salt is formed with an appropriate optically active acid or base, and then the diastereomeric resolution is performed with the conventional method well-known in the art, and then the pure enantiomer is recovered and obtained. In addition, the separation of enantiomers and diastereomers is usually accomplished by using chromatography, which employs a chiral stationary phase and is optionally combined with chemical derivatization (such as the generation of carbamate from amine). The compounds of the invention may contain an atomic isotope in an unnatural proportion on one or more of the atoms constituting the compound. For example, compounds can be labeled with radioisotopes, such as tritium ($^3H$), iodine-125 ($^{125}I$) or C-14 ($^{14}C$). Further, for example, hydrogen can be replaced with heavy hydrogen to form a deuterated drug, and the bond formed between deuterium and carbon is stronger than the bond formed between common hydrogen and carbon. Compared with undeuterated drugs, deuterated drugs have advantages such as reduced side effects, increased drug stability, enhanced therapeutic effectiveness, and prolonged drug's biological half-life. Transformations of all isotopic compositions of the compounds of the present invention, whether radioactive or not, are included within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream matrix, lotion matrix, ointment matrix and the like. These matrices include a suspending agent, a thickener, a skin-penetration enhancer and the like. Their formulations are well known to the skilled in the cosmetic field or the topical pharmaceutical field.

"Optional" or "optionally" refers to events or conditions described later that may, but need not, occur, and this description includes situations in which the events or conditions occur and situations in which the events or conditions do not occur.

The term "substituted" refers to the replacement of any one or more hydrogen atoms on a specific atom with a substituent that may include deuterium and hydrogen variants, as long as the valence of the specific atom is normal and the substituted compound is stable. When the substituent is oxygen (=O), it means that two hydrogen atoms are substituted. Oxygen substitution does not occur on an aromatic group. The term "optionally substituted" means that it may or may not be substituted, and unless otherwise specified, the kind and number of substituents may be arbitrary on the basis of chemically achievable.

When any variable (such as R) appears more than once in the composition or structure of a compound, its definition in each case is independent. Thus, for example, if a group is substituted with 0-2 R substituent(s), the group may be optionally substituted by at most two R substituents, and for each substituent, R has an independent option. In addition, the combination of substituents and/or variants thereof are permitted only if such combination results in a stable compound.

When the number of a linking group is 0, such as —(CRR)$_0$—, it means that the linking group is a single bond.

When one of the variables is selected from a single bond, the two groups connected thereto are directly connected. For example, when L represents a single bond in A-L-Z, the structure is actually A-Z.

When a substituent is vacant, it represents that the substituent is not present. For example, if X in A-X is vacant, it represents that the structure is actually A. When a substituent may be attached to more than one atom on a ring, this substituent may be bonded to any atom on the ring. For example, the structural unit

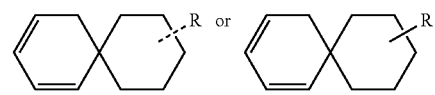

represents that the substitution with the R substituent may appear on any position of the cyclohexyl or cyclohexadiene. In case of not indicating which atom in the listed substituent will be attached to the group to be substituted, this substituent may be attached via any atom thereof. For example, a pyridyl group as a substituent group may be attached to a group to be substituted via any carbon atom on the pyridine ring. In case of not indicating the linking direction of the listed linking group, its linking direction is arbitrary. For example, in

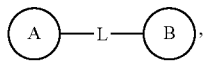

the linking group L is -M-W—; at this time, -M-W— can either link ring A and ring B in the same direction as the reading order from the left to the right to form

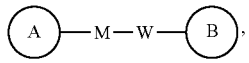

or link ring A and ring B in the direction opposite to the reading order from the left to the right to form

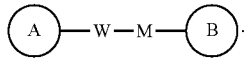

The combination of the linking group, substituents and/or variants thereof are permitted only if such combination results in a stable compound.

Unless otherwise specified, "ring" represents substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a linked ring, a spiro ring, a fused ring or a bridged ring. The number of atoms on a ring is usually defined as the member number of rings. For example, "5-7 membered ring" means 5-7 atoms arranged in a circle. Unless otherwise specified, the ring optionally contains 1-3 heteroatoms. Thus, "5-7 membered ring" includes, for example, phenyl, pyridinyl, and piperidinyl; on the other hand, the term "5-7 membered heterocycloalkyl ring" includes pyridyl and piperidyl, but does not include phenyl. The term "ring" also includes a ring system containing at least one ring, each of which "ring" independently meets the above definition.

Unless otherwise specified, the term "heterocycle" or "heterocyclyl" means a stable heteroatom or hetero group-containing monocyclic, bicyclic, or tricyclic ring, which may be saturated, partially unsaturated, or unsaturated (aromatic) and contain carbon atoms and 1, 2, 3, or 4 ring heteroatoms independently selected from N, O, and S, wherein any of the above heterocycles can be fused to a benzene ring to form a bicyclic ring. Nitrogen and sulfur heteroatoms can optionally be oxidized (i.e., NO and S(O)p, where p is 1 or 2). The nitrogen atom may be substituted or unsubstituted (i.e., N or NR, where R is H or other substituents as defined herein). The heterocycle can be attached to a side group of any heteroatom or carbon atom to form a stable structure. If the resulting compound is stable, the heterocycle described herein can undergo the substitution at the carbon or nitrogen position. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed 1. As used herein, the term "aromatic heterocyclic group" or "heteroaryl" means a stable 5-, 6-, 7-membered monocyclic or bicyclic or 7-, 8-, 9- or 10-membered bicyclic heterocyclic aromatic ring, which contains carbon atoms and 1, 2, 3 or 4 ring heteroatoms independently selected from N, O and S. The nitrogen atom may be substituted or unsubstituted (i.e., N or NR, where R is H or other substituents as defined herein). Nitrogen and sulfur heteroatoms can optionally be oxidized (i.e., NO and $S(O)_p$, where p is 1 or 2). It is worth noting that the total number of S and O atoms on the aromatic heterocycle does not exceed 1. The bridged ring is also included in the definition of the heterocycle. The bridged ring is formed when one or more atoms (i.e., C, O, N, or S) connect two non-adjacent carbon or nitrogen atoms. The preferred bridged ring includes but is not limited to, one carbon atom, two carbon atoms, one nitrogen atom, two nitrogen atoms, and one carbon-nitrogen group. It is worth noting that a bridge always converts a single ring into a tricyclic ring. In the bridged ring, the substituent on the ring may also appear on the bridge.

The example of the heterocycle compound includes, but is not limited to, acridinyl, azocinyl, benzimidazolyl, benzofuranyl, mercapto benzofuranyl, mercapto benzophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridino-oxazole, pyridino-imidazole, pyridino-thiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1, 2,3-triazolyl, 2H-1,2,3-triazolyl, 1H-1,2,4-triazolyl, 4H-1,2, 4-triazolyl, and xanthenyl. Also included are the fused-ring compound and the spiro-ring compound.

Unless otherwise specified, the term "hydrocarbyl" or its subordinate concept (e.g. alkyl, alkenyl, alkynyl, aryl and the like), by itself or as part of another substituent, refers to a linear, branched-chain or cyclic hydrocarbon radical or any combination thereof. They can be fully saturated (e.g. alkyl), mono- or poly-unsaturated (e.g. alkenyl, alkynyl, and aryl), can be mono-, or poly-substituted, can be monovalent (e.g. methyl), divalent (e.g. methylene) or multivalent (e.g. methynyl), can also include a divalent or multivalent group, have a specified number of carbon atom (for example, $C_1$-$C_{12}$ indicates 1-12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$, and $C_{12}$; $C_{3-12}$ is selected from $C_3$, $C_4$, $C_5$, $C_6$, $C_7$, $C_8$, $C_9$, $C_{10}$, $C_{11}$, and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but is not limited to alkyl, alkenyl, and alkynyl. The aromatic hydrocarbyl includes but is not limited to 6-12 membered aromatic hydrocarbyl such as phenyl, naphthalenyl and the like. In some embodiments, the term "hydrocarbyl" refers to a linear or branched group or a combination thereof which can be fully saturated, mono- or poly-unsaturated, and can include a divalent or multivalent group. The example of the saturated hydrocarbyl group includes, but is not limited to, methyl, ethyl, n-propyl, isopropyl, n-butyl, tert-butyl, isobutyl, sec-butyl, isobutyl, cyclohexyl, (cyclohexyl)methyl, cyclopropylmethyl, and the homolog or isomer of n-pentyl, n-hexyl, n-heptyl, n-octyl, and the similar groups. The unsaturated hydrocarbyl has one or more than one double or triple bonds, and the example thereof includes but is not limited to ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers. Unless otherwise specified, the term "heterohydrocarbyl" or its subordinate concept (e.g. heteroalkyl, heteroalkenyl, heteroalkynyl, heteroaryl and the like), by itself or in the combination of another term, refers to a stable linear, branched or cyclic hydrocarbon group or any combination thereof, which is composed of a specified number of carbon atoms and at least one heteroatom. In some embodiments, the term "heteroalkyl", by itself or in the combination of another term, refers to a stable linear or branched hydrocarbon group or any combination thereof, which is composed of a specified number of carbon atoms and at least one heteroatom. In a specific embodiment, the heteroatom is selected from B, O, N, and S, wherein the nitrogen and sulfur atoms are optionally oxidized and the nitrogen atom is optionally quaternized. The heteroatom or the hetero group can be located at any interior position of a heterohydrocarbyl, including the position where the hydrocarbyl attaches to the rest part of the molecule. But the terms "alkoxy", "alkylamino" and "alkylthio" (or alkoxyl in which O is replaced with S) belong to the idiomatic expression and refer to an alkyl group connected to the remaining part of the molecule via an oxygen atom, an amino group or a sulfur atom respectively. The example includes, but is not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two heteroatoms can be consecutive, for example, —$CH_2$—NH—$OCH_3$.

Unless otherwise specified, the term "cyclohydrocarbyl", "heterocyclohydrocarbyl" or its subordinate concept (e.g. aryl, heteroaryl, cycloalkyl, heterocycloalkyl, cycloalkenyl, heterocycloalkenyl, cycloalkynyl, heterocycloalkynyl and the like) by itself or in combination with another term refers to cyclized "hydrocarbyl" and "heterohydrocarbyl" respectively.

Furthermore, for heterohydrocarbyl or heterocyclohydrocarbyl (e.g. heteroalkyl and heterocycloalkyl), the heteroatom can occupy the position where the heterocycle attaches to the remaining position of the molecule. The example of the cyclohydrocarbyl includes, but is not limited to, cyclopentyl, cyclohexyl, 1-cyclohexenyl, 3-cyclohexenyl, cycloheptyl and the like. The non-limiting example of heterocycloalkyl includes 1-(1,2,5,6-tetrahydropyridinyl), 1-piperidinyl, 2-piperidinyl, 3-piperidinyl, 4-morpholinyl, 3-morpholinyl, tetrahydrofuran-2-yl, tetrahydrofuran indole-3-yl, tetrahydro-thiophen-2-yl, tetrahydro-thiophen-3-yl, 1-piperazinyl and 2-piperazinyl.

Unless otherwise specified, the term "alkyl" refers to a straight or branched saturated hydrocarbyl, which can be mono-substituted (e.g. —$CH_2F$) or poly-substituted (e.g. —$CF_3$), and can be monovalent (e.g. methyl), divalent (e.g. methylene) or multivalent (e.g. methenyl). The example of alkyl includes methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, cycloalkyl includes any stable cyclic or polycyclic hydrocarbyl, any carbon atom of which is saturated, and which can be mono-substituted or poly-substituted and can be monovalent, divalent or multivalent. The example of cycloalkyl includes, but is not limited to, cyclopropyl, norbornanyl, [2.2.2]bicyclooctane, [4.4.0]bicyclodecane and the like. Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo ($C_1$-$C_4$)alkyl" is meant to include, but not limited to, trifluoromethyl, 2,2,2-trifluoroethyl, 4-chlorobutyl, 3-bromopropyl and the like. Unless otherwise specified, the example of haloalkyl includes, but is not limited to trifluoromethyl, trichloromethyl, pentafluoroethyl, and pentachloroethyl.

"Alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. The example of alkoxy includes, but is not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic hydrocarbon substituent, which can be mono-, or poly-substituted, can be a monovalent, divalent or multivalent, can be monocyclic or polycyclic (e.g. containing 1-3 rings; wherein at least one ring is aromatic), and can be fused together or connected covalently. The term "heteroaryl" refers to an aryl group (or ring) containing one to four heteroatoms. In an illustrative example, the heteroatom is selected from a group consisting of B, O, N, and S, wherein the nitrogen and sulfur atoms are optionally oxidized and nitrogen atom is optionally quaternized. A heteroaryl may attach to the rest part of the molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridinyl, pyrimidyl, benzothiazolyl, purinyl, benzimidazoyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridinyl, 3-pyridinyl, 4-pyridinyl, 2-pyrimidyl, 4-pyrimidyl, 5-benzothiazolyl, purinyl, 2-benzimidazoyl, 5-indolyl, 1-isoquinolyl, 5-isoquinolyl, 2-quinoxalinyl, 5-quinoxalinyl, 3-quinolyl, and 6-quinolyl. The substituent of any of the above aryl and heteroaryl ring system is selected from a group consisting of the acceptable substituent described below.

Unless otherwise specified, when combined with other terms (such as aryloxy, arylthio, arylalkyl), the aryl includes the aryl and heteroaryl ring as defined above. Thus, the term "arylalkyl" is meant to include a group (e.g. benzyl, phenylethyl, pyridylmethyl, and the like) where an aryl is attached to an alkyl, including an alkyl where the carbon atom (e.g. methylene) has been replaced by an atom such as oxygen, for example, phenoxymethyl, 2-pyridyloxymethyl-3-(1-naphthyloxy)propyl, and the like.

The term "leaving group" refers to a functional group or atom which can be replaced by another functional group or atom through a substitution reaction (such as nucleophilic substitution reaction). For example, the representative leaving group includes triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "mercapto protecting group". The term "amino protecting group" refers to a protecting group suitable for blocking the side reaction on the nitrogen position of an amino. Representative amino protecting groups include, but are not limited to: formyl; acyl, such as alkanoyl (e.g. acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl, and tert-butyl; acyl such as alkanoyl (e.g. acetyl); arylmethyl such as benzyl (Bn), p-methoxybenzyl (PMB), 9-fluorenylmethyl (Fm), and diphenylmethyl (DPM); silyl such as trimethylsilyl (TMS) and tert-butyl dimethylsilyl (TBS) and the like.

The compound of the present invention can be prepared by a variety of synthesis methods well known to those skilled in the art, including the following enumerative embodiments, the embodiments formed by the following enumerative embodiments in combination with other chemical synthesis methods and the equivalent substitute modes well known to those skilled in the art. The preferred embodiment includes but is not limited to the examples of the present invention.

All of the solvents used in the present invention are commercially available. The present invention adopts the following abbreviations: aq represents water; HATU represents O-(7-aza-benzotriazole-1-yl)-N,N,N',N'-tetramethyluronium hexafluorophosphate; EDC represents N-(3-dimethylaminopropyl)-N'-ethyl carbodiimide hydrochloride; m-CPBA represents 3-chloroperoxy benzoic acid; eq represents equivalent, equivalent amount; CDI represents carbonyl diimidazole; DCM represents methylene chloride; PE represents petroleum ether; DIAD represents diisopropyl azodiformate; DMF represents N,N-dimethyl formamide; DMSO represents dimethyl sulfoxide; EtOAc represents ethyl acetate; EtOH represents ethanol; MeOH represents methanol; CBz represents benzyloxycarbonyl, an amine protecting group; BOC represents tert-butoxylcarbonyl, an amine protecting group; HOAc represents acetic acid; NaCNBH$_3$ represents sodium cyanoborohydride; r.t. represents room temperature; O/N represents overnight; THF represents tetrahydrofuran; Boc$_2$O represents di-tert-butyl dicarbonate; TFA represents trifluoroacetic acid; DIPEA represents diisopropylethylamine; SOCl$_2$ represents thionyl chloride; CS$_2$ represents carbon bisulfide; TsOH represents paratoluenesulfonic acid; NFSI represents N-fluoro-N-(benzenesulfonyl)benzenesulfonamide; NCS represents 1-chloro-pyrrolidine-2,5-dione; n-Bu$_4$NF represents tetrabutylammonium fluoride; iPrOH represents 2-propyl alcohol; mp represents melting point; LDA represents lithium diisopropylamide; EDCI represents 1-(3-dimethylaminopropyl)-3-ethyl carbodiimide hydrochloride; dppf represents 1,1'-bis(diphenylphosphine)ferrocene; HATU represents 2-(7-benzotriazole oxide)-N,N,N',N'-tetramethylurea hexafluorophosphate; Ti(i-PrO)$_4$ represents titanium tetraisopropoxide; NBS represents N-bromosuccinimide; dast represents diethylamino sulfur trifluoride; LiHMDS represents lithium hexamethyldisilazide; AIBN represents azobisisobutyronitrile; POCl$_3$ represents phosphorus oxychloride; PEG400 represents polyethylene glycol 400.

Compounds are named manually or by ChemDraw® software, and the commercially available compounds use their supplier's directory names.

Technical effect: the compound of the present invention has a significant BET Bromodomain inhibition activity and a significant tumor inhibition effect, and has good tolerance for animals; meanwhile, the compound of the present invention has a low pharmacokinetic clearance and good absorption.

A DETAILED DESCRIPTION OF THE PREFERRED EMBODIMENTS

The present invention will be specifically described below by way of examples, but it does not imply any disadvantageous limitation to the present invention. The present invention has been described in detail herein, and its specific embodiments are also disclosed. It will be obvious to those skilled in the art that various changes and improvements can be made to the specific embodiments of the present invention without departing from the spirit and scope of the present invention.

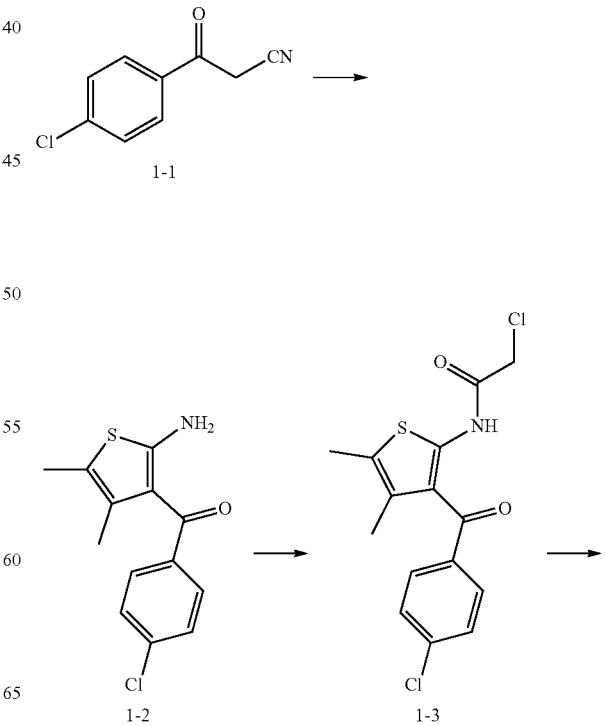

-continued
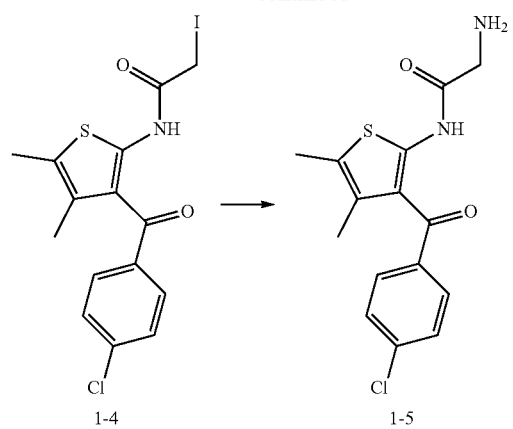
1-4 → 1-5
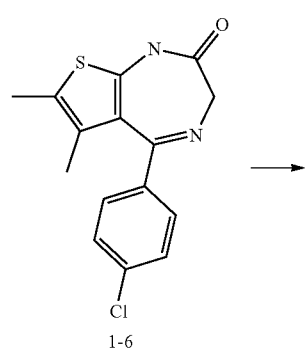
1-6 →
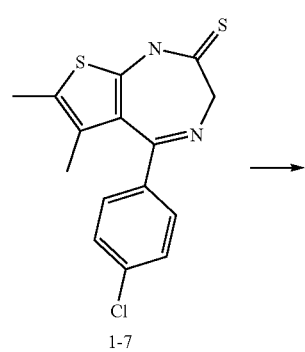
1-7 →
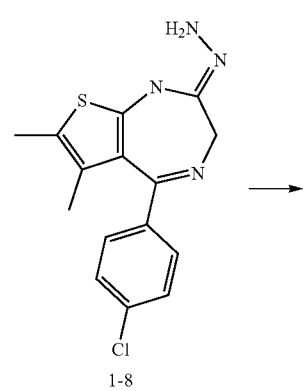
1-8
-continued
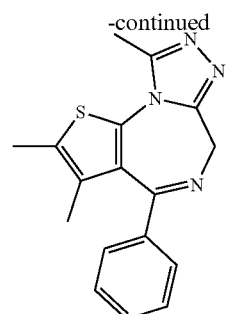
1-9 →
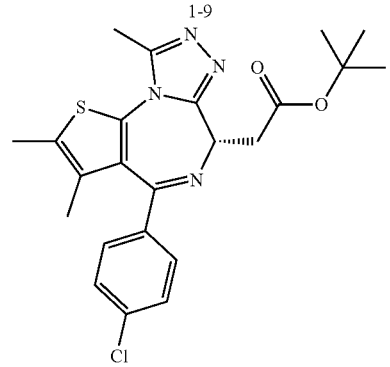
1-10 →
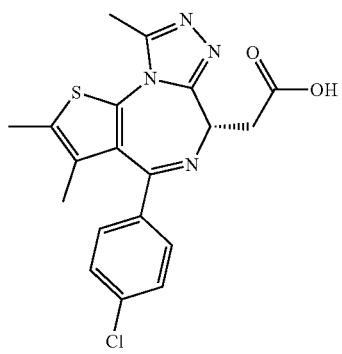
1-11 →
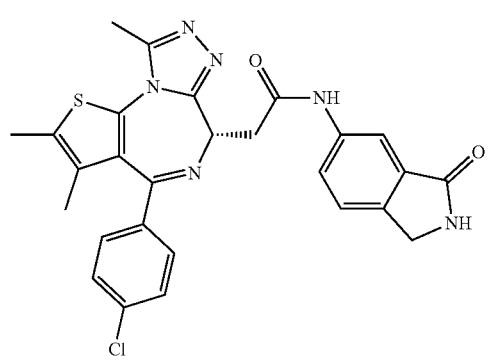
1

Example 1

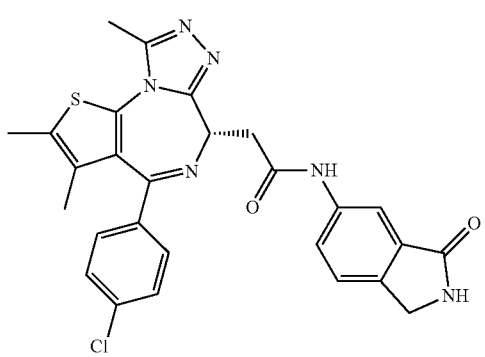 [SMILES: Cc1sc2c(c1C)C(c1ccc(Cl)cc1)=N[C@@H](CC(=O)Nc1ccc3c(c1)C(=O)NC3)c1nnc(C)n1-2]

Synthesis of Compound 1-2

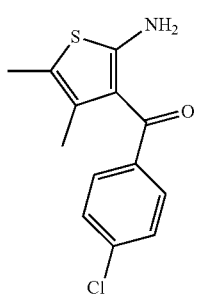 [SMILES: Cc1sc(N)c(C(=O)c2ccc(Cl)cc2)c1C]

Compound 1-1 (25.00 g, 139.20 mmol, 1.00 eq), 2-butanone (11.04 g, 153.12 mmol, 13.63 mL, 1.10 eq) and morpholine (12.13 g, 139.20 mmol, 12.25 mL, 1.00 eq) were dissolved in ethanol (200.00 mL), and a sublimed sulfur (4.46 g, 139.20 mmol, 1.00 eq) was added. The suspension was warmed up to 70° C. and stirred under the protection of nitrogen gas for 12 hours. The reaction mixture was concentrated under reduced pressure to give a yellow oil. Water (500 mL) was added to the oily substance, and the resulting mixture was extracted with ethyl acetate (200 mL×4). The combined organic phases were collected, washed with a saturated saline solution (200 mL), dried over anhydrous sodium sulfate, filtered and concentrated under reduced pressure. The obtained crude product was purified by a silica gel column (petroleum ether/ethyl acetate=10/1) to give the compound 1-2. $^1$H NMR (400 MHz, CDCl$_3$) δppm 7.47 (d, J=8.0 Hz, 2H), 7.38 (d, J=8.0 Hz, 2H), 6.43 (br s, 2H), 2.13 (s, 3H), 1.56 (s, 3H).

Synthesis of Compound 1-3

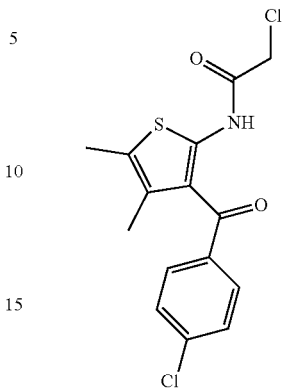

Compound 1-2 (10.00 g, 37.63 mmol, 1.00 eq) was dissolved in chloroform (100.00 mL) and 2-chloroacetyl chloride (6.37 g, 56.45 mmol, 4.49 mL, 1.50 eq) was added dropwisely. After the completion of the dropwise addition, the reaction mixture was stirred at 70° C. for 1 hour. The reaction mixture was washed with a saturated sodium bicarbonate solution (100 mL) and a saturated saline solution (50 mL), then dried over anhydrous sodium sulfate, filtered, and then concentrated under reduced pressure. The obtained compound as a crude product was recrystallized with methanol (40 mL) to give the compound 1-3. $^1$H NMR (400 MHz, CDCl$_3$) δppm 11.81 (br s, 1H), 7.58 (dd, J=2.0, 6.4 Hz, 2H), 7.45 (dd, J=2.2, 8.6 Hz, 2H), 4.25 (s, 2H), 2.29 (s, 3H), 1.72 (s, 3H).

Synthesis of Compound 1-4

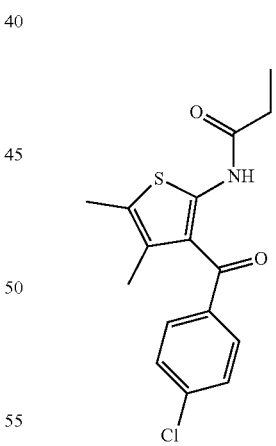

Compound 1-3 (11.00 g, 32.14 mmol, 1.00 eq) and sodium iodide (9.63 g, 64.28 mmol, 2.00 eq) were added to tetrahydrofuran (50.00 mL). The resulting mixture was stirred at 60° C. for 2 hours. The reaction mixture was directly concentrated under reduced pressure to give compound 1-4, which was not purified and directly used in the next step of the reaction. LCMS (ESI) m/z: 433.9 (M+1).

Synthesis of Compound 1-5

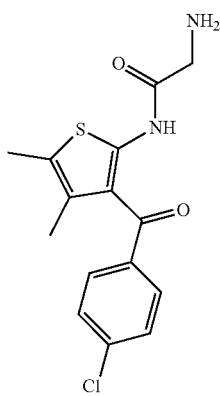 [SMILES: Cc1sc(NC(=O)CN)c(C(=O)c2ccc(Cl)cc2)c1C]

Compound 1-4 (14.00 g, 32.28 mmol, 1.00 eq) was dissolved in tetrahydrofuran (100.00 mL). The resulting mixture was cooled to −60° C. and ammonia gas was charged for 30 minutes. The resulting reaction mixture was slowly warmed up to 20° C. and stirred for 3 hours. The reaction mixture was directly concentrated under reduced pressure. The obtained solid was dissolved in ethyl acetate (150 mL) and washed with water (50 mL×3) and a saturated saline solution (50 mL), dried over anhydrous sodium sulfate, filtered, and then concentrated under reduced pressure. The obtained compound 1-5 was directly used in the next step of the reaction. LCMS (ESI) m/z: 322.9 (M+1), 344.9 (M+Na).

Synthesis of Compound 1-6

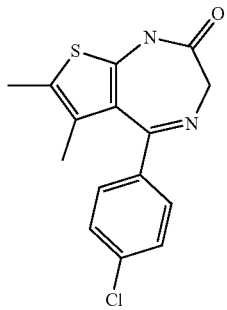 [SMILES: Cc1sc2c(c1C)C(c1ccc(Cl)cc1)=NCC(=O)N2]

Compound 1-5 (10.00 g, 30.98 mmol, 1.00 eq) was dissolved in isopropanol (150.00 mL) and glacial acetic acid (50.00 mL). The resulting mixture was stirred at 90° C. for 3 hours. The solvent was removed under reduced pressure from the reaction mixture. The residual mixture was dissolved in chloroform (20 mL), washed with a saturated sodium bicarbonate solution (20 mL) and a saturated saline solution (20 mL), dried over anhydrous sodium sulfate, filtered, and then concentrated under reduced pressure. The compound as a crude product was recrystallized with ethyl acetate (50 mL) to give compound 1-6. $^1$H NMR (400 MHz, CDCl$_3$) δppm 8.98 (br s, 1H), 7.46 (d, 8.4 Hz, 2H), 7.35 (d, 8.4 Hz, 2H), 4.80 (d, J=8.8 Hz, 1H), 3.93 (d, J=8.6 Hz, 1H), 2.28 (s, 3H), 1.59 (s, 3H).

Synthesis of Compound 1-7

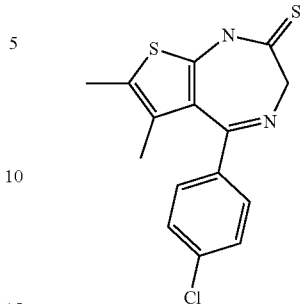

Phosphorus pentasulfide (17.07 g, 76.79 mmol, 8.17 mL, 3.60 eq) was added to a constantly stirred turbid liquor of sodium carbonate (4.07 g, 38.39 mmol, 1.80 eq) in 1,2-dichloroethane (200.00 mL). The resulting mixture was stirred at 20° C. for 1 hour. Then compound 1-6 (6.50 g, 21.33 mmol, 1.00 eq) was added. The obtained turbid liquor was reacted at 65° C. for 5 hours. The reaction mixture was cooled to 20° C. and filtered. The filter cake was dissolved in ethyl acetate (2 L) and washed with a saturated saline solution (500 mL), dried over sodium sulfate, filtered, and then concentrated under reduced pressure. The compound as a crude product was purified with a silica gel column (petroleum ether/ethyl acetate=5/1) to give compound 1-7.

Synthesis of Compound 1-8

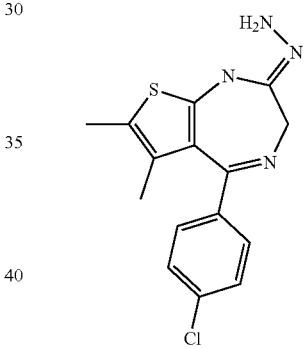

At 0° C., to a turbid liquor of compound 1-7 (3.50 g, 10.91 mmol, 1.00 eq) in methanol (5.00 mL) was added hydrazine hydrate (1.67 g, 32.72 mmol, 1.62 mL, 98% purity, 3.00 eq). The mixture was reacted under being stirred at 0° C. for 1 hour. The reaction mixture was filtered, and the filter cake was oven-dried. Compound 1-8 was obtained and directly used in the next step of the reaction. LCMS (ESI) m/z: 318.9 (M+1).

Synthesis of Compound 1-9

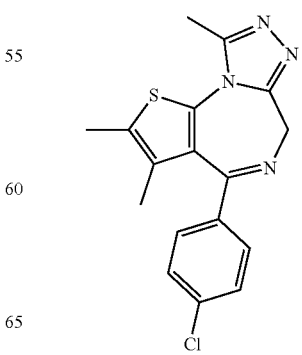

To a mixed liquor of compound 1-8 (2.50 g, 7.84 mmol, 1.00 eq) in toluene (100.00 mL) was added triethyl orthoacetate (3.82 g, 23.52 mmol, 4.29 mL, 3.00 eq). The resulting mixture was reacted under being stirred at 80° C. for 1 hour. The reaction mixture was directly concentrated under reduced pressure. The compound as a crude product was recrystallized with ethyl acetate (10 mL) to give compound 1-9. LCMS (ESI) m/z: 344.9 (M+1).

Synthesis of Compound 1-10

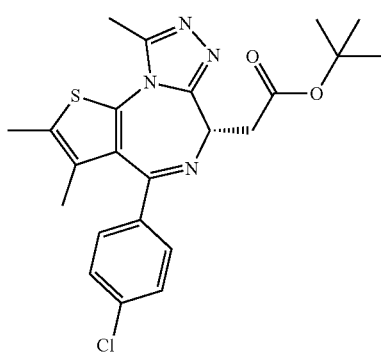 [SMILES: Cc1sc2c(c1C)C(c1ccc(Cl)cc1)=N[C@@H](CC(=O)OC(C)(C)C)c1nnc(C)n1-2]

At −70° C., to a solution of compound 1-9 (1.50 g, 4.38 mmol, 1.00 eq) in tetrahydrofuran (180 mL), was added dropwisely LiHMDS (1 M, 8.76 mL, 2.00 eq). The mixture was reacted under being stirred at the same temperature for 1 hour, and then a solution of tert-butyl 2-bromoacetate (1.28 g, 6.57 mmol, 970.82 μL, 1.50 eq) dissolved in tetrahydrofuran (20 mL) was added dropwisely. After the completion of the dropwise addition, the reaction mixture was slowly warmed up to 20° C. and stirred for 5 hours. The reaction mixture was quenched with a saturated NH4Cl solution (50 mL), extracted with ethyl acetate (100 mL) and washed with a saturated saline solution (50 mL), dried over anhydrous sodium sulfate, filtered, and then concentrated under reduced pressure. The compound as a crude product was purified with a flash chromatography column, and the obtained compound was separated with SFC to give compound 1-10 (basicity-EtOH, chromatography column: AS (250 mm×30 mm, 5 μm), mobile phase B: 30%, flow rate (mL/min): 55) ($[\alpha]^{25}_D$+54 (C 0.6, CHCl$_3$)). LCMS (ESI) m/z: 457.0 (M+1).

Synthesis of Compound 1-11

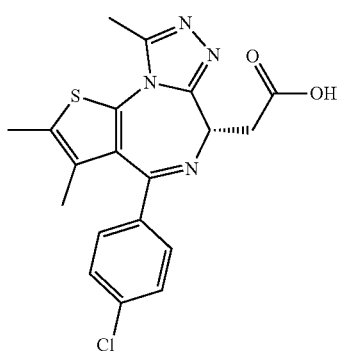 [SMILES: Cc1sc2c(c1C)C(c1ccc(Cl)cc1)=N[C@@H](CC(=O)O)c1nnc(C)n1-2]

Compound 1-10 (150.00 mg, 328.23 μmol, 1.00 eq) was dissolved in methylene chloride (5.00 mL) and trifluoroacetic acid (1.00 mL). The mixture was reacted under being stirred at 20° C. for 4 hours. The reaction mixture was directly concentrated under reduced pressure. Compound 1-11 was obtained and directly used in the next step of the reaction. LCMS (ESI) m/z: 401.0 (M+1).

Synthesis of Compound 1

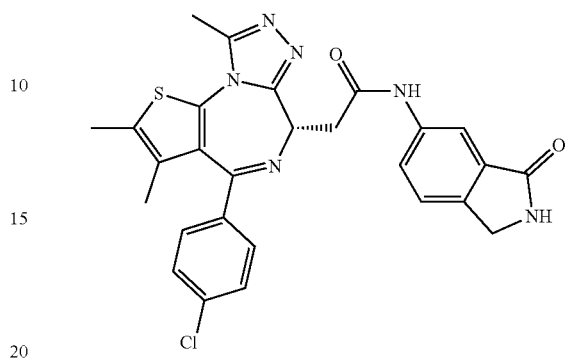

At 30° C. and under the protection of nitrogen gas, N,N-diisopropylethylamine (48.36 mg, 374.19 μmol) was slowly added dropwisely to a solution of compound 1-11 (50.00 mg, 124.73 μmol), 6-amino-isoindolin-1-one (27.72 mg, 187.10 μmol) and HATU (71.14 mg, 187.10 μmol) in anhydrous methylene chloride (15.00 mL). After the addition, the mixture was reacted at 30° C. for 12 hours. The reaction mixture was washed with water (20 mL×2). The aqueous phase was extracted with methylene chloride (20 mL). The combined organic phases were dried over anhydrous sodium sulfate, filtered, then concentrated under reduced pressure, and purified with a preparative chromatography to give compound 1. $^1$H NMR (400 MHz, CDCl$_3$): δppm 9.46 (br s, 1H), 8.03 (br s, 1H), 7.85 (d, J=7.6 Hz, 1H), 7.41 (d, J=8.4 Hz, 2H), 7.31-7.33 (m, 3H), 6.57-6.61 (m, 1H), 4.69-4.73 (m, 1H), 4.34 (s, 2H), 3.83-3.88 (m, 1H), 3.56-3.61 (m, 1H), 2.69 (s, 3H), 2.41 (s, 3H), 1.68 (s, 3H). LCMS (ESI) m/z: 531.1 (M+1).

Scheme 2

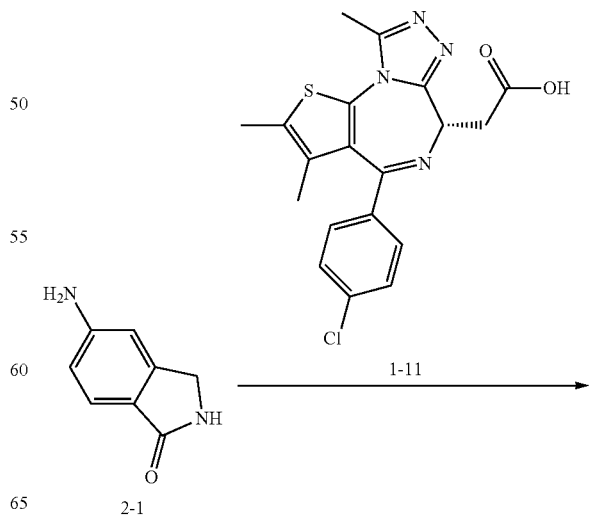

39
-continued
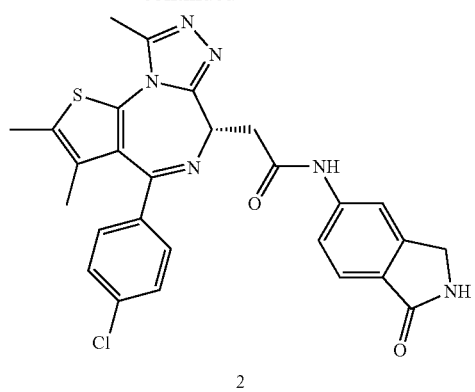
2
Example 2
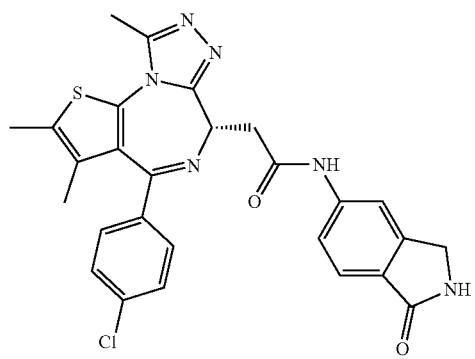 [SMILES: Cc1sc2c(c1C)C(c1ccc(Cl)cc1)=N[C@@H](CC(=O)Nc1ccc3c(c1)CNC3=O)c1nnc(C)n1-2]
Example 2 was synthesized with reference to Example 1.
$^1$H NMR (400 MHz, CDCl$_3$): δppm 9.62 (br s, 1H), 8.00 (s, 1H), 7.76 (d, J=8.4 Hz 1H), 7.34-7.45 (m, 5H), 6.14-6.15 (m, 1H), 4.65-4.68 (m, 1H), 4.38 (s, 2H), 3.85-3.91 (m, 1H), 3.50-3.54 (m, 1H), 2.71 (s, 3H), 2.44 (s, 3H), 1.72 (s, 3H). LCMS (ESI) m/z: 531.1 (M+1).
Schemes 3 and 4
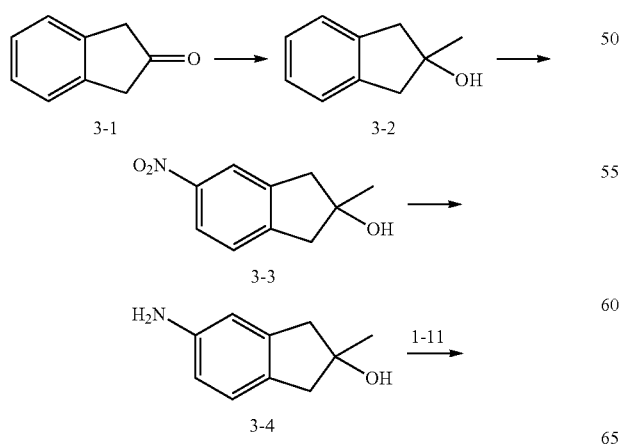
40
-continued
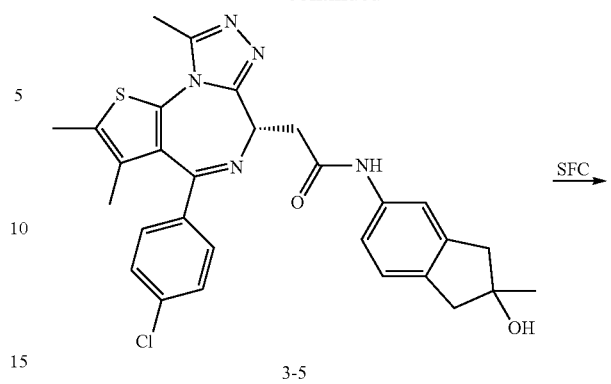
3-5
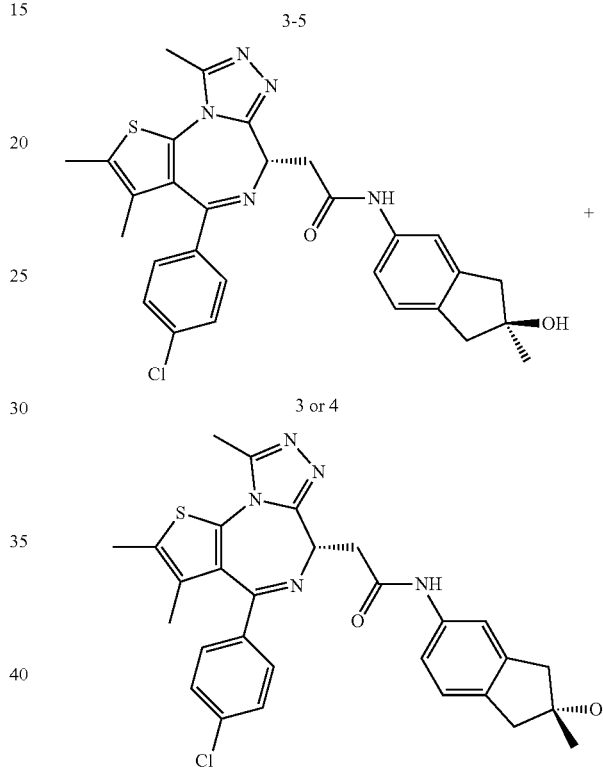
3 or 4
3 or 4
Examples 3 and 4
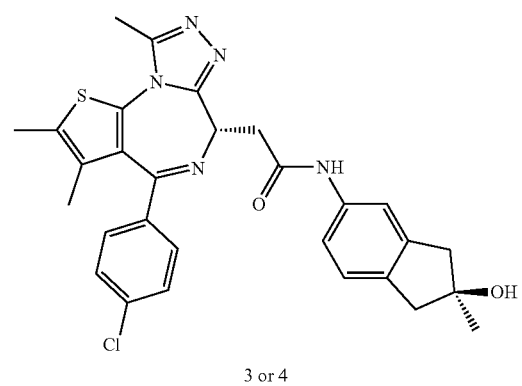
3 or 4

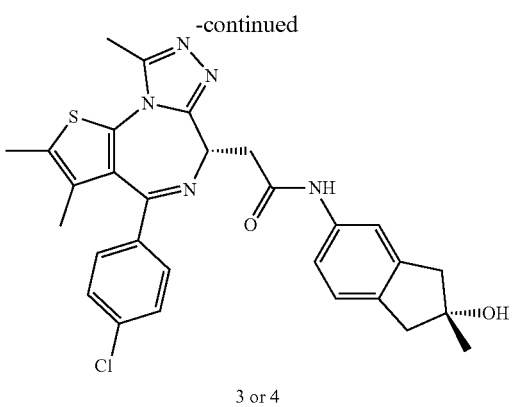

3 or 4

Synthesis of Compound 3-2

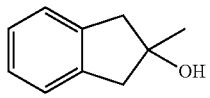

At 0° C., magnesium methyl bromide (3 M, 6.30 mL) was added to anhydrous diethyl ether (10 mL). The atmosphere was replaced with nitrogen gas three times. A solution of compound 3-1 (2.00 g, 15.13 mmol) in anhydrous diethyl ether (40 mL) was slowly added dropwisely. The mixture was stirred at 25° C. in a nitrogen atmosphere for 3 hours. The reaction mixture was poured into ice water (50 g) under being stirred. A saturated NH$_4$Cl solution (50 mL) was added and the mixture was stirred for 5 minutes. The mixture was separated into two phases. The aqueous phase was extracted with ethyl acetate (50 mL). The organic phases were combined and washed with a saturated sodium bicarbonate solution (50 mL), water (50 mL) and a saturated saline solution (80 mL) each once, dried over anhydrous sodium sulfate, filtered and concentrated under reduced pressure. The crude product was purified with a flash chromatography column to give compound 3-2. $^1$H NMR (400 MHz, CDCl$_3$): δppm 7.14-7.23 (m, 4H), 2.97-3.08 (m, 4H), 1.52 (s, 3H).

Synthesis of Compound 3-3

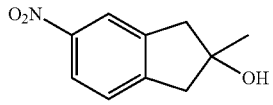

At 0° C. and under being stirred, a solution of compound 3-2 (200.00 mg, 1.35 mmol) in methylene chloride (2 mL) was slowly added to a solution of concentrated nitric acid (4.20 g, 66.66 mmol, 3.00 mL) and concentrated sulphuric acid (132.36 mg, 1.35 mmol) in anhydrous methylene chloride (10 mL). The mixture was stirred at 0° C. for 5 minutes. The reaction mixture was slowly poured into crushed ice (50 g) under being stirred. The mixture was stirred for 10 minutes and separated into two phases. The aqueous phase was extracted with methylene chloride (30 mL×2). The combined organic phases were washed with a saturated sodium bicarbonate solution (80 mL) and a saturated saline solution (80 mL) respectively, dried over anhydrous sodium sulfate, filtered and concentrated under reduced pressure. The crude product was purified with a thin-layer chromatography plate to give compound 3-3. $^1$H NMR (400 MHz, CDCl$_3$): δppm 8.04-8.14 (m, 2H), 7.32-7.38 (m, 1H), 3.53-3.57 (m, 2H), 3.28-3.33 (m, 2H), 1.81 (s, 3H).

Synthesis of Compound 3-4

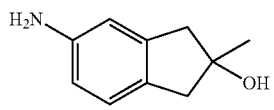

Compound 3-3 (220.00 mg, 1.14 mmol) and Pd/C (200.00 mg, 10% purity) were added to absolute methanol (10.00 mL). The atmosphere was replaced with hydrogen gas three times. The mixture was stirred for 16 hours at 25° C. under a hydrogen balloon atmosphere. The reaction mixture was directly filtered through a pad of celite with a Buchner funnel and concentrated under reduced pressure. The crude product was purified with a thin-layer chromatography plate to give compound 3-4.

Synthesis of Compound 3-5

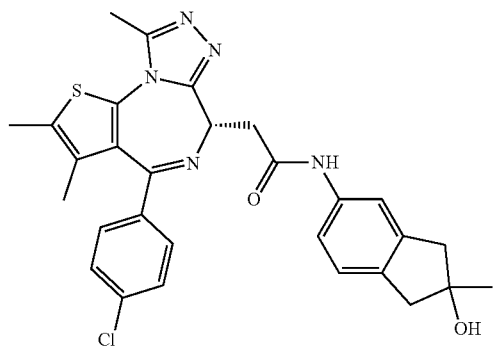

Compound 3-4 (46.00 mg, 281.83 μmol, 1.20 eq) and diisopropylethylamine (91.06 mg, 704.58 μmol, 123.05 μL, 3.00 eq) were added to methylene chloride (5.00 mL). Compound 1-11 (94.15 mg, 234.86 μmol, 1.00 eq) and HATU (89.30 mg, 234.86 μmol, 1.00 eq) were added. The atmosphere was replaced with nitrogen gas three times. The mixture was stirred at 25° C. in a nitrogen atmosphere for 2 hours. The reaction mixture was shaking washed with water (10 mL). The organic phase was washed with a saturated saline solution (20 mL), dried over anhydrous sodium sulfate, filtered and concentrated under reduced pressure. The crude product was purified with a thin-layer chromatography plate to give compound 3-5. LCMS (ESI) m/z: 546.2 (M+1).

Synthesis of Compounds 3 and 4

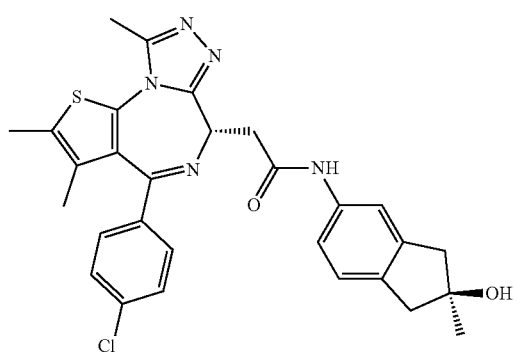

3 or 4

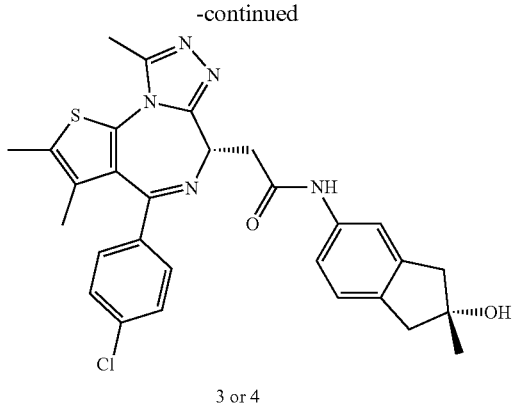

3 or 4

Compound 3-5 (98 mg, 179.46 μmol) was subjected to a SFC chiral resolution (chromatography column: AD (250 mm×30 mm, 10 μm); mobile phase: [0.1% NH₃H₂O EtOH]; B %: 40%-40%, 60 mL/min) to give two products, each having a single configuration. Example 3 (Rt=5.311 min). ¹H NMR (400 MHz, CDCl₃): δppm 8.68 (s, 1H), 7.51 (s, 1H), 7.41 (d, J=8.4 Hz, 2H), 7.33 (d, J=8.8 Hz, 2H), 7.28-7.29 (m, 1H), 7.12 (d, J=8.0 Hz, 1H), 4.60-4.64 (m, 1H), 3.74-3.80 (m, 1H), 3.44-3.49 (m, 1H), 2.95-3.03 (m, 4H), 2.68 (s, 3H), 2.40 (s, 3H), 1.68 (s, 3H), 1.49 (s, 3H). LCMS (ESI) m/z: 546.2 (M+1).

Example 4 (Rt=5.926 min) ¹H NMR (400 MHz, CDCl₃): δppm 8.72 (s, 1H), 7.51 (s, 1H), 7.41 (d, J=8.4 Hz, 2H), 7.33 (d, J=8.8 Hz, 2H), 7.28-7.29 (m, 1H), 7.12 (d, J=8.0 Hz, 1H), 4.60-4.64 (m, 1H), 3.74-3.80 (m, 1H), 3.44-3.49 (m, 1H), 2.95-3.03 (m, 4H), 2.68 (s, 3H), 2.40 (s, 3H), 1.68 (s, 3H), 1.49 (s, 3H). LCMS (ESI) m/z: 546.1 (M+1).

Scheme 5

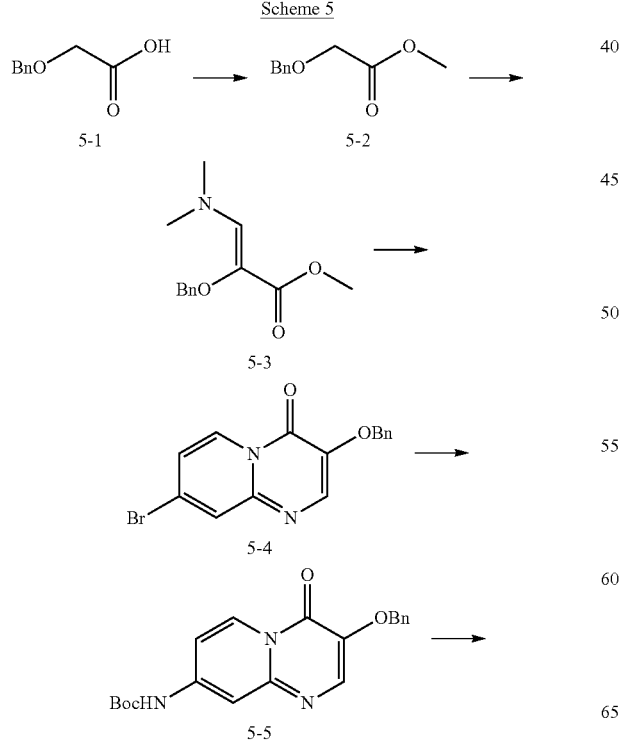

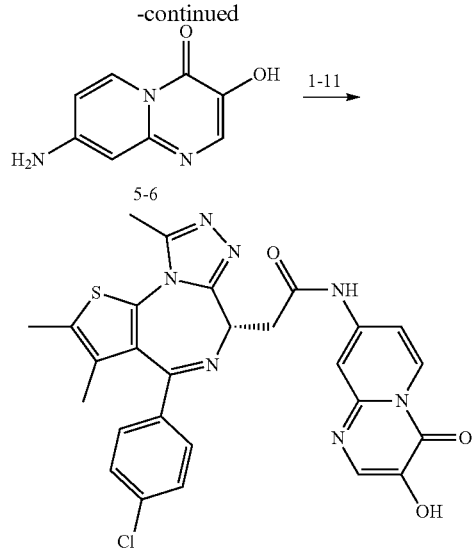

Example 5

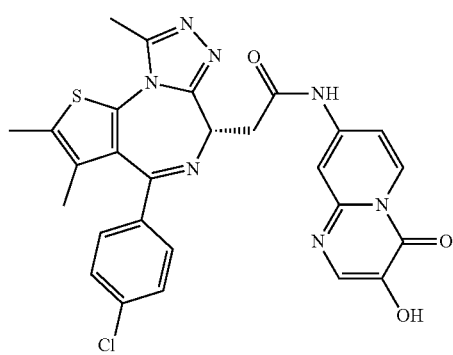 [SMILES: Cc1sc2c(c1C)C(c1ccc(Cl)cc1)=N[C@@H](CC(=O)Nc1ccn3c(=O)c(O)cnc3c1)c1nnc(C)n1-2]

Synthesis of Compound 5-2

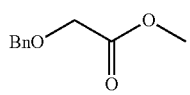

At 0° C., thionyl chloride (25.77 g, 216.65 mmol, 15.71 mL, 1.20 eq) was added dropwisely to methanol (200.00 mL). The mixture was stirred at 0° C. for 30 minutes. A solution of compound 5-1 (30.00 g, 180.54 mmol, 25.86 mL, 1.00 eq) in methanol (100.00 mL) was added dropwisely. After the completion of the dropwise addition, the mixture was reacted at 26° C. for 4 hours. The reaction mixture was concentrated under reduced pressure. The residue was dissolved in methylene chloride. The mixture was adjusted with a saturated sodium carbonate solution to pH=8-9, extracted, and separated into two phases. The organic phase was dried over anhydrous sodium sulfate and filtered. The filtrate was concentrated under reduced pressure to give compound 5-2, which was directly used in the next step without any further purification. ¹H NMR (400 MHz, CDCl₃): δppm 7.26-7.37 (m, 5H), 4.63 (s, 2H), 4.11 (s, 2H), 3.76 (s, 3H).

Synthesis of Compound 5-3

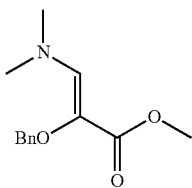

A mixture of compound 5-2 (16.00 g, 88.79 mmol, 1.00 eq) and tert-butoxy di(dimethylamino)methane (17.02 g, 97.67 mmol, 20.26 mL, 1.10 eq) was heated to 90° C. and reacted for 16 hours. The reaction mixture was concentrated under reduced pressure. The residue was dissolved in methylene chloride (80 mL). The mixture was washed with a saturated saline solution (25 mL), extracted, and separated into two phases. The organic phase was dried over anhydrous sodium sulfate and filtered. The filtrate was concentrated under reduced pressure to give compound 5-3, which was directly used in the next step without any further purification. $^1$H NMR (400 MHz, CDCl$_3$): δppm 7.26-7.33 (m, 5H), 6.78 (s, 1H), 4.63 (s, 2H), 3.64 (s, 3H), 2.88 (m, 6H).

Synthesis of Compound 5-4

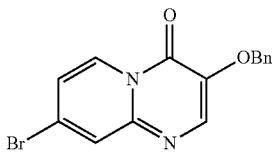

Glacial acetic acid (40.00 mL) was added to a mixture of compound 5-3 (12.00 g, 51.00 mmol, 1.00 eq) and 4-bromo-2-aminopyridine (8.82 g, 51.00 mmol, 1.00 eq). The resulting mixture was heated to 130° C. and stirred for 16 hours. The reaction mixture was concentrated under reduced pressure. The obtained residue was purified with column chromatography (petroleum ether:ethyl acetate=4:1) to give compound 5-4. $^1$H NMR (400 MHz, CDCl$_3$): δppm 8.72 (d, J=7.6 Hz, 1H), 8.19 (s, 1H), 7.89 (s, 1H), 7.35-7.47 (m, 5H), 5.19 (s, 2H).

Synthesis of Compound 5-5

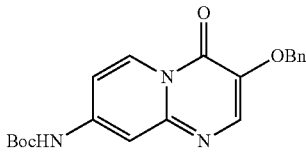 [SMILES: CC(C)(C)OC(=O)Nc1ccn2c(=O)c(OCc3ccccc3)cnc2c1]

To a solution of compound 5-4 (1.00 g, 3.02 mmol, 1.00 eq) and tert-butyl carbamate (459.88 mg, 3.93 mmol, 1.30 eq) in 1,4-dioxane (20.00 mL) were successively added 4,5-bis(diphenylphosphine)-9,9-dimethylxanthene (174.73 mg, 301.97 μmol, 0.10 eq), tris(dibenzylideneacetone) dipalladium (276.52 mg, 301.97 μmol, 0.10 eq) and cesium carbonate (2.95 g, 9.06 mmol, 3.00 eq). The atmosphere was replaced with nitrogen gas three times. The mixture was heated to 100° C. under the protection of nitrogen gas and reacted for 10 hours. The reaction mixture was cooled to room temperature and filtered. The filter cake was washed with methylene chloride (10 mL×2). The resulting filtrate was concentrated under reduced pressure. The obtained residue was purified with column chromatography (petroleum ether:ethyl acetate=5:1-2:1) to give compound 5-5. LCMS (ESI) m/z: 368.2 (M+1).

Synthesis of Compound 5-6

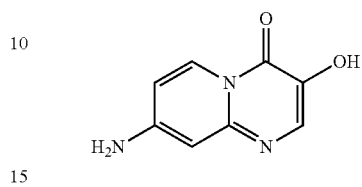

A mixture of compound 5-5 (190.00 mg, 517.15 μmol, 1.00 eq) and trifluoroacetic acid (5.00 mL) was heated to 90° C. and stirred for 20 hours. The reaction mixture was concentrated under reduced pressure. The resulting residue was dissolved in methylene chloride (10 mL). The mixture was again concentrated under reduced pressure to give compound 5-6, which was directly used in the next step without any further purification.

Synthesis of Compound 5

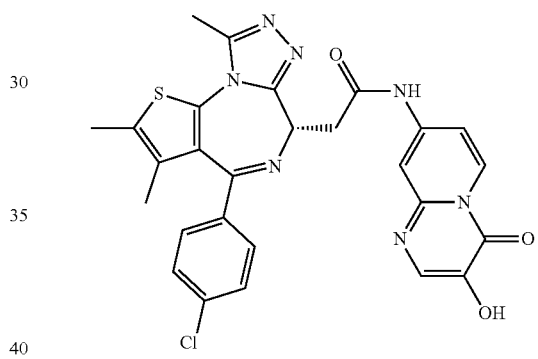

At −10° C. and under the protection of nitrogen gas compound 1-11 (60.00 mg, 149.67 μmol, 1.00 eq) and triethylamine (30.29 mg, 299.34 μmol, 41.49 μL, 2.00 eq) were dissolved in a mixed liquor of anhydrous tetrahydrofuran (2.00 mL) and anhydrous N,N-dimethyl formamide (1.00 mL). Then pivaloyl chloride (18.05 mg, 149.67 μmol, 18.42 μL, 1.00 eq) was slowly added dropwise to the above solution. The resulting mixture was stirred at −10° C. for 0.5 hour. Then a solution of compound 5-6 (40.00 mg, 137.37 μmol, 0.92 eq, TFA) in anhydrous N,N-dimethyl formamide (1.00 mL) was added dropwisely to the reaction mixture. After the completion of the dropwise addition, the mixture was warmed up to 27° C. and stirred for 5 hours. The reaction mixture was quenched with water (5 mL), and the mixture was separated into two phases. The aqueous phase was extracted with methylene chloride (5 mL×3). The organic phases were combined. The combined organic phases were washed with a saturated saline solution (10 mL), dried over anhydrous sodium sulfate and filtered. The filtrate was concentrated under reduced pressure. The obtained crude product was purified with a preparative chromatography (basicity) to give compound 5. $^1$H NMR (400 MHz, CDCl$_3$): δppm 8.76 (d, J=7.28 Hz, 1H), 8.12 (s, 1H), 7.47 (d, J=8.28 Hz, 2H), 7.34 (d, J=8.53 Hz, 3H), 6.56-6.64 (m, 2H), 5.12 (s, 1H), 4.72 (t, J=7.15 Hz, 1H), 3.93-4.00 (m, 2H), 2.69 (s, 3H), 2.40 (s, 3H), 1.68 (s, 3H).
LCMS (ESI) m/z: 560.0 (M+1).

Examples 6 and 7

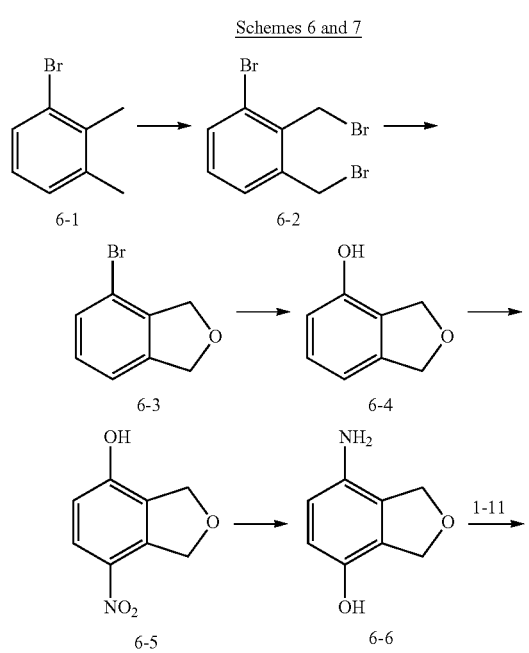

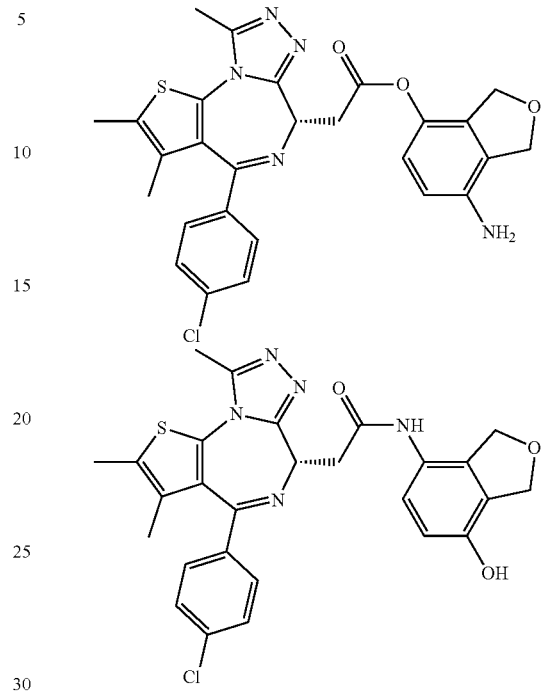

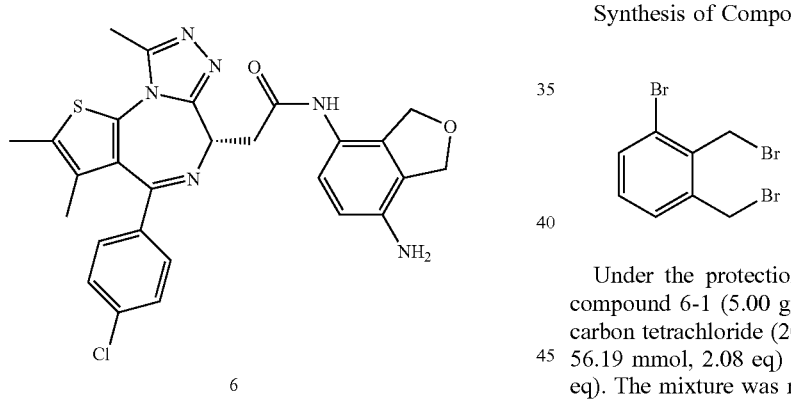

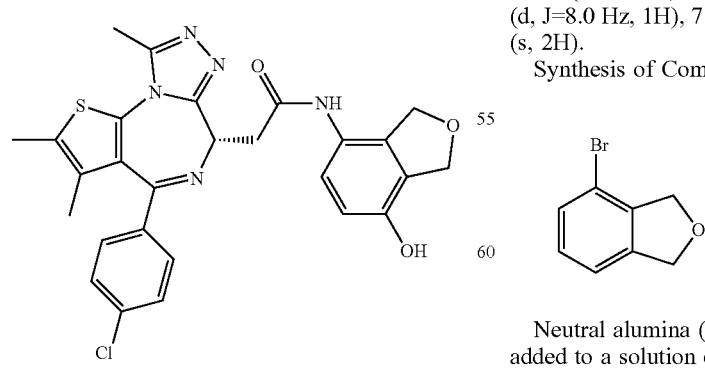

Synthesis of Compound 6-2

Under the protection of nitrogen gas, to a solution of compound 6-1 (5.00 g, 27.02 mmol, 3.65 mL, 1.00 eq) in carbon tetrachloride (20.00 mL) were added NBS (10.00 g, 56.19 mmol, 2.08 eq) and AIBN (1.04 g, 6.33 mmol, 0.23 eq). The mixture was reacted under being stirred at 65° C. for 4 hours. The reaction mixture was directly concentrated under reduced pressure. The crude product was purified with a flash chromatography column to give compound 6-2. $^1$H NMR (400 MHz, CDCl$_3$) δppm 7.57 (d, J=8.0 Hz, 1H), 7.32 (d, J=8.0 Hz, 1H), 7.16 (t, J=7.8 Hz, 1H), 4.84 (s, 2H), 4.63 (s, 2H).

Synthesis of Compound 6-3

Neutral alumina (100.00 g, 980.78 mmol, 93.41 eq) was added to a solution of compound 6-2 (3.60 g, 10.50 mmol, 1.00 eq) dissolved in n-hexane (200.00 mL), and the mixture was reacted under being stirred at 75° C. for 2 hours. The reaction mixture was directly filtered. The filter cake was washed with ethyl acetate (200 mL). The filtrate was directly concentrated under reduced pressure. The compound as a crude product was purified with a flash chromatography column to give compound 6-3. ¹H NMR (400 MHz, CDCl₃): δppm 7.38-7.40 (m, 1H), 7.16-7.16 (m, 2H), 5.21 (s, 2H), 5.10 (s, 2H).

Synthesis of Compound 6-4

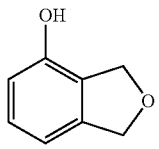

To a mixed liquor of compound 6-3 (400.00 mg, 2.01 mmol, 1.00 eq), potassium hydroxide (225.52 mg, 4.02 mmol, 2.00 eq) and 2-di-tert-butylphosphine-2',4',6'-triisopropylbiphenyl (85.34 mg, 201.00 μmol, 0.10 eq) in 1,4-dioxane (10.00 mL) were added water (1.00 mL) and tris(dibenzylideneacetone) dipalladium (184.03 mg, 201.00 μmol, 0.10 eq). The mixture was reacted at 120° C. under the protection of nitrogen gas in a microwave instrument for 1 hour. The reaction mixture was directly concentrated under reduced pressure. The residue was dissolved in ethyl acetate (20 mL). The mixture was washed with water (10 mL) and a saturated saline solution (10 mL), dried over anhydrous sodium sulfate, filtered, and then concentrated under reduced pressure. The compound as a crude product was purified with the preparative plate (petroleum ether/ethyl acetate=5/1) to give compound 6-4. ¹H NMR (400 MHz, CDCl₃-d) δppm 7.15 (t, J=7.6 Hz, 1H), 6.80 (d, J=7.6 Hz, 1H), 6.66 (d, J=7.6 Hz, 1H), 5.15 (m, 4H).

Synthesis of Compound 6-5

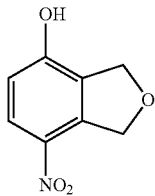

At −5° C. and under the protection of nitrogen gas, concentrated sulphuric acid (36.75 mg, 367.24 μmol, 19.97 μL, 98% purity, 1.00 eq) was added to a solution of compound 6-4 (50.00 mg, 367.24 μmol, 1.00 eq) dissolved in methylene chloride (2 mL). Then fuming nitric acid (24.36 mg, 367.24 μmol, 17.40 μL, 1.00 eq) (purity 95%) diluted in methylene chloride (0.5 mL) was slowly added to the reaction mixture. The resulting mixture was stirred for 0.5 hour. The reaction mixture was diluted with methylene chloride (10 mL), then washed with water (5 mL) and a saturated saline solution (5 mL), dried over anhydrous sodium sulfate, filtered, and then concentrated under reduced pressure. The compound as a crude product was purified with a preparative plate (petroleum ether/ethyl acetate=3/1) to give compound 6-5. ¹H NMR (400 MHz, CDCl₃) δppm 7.94 (d, J=8.8 Hz, 1H), 6.72 (d, J=8.8 Hz, 1H), 5.32 (s, 2H), 4.97 (s, 2H).

Synthesis of Compound 6-6

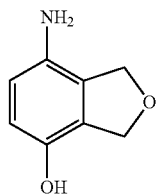 [SMILES: Nc1ccc(O)c2c1COC2]

Under the protection of nitrogen gas, to a solution of compound 6-5 (40.00 mg, 220.81 μmol, 1.00 eq) dissolved in methanol (10.00 mL) was added Pd/C (100.00 mg) (containing palladium 20%, water 50%). Then the atmosphere of the reaction system was replaced with hydrogen gas three times. The reaction mixture was reacted at 20° C. under a hydrogen balloon (15 psi) for 1 hour. The reaction mixture was directly filtered. The filter cake was washed with methanol (10 mL). The filtrate was directly concentrated under reduced pressure to give compound 6-6, which was directly used in the next step of the reaction. LCMS (ESI) m/z: 151.9 (M+1).

Synthesis of Compounds 6 and 7

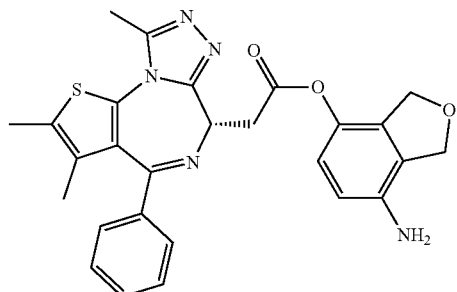

6

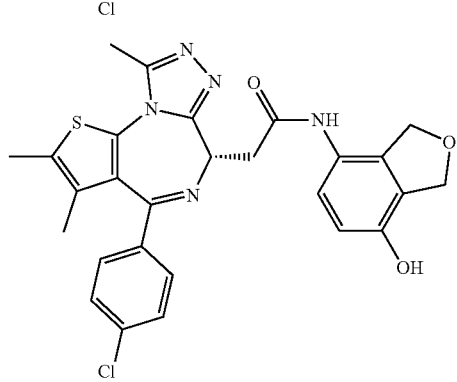

7

Compound 1-11 (50.00 mg, 124.73 μmol, 1.00 eq), compound 6-6 (30.00 mg, 198.32 μmol, 1.59 eq), triethylamine (37.86 mg, 374.19 μmol, 51.86 μL, 3.00 eq) and HATU (71.14 mg, 187.10 μmol, 1.50 eq) were dissolved in methylene chloride (5.00 mL). The mixture was stirred at 20° C. under the protection of nitrogen gas for 2 hours. The reaction mixture was diluted with methylene chloride (10 mL) and washed with water (10 mL) and a saturated saline solution (10 mL). The organic phase was dried over anhydrous sodium sulfate, filtered, and then concentrated under reduced pressure. The compound as a crude product was purified with a preparative plate to give compound 6. LCMS (ESI) m/z: 534.1 (M+1). ¹H NMR (400 MHz, CDCl₃) δppm 8.47 (s, 1H), 7.36 (d, J=8.0 Hz, 2H), 7.28 (d, J=8.4 Hz, 2H), 7.07 (d, J=8.4 Hz, 1H), 6.57 (d, J=8.0 Hz, 1H), 4.85-5.00 (m, 4H), 4.53-4.56 (m, 1H), 3.63-3.65 (m, 1H), 3.34-3.38 (m, 1H), 2.62 (s, 3H), 2.34 (s, 3H), 1.62 (s, 3H).

Compound 7. LCMS (ESI) m/z: 534.1 (M+1). $^1$H NMR (400 MHz, CDCl$_3$) δppm 8.65 (s, 1H), 8.57 (br s, 1H), 7.35 (d, J=8.4 Hz, 2H), 7.26 (d, J=8.4 Hz, 2H), 6.90 (d, J=8.0 Hz, 1H), 6.53 (d, J=8.8 Hz, 1H), 4.95 (s, 2H), 4.90 (d, J=12.8 Hz, 1H), 4.80 (d, J=12.8 Hz, 1H), 4.57-4.60 (m, 1H), 3.63-3.69 (m, 1H), 3.35-3.39 (m, 1H), 2.62 (s, 3H), 2.34 (s, 3H), 1.61 (s, 3H).

Scheme 8

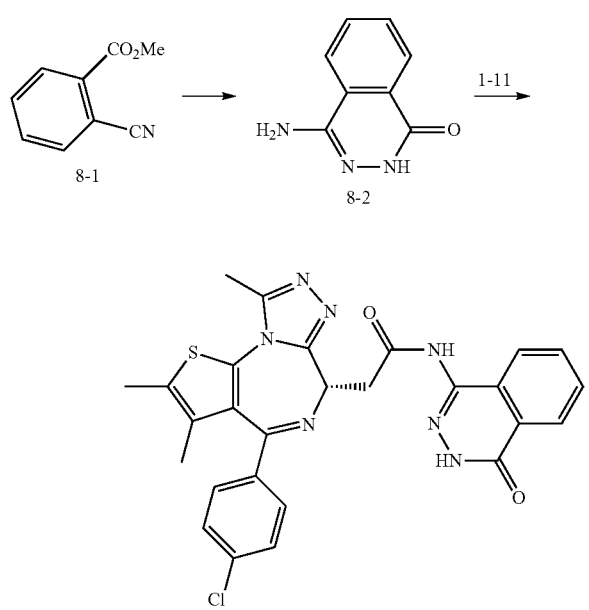

Example 8

Synthesis of Compound 8-2

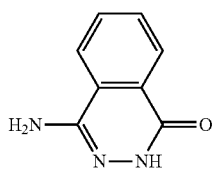

Compound 8-1 (500.00 mg, 3.10 mmol, 1.00 eq) and hydrazine hydrate (4.12 g, 80.66 mmol, 4.00 mL, 26.02 eq) were added to a microwave tube. The mixture was reacted in the microwave at 90° C. for 1 hour. A large amount of solid precipitated from the reaction mixture. The reaction was terminated. The reaction mixture was filtered. The filter cake was washed with water (20 mL×2). Then anhydrous tetrahydrofuran (20 mL×2) was added. The mixture was concentrated under reduced pressure to give compound 8-2 without any further purification. LCMS (ESI) m/z: 161.9 (M+1).

Synthesis of Compound 8

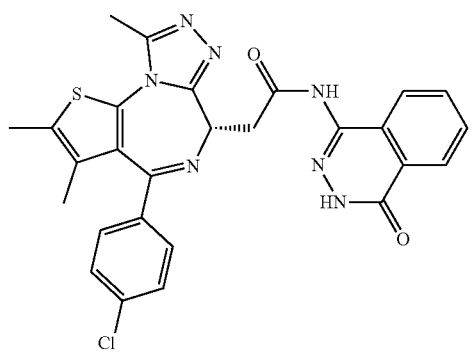 [SMILES: Cc1sc2c(c1C)C(c1ccc(Cl)cc1)=N[C@@H](CC(=O)Nc1n[nH]c(=O)c3ccccc13)c1nnc(C)n1-2]

A solution of compound 1-11 (100.00 mg, 249.45 μmol, 1.00 eq) and compound 8-2 (100.50 mg, 623.63 μmol, 2.50 eq) in pyridine (5.00 mL) was added dropwisely to POCl$_3$ (114.74 mg, 748.35 μmol, 69.54 μL, 3.00 eq). The mixture was reacted under being stirred at 20° C. for 12 hours. The reaction mixture was diluted with ethyl acetate (10 mL) and washed with water (5 mL×2) and a saturated saline solution (5 mL), dried over anhydrous sodium sulfate, filtered and concentrated under reduced pressure. The compound as a crude product was purified with a preparative chromatography to give compound 8. $^1$H NMR (400 MHz, CDCl$_3$) δppm 10.49-10.54 (m, 1H), 9.84 (br s, 1H), 8.36-8.37 (m, 1H), 7.79-7.98 (m, 1H), 7.72-7.74 (m, 2H), 7.46 (d, J=8.4 Hz, 2H), 7.34 (d, J=8.4 Hz, 2H), 4.70-4.73 (m, 1H), 3.73-3.86 (m, 2H), 2.68 (s, 3H), 2.40 (s, 3H), 1.67 (s, 3H). LCMS (ESI) m/z: 544.1 (M+1).

Scheme 9

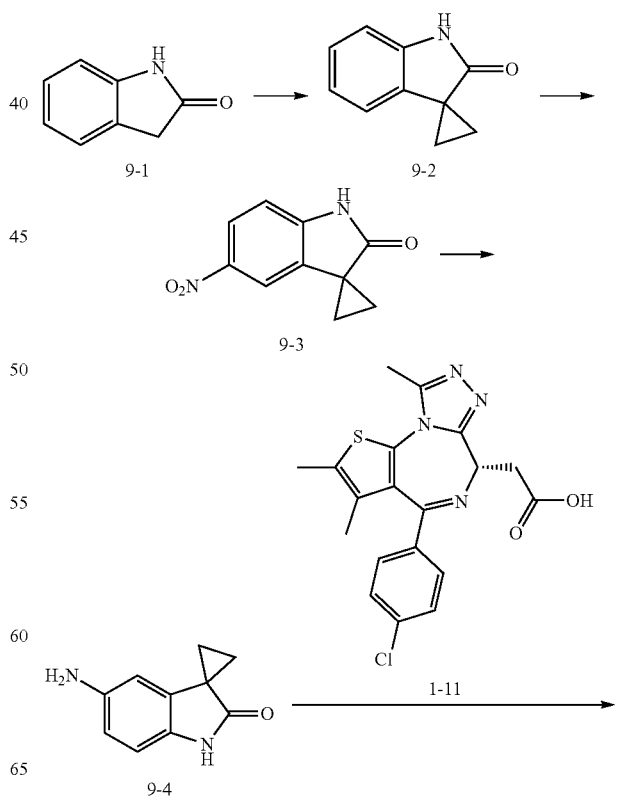

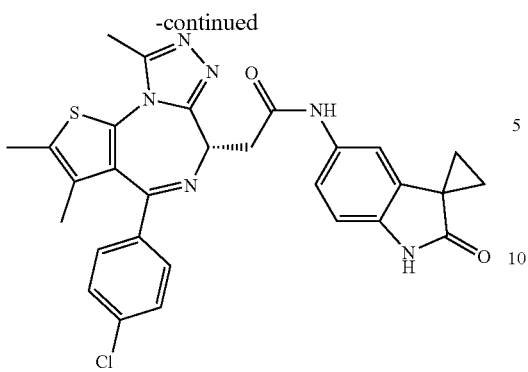

9

Example 9

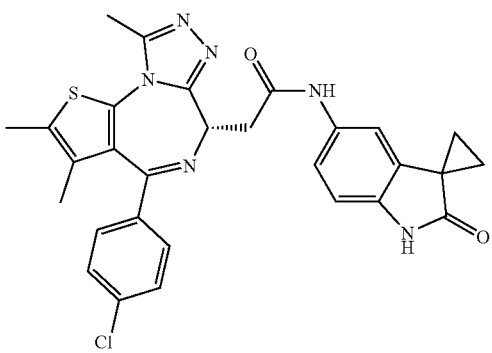 [SMILES: Cc1sc2c(c1C)C(c1ccc(Cl)cc1)=N[C@@H](CC(=O)Nc1ccc3c(c1)C1(CC1)C(=O)N3)c1nnc(C)n1-2]

Synthesis of Compound 9-2

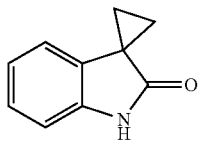 [SMILES: O=C1Nc2ccccc2C12CC2]

At −20° C. and under the protection of nitrogen gas, compound 9-1 (2.00 g, 15.02 mmol, 1.00 eq) and anhydrous diisopropylamine (3.16 g, 31.24 mmol, 4.39 mL, 2.08 eq) were dissolved in anhydrous tetrahydrofuran (30.00 mL). After the solution was cooled to −20° C., n-butyl lithium (2.5 M, 23.73 mL, 3.95 eq) was slowly added dropwisely, and the resulting mixture was maintained at a temperature between −20 and −30° C. After the completion of the dropwise addition, the mixture was warmed up to 0° C. and reacted under being stirred for 1 hour. Then a solution of 1,2-dibromoethane (9.62 g, 51.22 mmol, 3.86 mL, 3.41 eq) in anhydrous tetrahydrofuran (10.00 mL) was slowly added dropwisely. After the completion of the dropwise addition, the mixture was warmed up to 27° C. and reacted under being stirred for 18 hours. At −20° C., a saturated ammonium chloride solution (20 mL) was added to quench the reaction. The reaction mixture was adjusted with 3N hydrochloric acid (5 mL) to pH=2-3, and then extracted with ethyl acetate (3×20 mL). The above organic phases were combined and washed with a saturated sodium bicarbonate solution (50 mL) and a saturated saline solution (50 mL) successively. The obtained organic phase was dried over anhydrous sodium sulfate and filtered. The filtrate was concentrated under reduced pressure to give a purple solid. The crude product was purified with a flash chromatography column to give compound 9-2. $^1$H NMR (400 MHz, CDCl$_3$): δppm 9.12 (s, 1H), 7.11 (m, 1H), 6.89-6.96 (m, 2H), 6.75 (d, J=7.28 Hz, 1H), 1.70 (t, J=4.0 Hz, 2H), 1.47 (t, J=4.0 Hz, 2H).

Synthesis of Compound 9-3

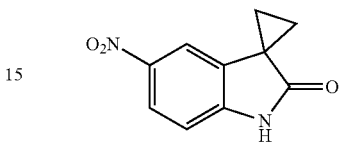

At −15° C. and under the protection of nitrogen gas, nitric acid (118.46 mg, 1.88 mmol, 84.61 μL, 1.00 eq) was slowly added dropwisely to a solution of compound 9-2 (300.00 mg, 1.88 mmol, 1.00 eq) and concentrated sulphuric acid (184.85 mg, 1.88 mmol, 100.46 μL, 1.00 eq) in methylene chloride (4.00 mL). After the completion of the dropwise addition, the mixture was warmed up to 27° C. and the stirring was kept on for 10 hours. Ice (about 2 g) was added to the reaction mixture to quench the reaction. The reaction mixture was extracted with methylene chloride (3×5 mL). The above organic phases were combined. The organic phase was washed with a saturated sodium bicarbonate solution (10 mL) and a saturated saline solution (10 mL), then dried over anhydrous sodium sulfate and filtered. The filtrate was concentrated under reduced pressure. The crude product was purified with a thin-layer chromatography plate to give compound 9-3. $^1$H NMR (400 MHz, CDCl$_3$) δppm 8.32 (s, 1H), 8.12 (m, 1H), 7.67 (d, J=2.0 Hz, 1H), 6.97 (d, J=8.4 Hz, 1H), 1.81-1.84 (m, 2H), 1.61-1.68 (m, 2H).

Synthesis of Compound 9-4

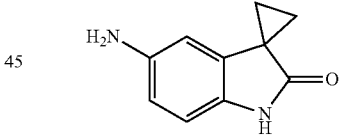

Reduced iron powder (462.27 mg, 8.28 mmol, 13.00 eq) was added to a solution of compound 9-3 (130 mg, 636.69 μmol, 1.0 eq) in glacial acetic acid (8.00 mL). The mixture was stirred at 25° C. under the protection of nitrogen gas for 16 hours. The reaction mixture was filtered. The filtrate was concentrated and then added to water (5 mL). The aqueous phase was extracted with ethyl acetate (3×5 mL). The combined organic phases were washed with a saturated saline solution (10 mL), dried over anhydrous sodium sulfate and filtered. The filtrate was concentrated under reduced pressure. The reaction mixture was filtered with diatomaceous earth. The filtrate was concentrated under reduced pressure. The obtained crude product was separated and purified with a thin-layer chromatography plate to give compound 9-4. $^1$H NMR (400 MHz, CDCl$_3$) δppm 8.37 (s, 1H), 6.75 (d, J=8.0 Hz, 1H), 6.48-6.63 (m, 1H), 6.23 (s, 1H), 1.64-1.82 (m, 2H), 1.40-1.51 (m, 2H).

Synthesis of Compound 9

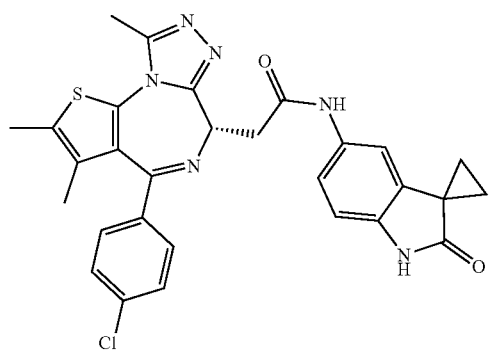 [SMILES: Cc1sc2c(c1C)C(c1ccc(Cl)cc1)=N[C@@H](CC(=O)Nc1ccc3c(c1)C1(CC1)C(=O)N3)c1nnc(C)n1-2]

At 25° C. and under the protection of nitrogen gas, compound 1-11 (36.82 mg, 91.85 μmol, 1.00 eq) and compound 9-4 (16.00 mg, 91.85 μmol, 1.00 eq) were added to a solution of HATU (41.91 mg, 110.22 μmol, 1.20 eq) in anhydrous methylene chloride (4.00 mL), and then triethylamine (27.88 mg, 275.55 μmol, 38.19 μL, 3.00 eq) was slowly added dropwisely. The mixture was stirred at 25° C. under the protection of nitrogen gas for 5 hours. Water (3 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (2 mL) and a saturated saline solution (2 mL), then dried over anhydrous sodium sulfate and filtered. The filtrate was concentrated under reduced pressure. The obtained crude product was purified with a preparative chromatography (basicity) to give compound 9. $^1$H NMR (400 MHz, CDCl$_3$) δ ppm 9.19 (s, 1H), 8.64 (s, 1H), 7.31-7.37 (m, 2H), 7.23-7.27 (m, 2H), 7.19 (s, 1H), 7.08-7.11 (m, 1H), 6.76 (d, J=8.4 Hz, 1H), 4.60-4.64 (m, 1H), 3.73-3.79 (m, 1H), 3.39-3.44 (m, 1H), 2.61 (s, 3H), 2.34 (s, 3H), 1.62-1.64 (m, 2H), 1.61 (s, 3H), 1.42-1.43 (m, 2H). LCMS (ESI) m/z: 557.1 (M+1).

Scheme 10

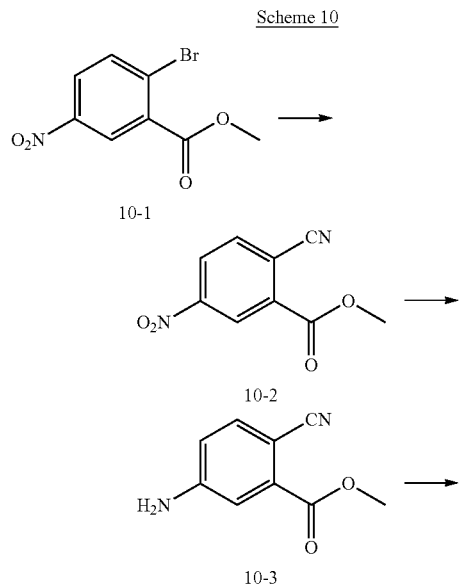

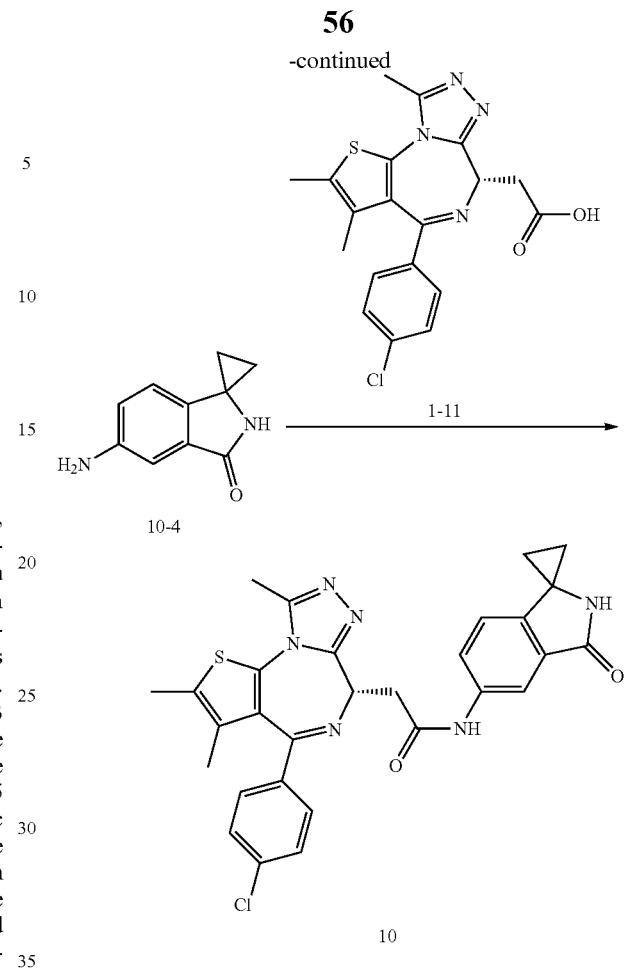

Example 10

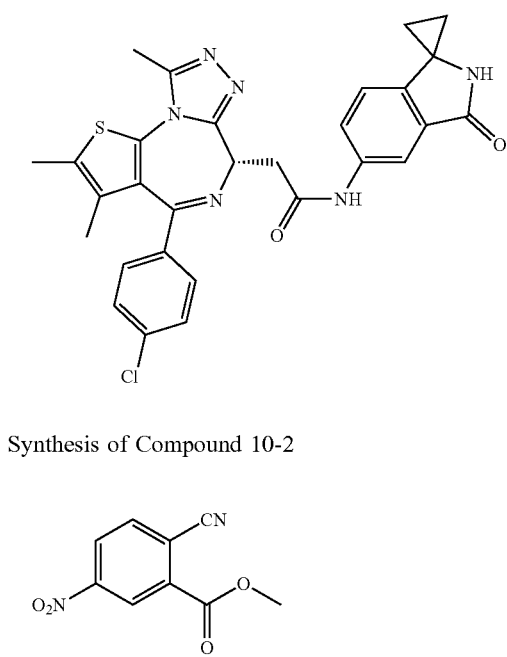

Synthesis of Compound 10-2

A mixed liquor of compound 10-1 (1.76 g, 6.77 mmol, 1.00 eq), cuprous cyanide (910.00 mg, 10.16 mmol, 2.22 mL, 1.50 eq), dppf (375.32 mg, 677.00 μmol, 0.10 eq), bis(dibenzylideneacetone) palladium (389.28 mg, 677.00 μmol, 0.10 eq) and N,N-dimethyl formamide (20.00 mL) was heated to 110° C. and stirred for 16 hours. The reaction mixture was filtered under reduced pressure. The filtrate was concentrated under reduced pressure. The concentrated residue was purified with a silica gel column (petroleum ether/ethyl acetate=1/0-3/1) to give compound 10-2. $^1$H NMR (400 MHz, CDCl$_3$) δ ppm 8.98 (d, J=2.3 Hz, 1H), 8.52 (dd, 8.5 Hz, 1H), 8.05 (d, J=8.3 Hz, 1H), 4.09 (s, 3H).

Synthesis of Compound 10-3

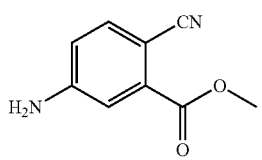

A solution of compound 10-2 (700.00 mg, 3.40 mmol, 1.00 eq) in glacial acetic acid (10.00 mL) was added to reduced iron powder (1.90 g, 34.00 mmol, 10.00 eq). The obtained reaction mixture was stirred at 20° C. for 16 hours. The reaction mixture was filtered with diatomaceous earth, and concentrated under reduced pressure. To the concentrated residue were added ethyl acetate (100 mL) and a saturated aqueous sodium bicarbonate solution (pH 7-8). The organic phase was washed with a saturated saline solution (60 mL), dried over anhydrous sodium sulfate, and concentrated under reduced pressure. The concentrated residue was purified with a silica gel column (petroleum ether/ethyl acetate=1/0-1/1) to give compound 10-3. $^1$H NMR (400 MHz, CDCl$_3$) δ ppm 7.47 (d, J=8.3 Hz, 1H), 7.26 (d, J=2.5 Hz, 1H), 6.73 (dd, J=2.5, 8.3 Hz, 1H), 4.21 (br s, 2H), 3.90 (s, 3H).

Synthesis of Compound 10-4

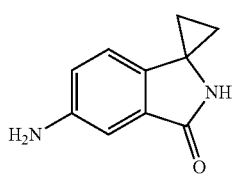 [SMILES: Nc1ccc2c(c1)C(=O)NC21CC1]

At −78° C., to a solution of compound 10-3 (100.00 mg, 567.63 μmol, 1.00 eq) and Ti(i-PrO)$_4$ (643.20 mg, 2.26 mmol, 670.00 μL, 3.99 eq) in tetrahydrofuran (2.00 mL) was added magnesium ethyl bromide (3 M, 1.50 mL, 7.93 eq). The obtained reaction mixture was stirred at a temperature between −78° C. and 10° C. (being warmed up slowly) for 18 hours. A saturated ammonium chloride solution (20 mL) was added to the reaction mixture to form a viscous slurry. Ethyl acetate (20 mL) was added. The resulting mixture was stirred for 10 minutes and then filtered. The filtrate was separated into two phases. The organic phase was washed with a saturated saline solution (15 mL), dried over anhydrous sodium sulfate, and concentrated under reduced pressure. The concentrated residue was purified with a thin-layer chromatography plate to give compound 10-4. LCMS: MS (ESI) m/z: 174.9 (M+1).

Synthesis of Compound 10

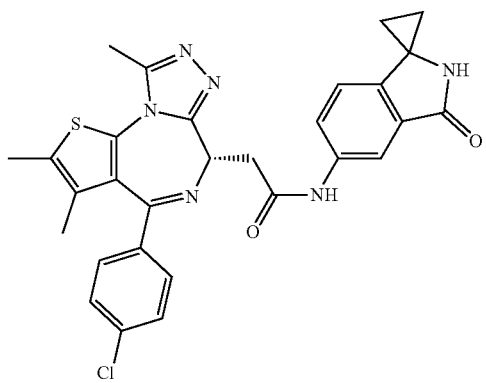 [SMILES: Cc1sc2c(c1C)C(c1ccc(Cl)cc1)=N[C@@H](CC(=O)Nc1ccc3c(c1)C(=O)NC31CC1)c1nnc(C)n1-2]

Compound 1-11 (25.00 mg, 62.36 μmol, 1.00 eq), compound 10-4 (11.95 mg, 68.60 μmol, 1.10 eq), HATU (28.45 mg, 74.84 μmol, 1.20 eq) and triethylamine (15.78 mg, 155.91 μmol, 21.61 μL, 2.50 eq) were dissolved in anhydrous methylene chloride (1.00 mL). The mixture was stirred at 20° C. under the protection of nitrogen gas for 2 hours. The reaction mixture was diluted with methylene chloride (10 mL) and washed with water (5 mL) and a saturated saline solution (5 mL), dried over anhydrous sodium sulfate, filtered and concentrated under reduced pressure. The compound as a crude product was purified with a preparative chromatography to give compound 10. $^1$HNMR (400 MHz, CDCl$_3$) δ ppm 8.10 (br s, 1H), 7.94 (dd, 8.4 Hz, 1H), 7.43 (d, J=8.4 Hz, 2H), 7.35 (d, J=8.8 Hz, 2H), 6.96 (d, J=8.0 Hz, 1H), 6.83 (s, 1H), 4.72-4.76 (m, 1H), 3.86-3.92 (m, 1H), 3.61-3.66 (m, 1H), 2.71 (s, 3H), 2.43 (s, 3H), 1.71 (s, 3H), 1.54-1.57 (m, 2H), 1.35-1.50 (m, 2H). LCMS (ESI) m/z: 557.1 (M+1).

Scheme 11

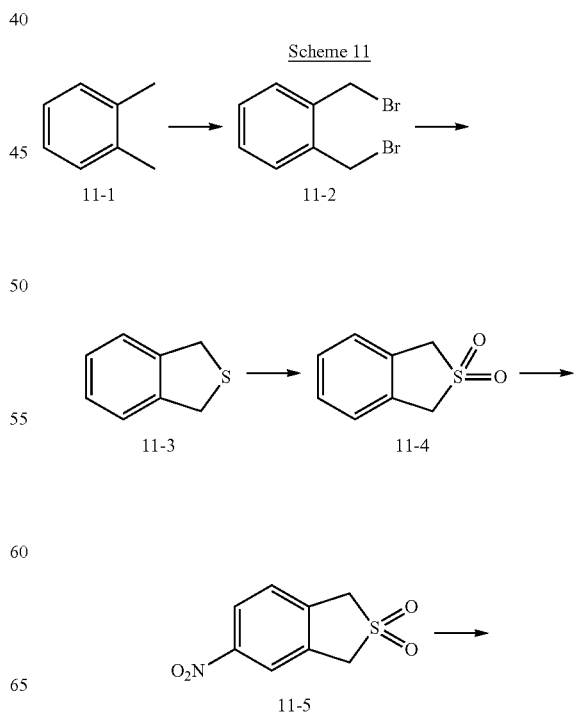

-continued

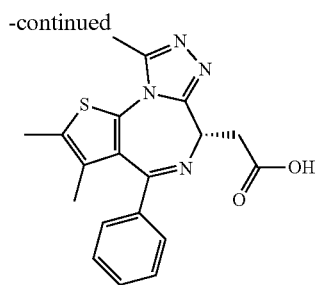

1-11

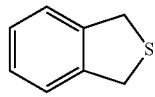

11-6

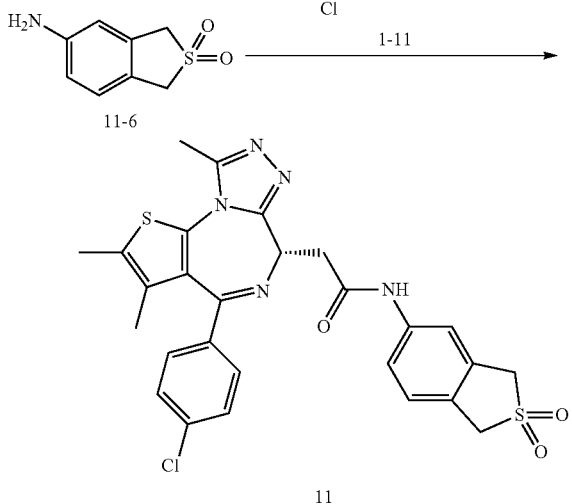

11

Example 11

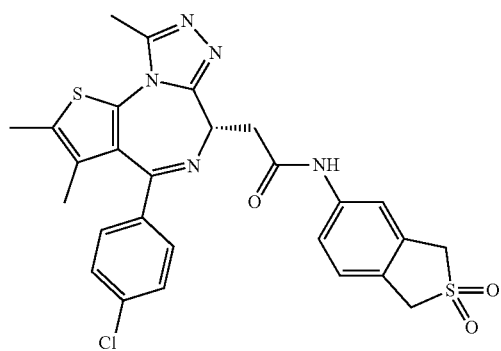 [SMILES: Cc1sc2c(c1C)C(c1ccc(Cl)cc1)=N[C@@H](CC(=O)Nc1ccc3c(c1)CS(=O)(=O)C3)c1nnc(C)n1-2]

Synthesis of Compound 11-2

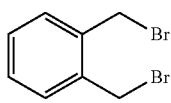

A mixture of ortho-xylene (5.00 g, 47.09 mmol, 5.68 mL, 1.00 eq), NBS (17.60 g, 98.89 mmol, 2.10 eq), benzoyl peroxide (228.13 mg, 941.80 μmol, 0.02 eq) and chloroform (50.00 mL) was stirred at 80° C. for 5 hours. The reaction mixture was cooled to room temperature, then diluted with methylene chloride (100 mL), washed with water (80 mL×2), and washed with a saturated saline solution (50 mL). The organic phase was dried over anhydrous sodium sulfate and filtered. The filtrate was concentrated under reduced pressure. The resulting solid was slurried with (petroleum ether/ethanol=30:1; 60 mL/2 mL) at 80° C. for 20 minutes, cooled to room temperature, and filtered. The filter cake was washed with petroleum ether (20 mL). The filter cake was oven-dried to give compound 11-2. $^1$H NMR (400 MHz, CDCl$_3$) δppm 7.40-7.36 (m, 2H), 7.34-7.30 (m, 2H), 4.68 (s, 4H).

Synthesis of Compound 11-3

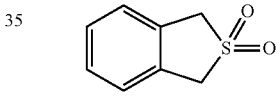

A mixture of compound 11-2 (6.00 g, 22.73 mmol, 3.06 mL, 1.00 eq), sodium sulfide nonahydrate (16.38 g, 68.19 mmol, 11.45 mL, 3.00 eq), benzyl triethyl ammonium chloride (258.86 mg, 1.14 mmol, 0.05 eq), methylene chloride (60.00 mL) and water (60.00 mL) was stirred at 18° C. in the dark for 24 hours. The mixture was extracted with methylene chloride (100 mL). The organic phase was washed with water (80 mL×5), washed with a saturated saline solution (50 mL), then dried over anhydrous sodium sulfate, and filtered. The filtrate was concentrated under reduced pressure to give compound 11-3, which was directly used in the next step without any further purification. $^1$H NMR (400 MHz, CDCl$_3$) δppm 7.20-7.14 (m, 4H), 4.21 (s, 4H).

Synthesis of Compound 11-4

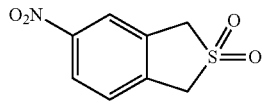 [SMILES: O=[N+]([O-])c1ccc2c(c1)CS(=O)(=O)C2]

Compound 11-3 (2.80 g, 20.56 mmol, 1.00 eq) was dissolved in glacial acetic acid (15.00 mL) at 5-10° C., and then hydrogen peroxide (5.90 g, 52.02 mmol, 5.00 mL, 30% purity, 2.53 eq) was added dropwisely. After the completion of the dropwise addition, the mixture was stirred at 20° C. for 1 hour, and then warmed up to 90° C. and stirred for 3 hours. The reaction mixture was cooled and a solid precipitated. After filtration, the filter cake was washed with water (20 mL). The filter cake was slurried with ethanol (20 mL) at 80° C. for 20 minutes, and the resulting mixture was filtered. The filter cake was oven-dried (1 g). The filtrate was placed for 24 hours and a solid precipitated. After filtration, the filter cake was oven-dried (1 g). The filter cakes were combined to give compound 11-4, which was directly used in the next step without any further purification. $^1$H NMR (400 MHz, CDCl$_3$) δppm 7.41-7.35 (m, 2H), 7.35-7.29 (m, 2H), 4.39 (s, 4H).

Synthesis of Compound 11-5

Compound 11-4 (300.00 mg, 1.78 mmol, 1.00 eq) was dissolved in concentrated sulphuric acid (2.00 mL) at −10° C., and then potassium nitrate (180.31 mg, 1.78 mmol, 1.00 eq) was added. The mixture was stirred at −10° C. for 5 minutes. At −10° C., ice cubes (20 g) were added to quench the reaction. The ice cubes melted and a solid precipitated. After filtration, the filter cake was washed with water (10 mL). The filter cake was oven-dried to give compound 11-5, which was directly used in the next step without any further purification. $^1$H NMR (400 MHz, DMSO-d$_6$) δppm 8.30 (s, 1H), 8.24 (dd, J=2.0, 8.5 Hz, 1H), 7.69 (d, J=8.5 Hz, 1H), 4.67 (d, J=8.3 Hz, 4H).

Synthesis of Compound 11-6

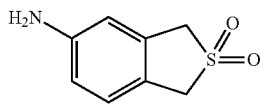

Compound 11-5 (200.00 mg, 938.04 μmol, 1.00 eq) and stannous chloride dihydrate (846.68 mg, 3.75 mmol, 312.43 μL, 4.00 eq) were dissolved in ethanol (3.00 mL), and then concentrated hydrochloric acid (1.32 g, 5.85 mmol, 1.20 mL, 37% purity, 6.23 eq) was added dropwisely at 15° C. After the completion of the dropwise addition, the mixture was stirred at 80° C. for 1 hour, adjusted with a NaOH solution (2N) to pH=10. The mixture was concentrated under reduced pressure to about 50 mL and then extracted with (methylene chloride/methanol=10:1) (40 mL×6). The combined organic phases were washed with a saturated saline solution (50 mL×2). The organic phase was dried over anhydrous sodium sulfate and filtered. The filtrate was concentrated under reduced pressure to give compound 11-6, which was directly used in the next step without any further purification. LCMS (ESI) m/z: 184.1, 206.0 (M+1), (M+23). $^1$H NMR (400 MHz, DMSO-d$_6$) δppm 6.98 (d, J=8.3 Hz, 1H), 6.56-6.52 (m, 1H), 6.50 (s, 1H), 5.31 (br s, 2H), 4.30 (s, 2H), 4.24 (s, 2H).

Synthesis of Compound 11

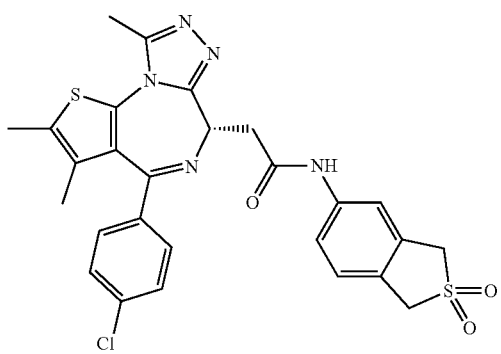 [SMILES: Cc1sc2c(c1C)C(c1ccc(Cl)cc1)=N[C@@H](CC(=O)Nc1ccc3c(c1)CS(=O)(=O)C3)c1nnc(C)n1-2]

At 15° C. and under the protection of nitrogen gas, compound 1-11 (1.00 g, 2.49 mmol, 1.00 eq) and compound 11-6 (547.49 mg, 2.99 mmol, 1.20 eq) were dissolved in anhydrous N,N-dimethyl formamide (15.00 mL). HATU (946.77 mg, 2.49 mmol, 1.00 eq) was added and diisopropylethylamine (965.42 mg, 7.47 mmol, 1.30 mL, 3.00 eq) was added dropwisely. The mixture was stirred at 15° C. in a nitrogen atmosphere for 1 hour. The reaction mixture was directly dried. The obtained solid was shaking washed with water (40 mL). The mixture was extracted with methylene chloride (30 mL×2). The organic phase was washed with a saturated saline solution (50 mL), dried over anhydrous sodium sulfate, filtered and concentrated under reduced pressure. The crude product was purified with a flash chromatography column to give compound 11. LCMS (ESI) m/z: 567.1 (M+1). $^1$H NMR (400 MHz, CDCl$_3$) δ ppm 9.68 (s, 1H), 7.57 (s, 1H), 7.22-7.37 (m, 5H), 7.02 (d, J=8.8 Hz, 1H), 4.60-4.63 (m, 1H), 4.17-4.21 (m, 4H), 3.82-3.88 (m, 1H), 3.38-3.43 (m, 1H), 2.62 (s, 3H), 2.35 (s, 3H), 1.63 (s, 3H).

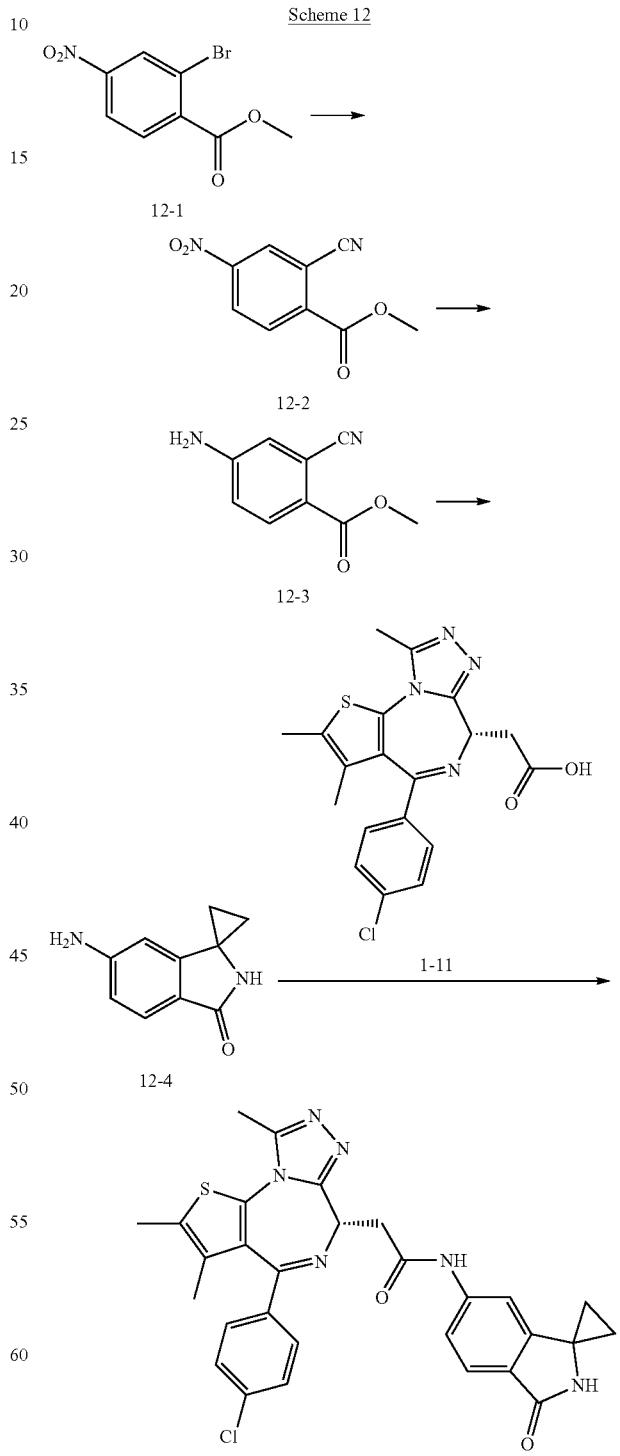

Example 12

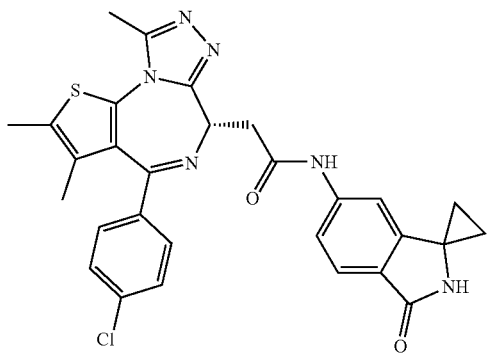 [SMILES: Cc1sc2c(c1C)C(c1ccc(Cl)cc1)=N[C@@H](CC(=O)Nc1ccc3c(c1)C1(CC1)NC3=O)c1nnc(C)n1-2]

Synthesis of Compound 12-2

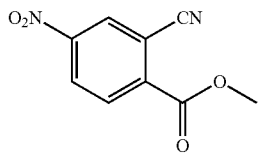

A mixed liquor of compound 12-1 (2.00 g, 7.69 mmol, 1.00 eq), CuCN (1.04 g, 11.61 mmol, 2.54 mL, 1.51 eq), dppf (426.38 mg, 769.00 μmol, 0.10 eq), tris(dibenzylideneacetone) dipalladium (442.25 mg, 769.00 μmol, 0.10 eq) and N,N-dimethyl formamide (20.00 mL) was heated to 120° C. and stirred for 16 hours. The reaction mixture was filtered with diatomaceous earth. The filtrate was concentrated under reduced pressure. The concentrated residue was purified with a silica gel column (petroleum ether/ethyl acetate=1/0-1/1) to give compound 12-2. $^1$H NMR (400 MHz, CDCl$_3$) δppm 8.65 (d, J=2.3 Hz, 1H), 8.51 (dd, 8.8 Hz, 1H), 8.36 (d, J=8.5 Hz, 1H), 4.08 (s, 3H).

Synthesis of Compound 12-3

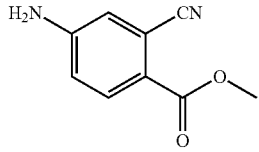

To a solution of compound 12-2 (900.00 mg, 4.37 mmol, 1.00 eq) in glacial acetic acid (20.00 mL) was added reduced iron powder (2.44 g, 43.70 mmol, 10.00 eq). The obtained reaction mixture was stirred at 20° C. for 4 hours. The reaction mixture was filtered with diatomaceous earth, and concentrated under reduced pressure. To the concentrated residue were added ethyl acetate (150 mL) and a saturated aqueous sodium bicarbonate solution (pH 7-8). The organic phase was washed with a saturated saline solution (100 mL), dried over anhydrous sodium sulfate, and concentrated under reduced pressure. The concentrated residue was purified with a thin-layer chromatography plate to give compound 12-3. LCMS (ESI) m/z: 177.1 (M+1).

Synthesis of Compound 12-4

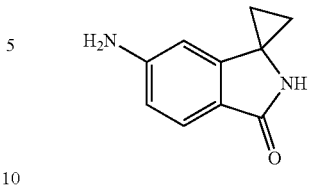

At −78° C., to a solution of compound 12-3 (490.00 mg, 2.78 mmol, 1.00 eq) and Ti(i-PrO)$_4$ (3.07 g, 10.81 mmol, 3.20 mL, 3.89 eq) in tetrahydrofuran (15.00 mL) was added magnesium ethyl bromide (3 M, 7.40 mL, 7.99 eq). The obtained reaction mixture was stirred at a temperature between −78° C. and 15° C. (being warmed up slowly) for 16 hours. As the reaction proceeded, a yellow solid precipitated, and the reaction mixture gradually became earthy yellow and viscous. To the reaction mixture was added a saturated ammonium chloride solution (30 mL), and a viscous slurry was formed. Ethyl acetate (30 mL) was added. The mixture was stirred for 10 minutes and then filtered with diatomaceous earth. The filtrate was separated into two phases. The organic phase was washed with a saturated saline solution (30 mL), dried over anhydrous sodium sulfate, and concentrated under reduced pressure. The concentrated residue was purified with a thin-layer chromatography plate to give compound 12-4. LCMS (ESI) m/z: 174.9 (M+1). $^1$H NMR (400 MHz, CDCl$_3$) δppm 7.65 (d, J=8.0 Hz, 1H), 6.68 (dd, J=2.0, 8.3 Hz, 1H), 6.43 (br s, 1H), 6.23 (d, J=1.8 Hz, 1H), 4.04 (br s, 2H), 1.52-1.46 (m, 2H), 1.37-1.32 (m, 2H).

Synthesis of Compound 12

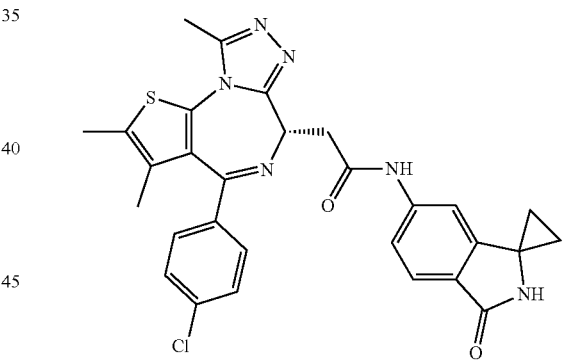

Compound 12-4 (15.64 mg, 89.80 μmol, 1.20 eq) and diisopropylethylamine (29.02 mg, 224.51 μmol, 39.21 μL, 3.00 eq) were dissolved in anhydrous N,N-dimethyl formamide (3.00 mL). Compound 1-11 (30.00 mg, 74.84 μmol, 1.00 eq) and HATU (28.45 mg, 74.84 μmol, 1.00 eq) were added. The atmosphere was replaced with nitrogen gas three times. The mixture was stirred at 15° C. in a nitrogen atmosphere for 16 hours. The reaction mixture was directly concentrated under reduced pressure. The residue was dissolved in methylene chloride (15 mL) and then shaking washed with water (10 mL). The organic phase was washed with a saturated saline solution (20 mL), dried over anhydrous sodium sulfate, filtered and concentrated under reduced pressure. The crude product was purified with a preparative chromatography to give compound 12. LCMS (ESI) m/z: 557.2 (M+1). $^1$H NMR (400 MHz, CDCl$_3$) δ ppm 9.91 (br s, 1H), 7.68 (d, J=8.0 Hz, 1H), 7.63 (s, 1H), 7.44 (d, J=8.8 Hz, 2H), 7.35 (d, J=8.8 Hz, 2H), 7.22 (d, J=8.0 Hz, 1H), 4.70-4.74 (m, 1H), 3.95-3.99 (m, 1H), 3.50-3.54 (m, 1H), 2.73 (s, 3H), 2.45 (s, 3H), 1.72 (s, 3H), 1.46-1.51 (m, 2H), 1.39-1.41 (m, 2H).

Synthesis of Compound 13-1

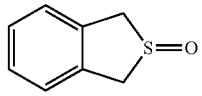

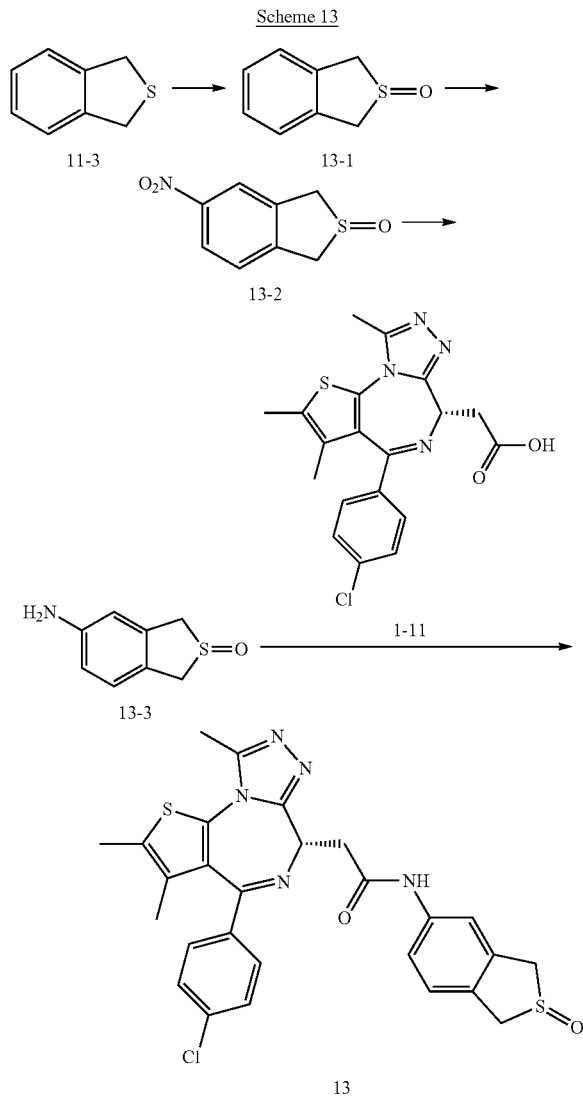

Scheme 13

Example 13

Compound 11-3 (1.80 g, 13.21 mmol, 1.00 eq) was dissolved in methanol (15.00 mL), and then a solution of sodium periodate (2.83 g, 13.21 mmol, 732.26 μL, 1.00 eq) in H$_2$O (15.00 mL) was added dropwisely. After the completion of the dropwise addition, the mixture was stirred at 15° C. for 12 hours. The reaction mixture was concentrated under reduced pressure to about 10 mL and extracted with ethyl acetate (20 mL×5). The combined organic phases were washed with a saturated saline solution (40 mL), then dried over anhydrous sodium sulfate and filtered. The filtrate was concentrated under reduced pressure to give compound 13-1, which was directly used in the next step without any further purification. $^1$H NMR (400 MHz, CDCl$_3$) δppm 7.40-7.36 (m, 2H), 7.36-7.31 (m, 2H), 4.34-4.27 (m, 2H), 4.22-4.13 (m, 2H).

Synthesis of Compound 13-2

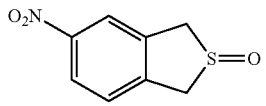 [SMILES: O=[N+]([O-])c1ccc2c(c1)CS(=O)C2]

Compound 13-1 (600.00 mg, 3.94 mmol, 1.00 eq) was dissolved in concentrated sulphuric acid (5.00 mL) at −10° C., and then potassium nitrate (398.53 mg, 3.94 mmol, 1.00 eq) was added. The mixture was stirred at −10° C. for 5 minutes. At −10° C., ice cubes (20 g) were added to quench the reaction. The ice cubes melted, and the mixture was extracted with (methylene chloride/methanol=10:1) (30 mL×4). The combined organic phases were washed with a saturated saline solution (40 mL), then dried over anhydrous sodium sulfate and filtered. The filtrate was concentrated under reduced pressure to give compound 13-2, which was directly used in the next step without any further purification. $^1$H NMR (400 MHz, DMSO-d$_6$) δppm 8.30 (s, 1H), 8.24 (dd, J=2.0, 8.5 Hz, 1H), 7.69 (d, J=8.5 Hz, 1H), 4.67 (d, J=8.3 Hz, 4H).

Synthesis of Compound 13-3

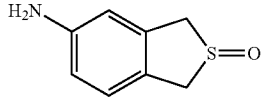

Compound 13-2 (300.00 mg, 1.52 mmol, 1.00 eq) was dissolved in ethanol (8.00 mL), and then stannous chloride dihydrate (686.53 mg, 3.04 mmol, 253.33 μL, 2.00 eq) was added. The mixture was stirred at 80° C. for 1 hour. The mixture was adjusted with a sodium hydroxide solution (1 N) to pH=10, concentrated under reduced pressure to about 50 mL, then extracted with (methylene chloride/methanol=10:1) (40 mL×4). The combined organic phases were washed with a saturated saline solution (60 mL). The organic phase was dried over anhydrous sodium sulfate and filtered. The filtrate was concentrated under reduced pressure. The crude product was purified with a thin-layer chromatography plate to give compound 13-3. LCMS (ESI) m/z: 167.8 (M+1).

Synthesis of Compound 13

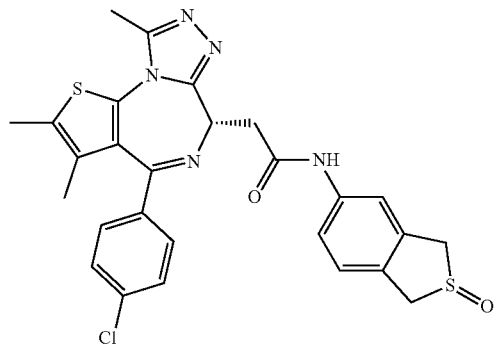 [SMILES: Cc1sc2c(c1C)C(c1ccc(Cl)cc1)=N[C@@H](CC(=O)Nc1ccc3c(c1)CS(=O)C3)c1nnc(C)n1-2]

Compound 1-11 (60.00 mg, 149.67 μmol, 1.00 eq) and compound 13-3 (30.04 mg, 179.60 μmol, 1.20 eq) were successively added to a solution of HATU (74.00 mg, 194.62 μmol, 1.30 eq) in anhydrous N,N-dimethyl formamide (3.00 mL), and then diisopropylethylamine (59.20 mg, 458.06 μmol, 80.00 μL, 3.06 eq) was slowly added dropwisely. The mixture was stirred at 15° C. under the protection of nitrogen gas for 6 hours. Water (3 mL) was added to the reaction mixture to quench the reaction. The mixture was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure. The obtained crude product was purified with a preparative chromatography to give compound 13. $^1$H NMR (400 MHz, CDCl$_3$) δppm 9.35-9.73 (m, 1H), 7.54-7.64 (m, 1H), 7.22-7.38 (m, 5H), 7.09-7.23 (m, 1H), 4.62-4.64 (m, 1H), 3.94-4.18 (m, 4H), 3.81-3.93 (m, 1H), 3.40-3.50 (m, 1H), 2.62 (s, 3H), 2.34 (s, 3H), 1.62 (s, 3H). LCMS (ESI) m/z: 550.1 (M+1).

Schemes 14 and 15

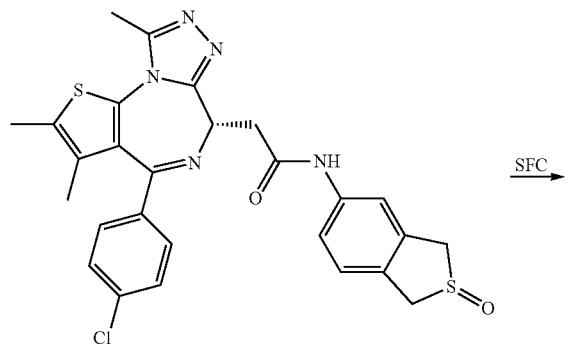

13

SFC →

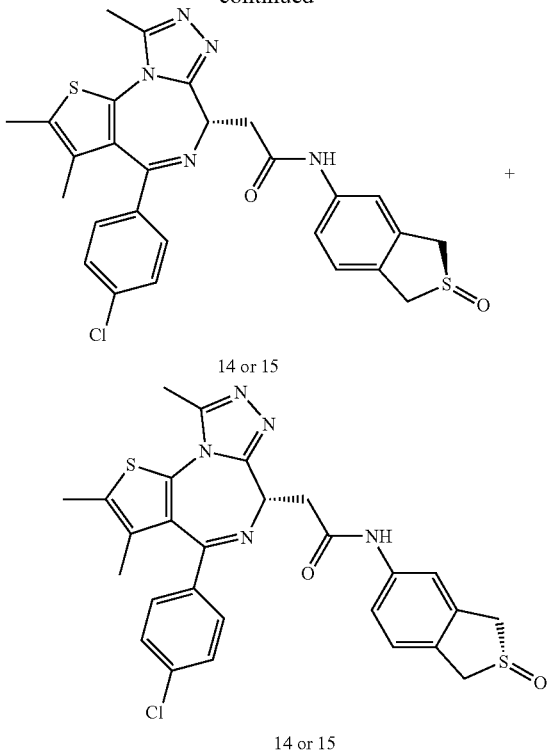

14 or 15

Examples 14 and 15

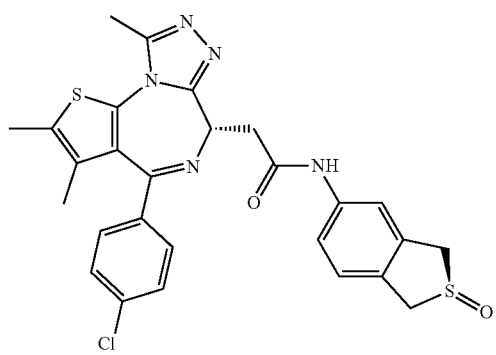

14 or 15

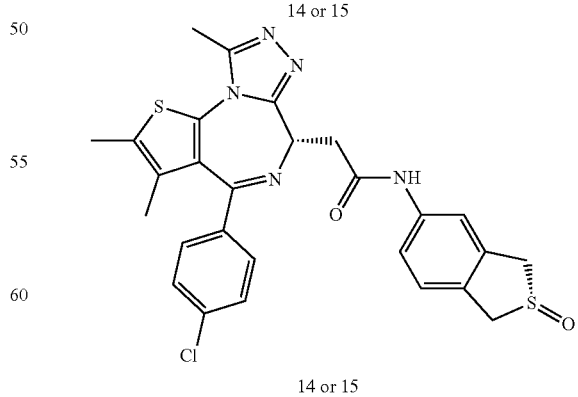

14 or 15

Compound 13 (38 mg, 69.08 μmol) was subjected to a SFC separation (chromatography column: AD (250 mm×30 mm, 10 μm); mobile phase: [0.1% NH₃H₂O EtOH]; B %: 55%-55%, 50 mL/min) to give compound 14 (Rt=0.837 min). ¹H NMR (400 MHz, CDCl₃) δppm 9.49 (s, 1H), 7.59 (s, 1H), 7.25-7.38 (m, 5H), 7.12 (d, J=8.0 Hz, 1H), 4.61-4.64 (m, 1H), 3.99-4.18 (m, 4H), 3.74-3.77 (m, 1H), 3.44-3.50 (m, 1H), 2.62 (s, 3H), 2.34 (s, 3H), 1.61 (s, 3H). LCMS (ESI) m/z: 550.0 (M+1).

Compound 15 (Rt=1.666 min). ¹H NMR (400 MHz, CDCl₃) δ ppm 9.73 (s, 1H), 7.54 (s, 1H), 7.22-7.38 (m, 5H), 7.03 (d, J=8.8 Hz, 1H), 4.65-4.68 (m, 1H), 4.06-4.13 (m, 2H), 3.88-3.98 (m, 3H), 3.40-3.50 (m, 1H), 2.62 (s, 3H), 2.34 (s, 3H), 1.62 (s, 3H). LCMS (ESI) m/z: 550.0 (M+1).

LCMS (ESI) m/z: 518.0 (M+1). ¹H NMR (400 MHz, CDCl₃) δppm 8.88 (s, 1H), 7.62 (s, 1H), 7.44 (d, J=8.8 Hz, 2H), 7.36 (d, J=8.8 Hz, 2H), 7.32-7.34 (m, 1H), 7.16 (d, J=8.0 Hz, 1H), 5.08 (s, 4H), 4.62-4.65 (m, 1H), 3.79-3.85 (m, 1H), 3.48-3.53 (m, 1H), 2.71 (s, 3H), 2.43 (s, 3H), 1.71 (s, 3H).

Scheme 16

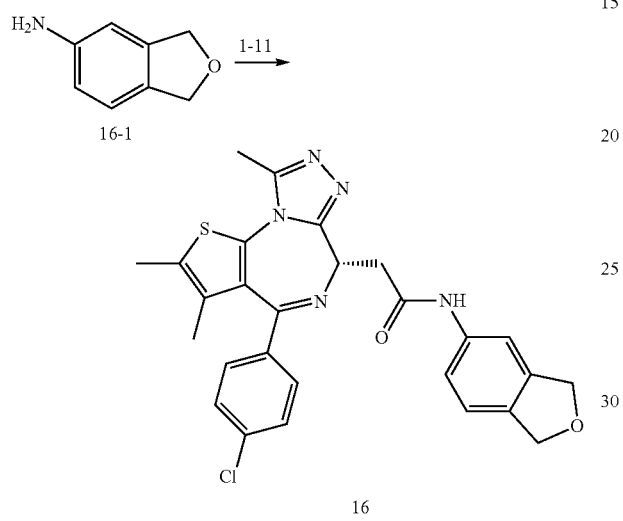

Example 16

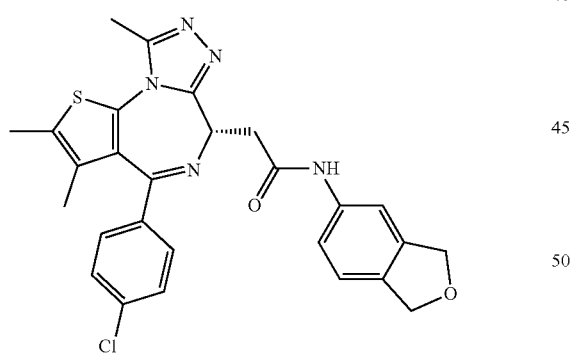

Compound 1-11 (60.00 mg, 149.67 μmol, 1.00 eq) and compound 16-1 (24.28 mg, 179.60 μmol, 1.20 eq) were dissolved in anhydrous methylene chloride (5.00 mL), HATU (56.91 mg, 149.67 μmol, 1.00 eq) was added, and diisopropylethylamine (58.03 mg, 449.01 μmol, 78.42 μL, 3.00 eq) was added dropwise. The mixture was stirred at 15° C. in a nitrogen atmosphere for 1 hour. The reaction mixture was shaking washed with water (10 mL). The organic phase was washed with a saturated saline solution (20 mL), dried over anhydrous sodium sulfate, filtered and concentrated under reduced pressure. The crude product was purified with a preparative chromatography to give compound 16.

Scheme 17

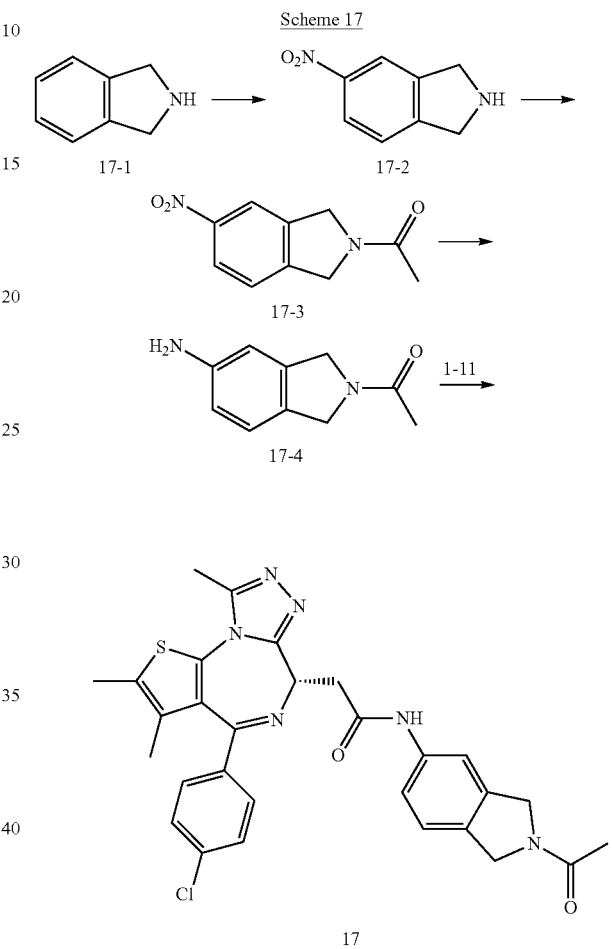

Example 17

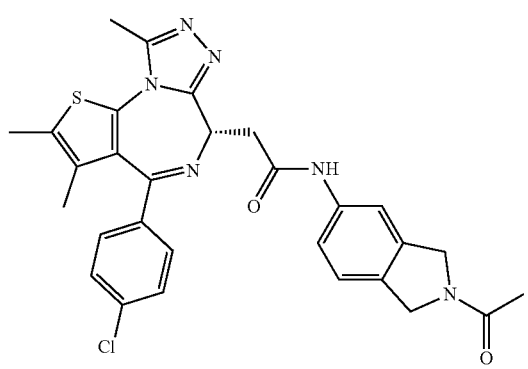 [SMILES: CC(=O)N1Cc2ccc(NC(=O)C[C@@H]3N=C(c4ccc(Cl)cc4)c4c(sc(C)c4C)-n4c(C)nnc43)cc2C1]

Synthesis of Compound 17-2

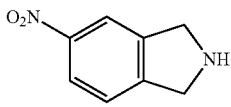 [SMILES: O=[N+]([O-])c1ccc2c(c1)CNC2]

At −20° C. and under the protection of nitrogen gas, concentrated sulphuric acid (16.00 mL) was slowly added to a solution of compound 17-1 (3.90 g, 32.73 mmol, 3.71 mL, 1.00 eq) dissolved in methylene chloride (10.00 mL). After the completion of the dropwise addition, the mixture was slowly warmed up to 20° C. Then methylene chloride was removed under reduced pressure to give a light brown solution. Concentrated nitric acid (5.60 g, 62.19 mmol, 4.00 mL, 1.90 eq) (the content of about 70%) was slowly added dropwisely to the above light brown solution, ensuring the inner temperature not exceeding 20° C. After the completion of the dropwise addition, the mixture was stirred for 0.5 hour. The reaction mixture was slowly added to ice water (300 mL) and then adjusted with solid sodium bicarbonate to pH=8. Methyl tert-butyl ether (300 mL) was added. The mixture was stirred for 1 hour. The organic phase was separated. The aqueous phase was extracted with methyl tert-butyl ether (200 mL×2). The combined organic phases were washed with a saturated saline solution (300 mL), dried over anhydrous sodium sulfate, filtered and concentrated under reduced pressure to give compound 17-2, which was directly used in the next step without any further purification. $^1$H NMR (400 MHz, CDCl$_3$) δppm 8.05 (dd, J=2.0, 8.0 Hz, 1H), 8.03 (s, 1H), 7.30 (d, J=8.0 Hz, 1H), 4.24 (s, 4H).

Synthesis of Compound 17-3

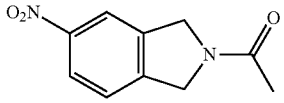

At 0° C., to a solution of compound 17-2 (150.00 mg, 913.74 μmol, 1.00 eq) and triethylamine (277.38 mg, 2.74 mmol, 379.98 μL, 3.00 eq) in anhydrous methylene chloride (5.00 mL) was added acetyl chloride (71.73 mg, 913.74 μmol, 65.21 μL, 1.00 eq). The mixture was reacted under being stirred at 20° C. for 2 hours. The reaction mixture was directly concentrated under reduced pressure. The crude product was purified with a thin-layer chromatography plate to give compound 17-3. $^1$H NMR (400 MHz, CDCl$_3$) δ ppm 8.08-8.15 (m, 2H), 7.35-7.41 (m, 1H), 4.84 (s, 2H), 4.81 (s, 2H), 2.13 (s, 3H).

Synthesis of Compound 17-4

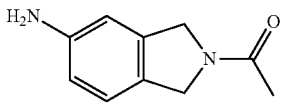

Wet Pd/C (100.00 mg, 10% Pd) was added to a solution of compound 17-3 (140.00 mg, 678.95 μmol, 1.00 eq) in methanol (3.00 mL). The atmosphere was replaced with hydrogen gas three times. The mixture was stirred at 15° C. at a hydrogen balloon (15 psi) condition for 18 hours. The reaction mixture was filtered with diatomaceous earth. The filtrate was directly concentrated under reduced pressure to give compound 17-4, which was directly used in the next step without the need for any further purification. $^1$H NMR (400 MHz, CDCl$_3$) δppm 7.01-7.07 (m, 1H), 6.57-6.65 (m, 2H), 4.67-4.73 (m, 4H), 2.15 (s, 3H).

Synthesis of Compound 17

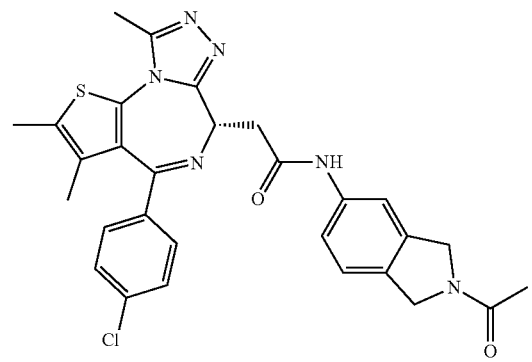 [SMILES: CC(=O)N1Cc2ccc(NC(=O)C[C@@H]3N=C(c4ccc(Cl)cc4)c4c(sc(C)c4C)-n4c(C)nnc43)cc2C1]

Compound 1-11 (200.00 mg, 498.90 μmol, 1.00 eq) and compound 17-4 (100.00 mg, 567.50 μmol, 1.14 eq) were successively added to a solution of HATU (240.00 mg, 631.20 μmol, 1.27 eq) in anhydrous N,N-dimethyl formamide (5.00 mL), and then triethylamine (146.00 mg, 1.44 mmol, 200.00 μL, 2.89 eq) was slowly added dropwisely. The mixture was stirred at 15° C. under the protection of nitrogen gas for 4 hours. Water (5 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure. The above crude product was purified with a preparative chromatography to give compound 17. $^1$H NMR (400 MHz, CDCl$_3$) δppm 9.16-9.20 (m, 1H), 7.61-7.70 (m, 1H), 7.31-7.43 (m, 5H), 7.14-7.18 (m, 1H), 4.62-4.76 (m, 5H), 3.81-3.84 (m, 1H), 3.47-3.52 (m, 1H), 2.69 (s, 3H), 2.41 (s, 3H), 2.15 (s, 3H), 1.69 (s, 3H). LCMS (ESI) m/z: 559.1 (M+1).

Scheme 18

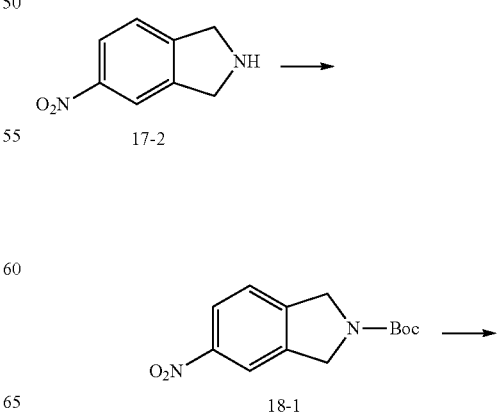

-continued

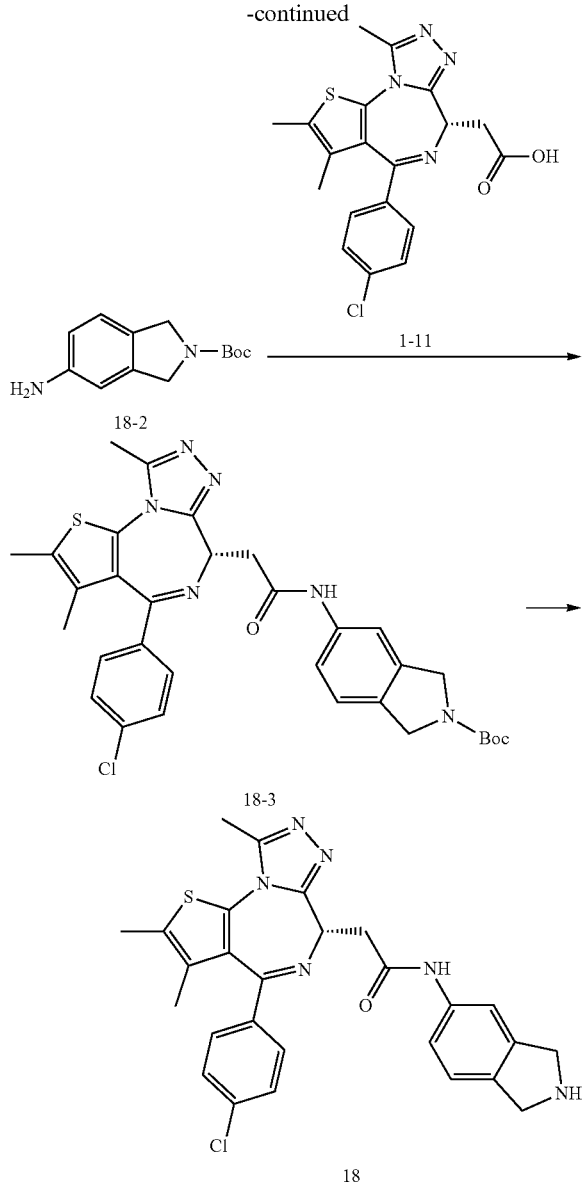

Example 18

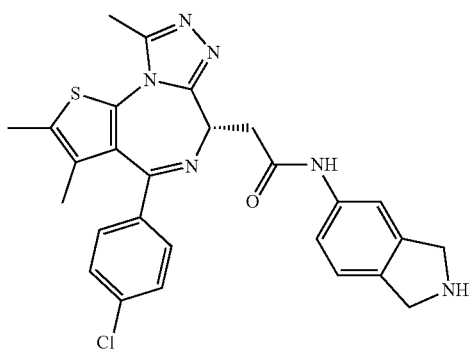 [SMILES: Cc1sc2c(c1C)C(c1ccc(Cl)cc1)=N[C@@H](CC(=O)Nc1ccc3c(c1)CNC3)c1nnc(C)n1-2]

Synthesis of Compound 18-1

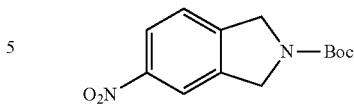

Compound 17-2 (30.00 mg, 182.75 μmol, 1.00 eq) and (Boc)₂O (47.50 mg, 217.47 μmol, 50.00 μL, 1.19 eq) were successively added to a solution of 4-dimethylaminopyridine (1.00 mg, 8.19 μmol, 0.04 eq) in anhydrous methylene chloride (3.00 mL). Then to the reaction mixture was slowly added dropwisely triethylamine (55.48 mg, 548.25 μmol, 76.00 μL, 3.00 eq). The mixture was stirred at 15° C. under the protection of nitrogen gas for 6 hours. Water (3 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure to give compound 18-1, which was directly used in the next step without the need for any further purification. ¹H NMR (400 MHz, CDCl₃) δppm 8.00-8.15 (m, 2H), 7.28-7.38 (m, 1H), 4.68 (d, J=10.8 Hz, 4H), 1.45 (s, 9H).

Synthesis of Compound 18-2

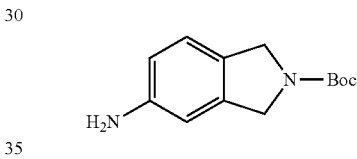

Wet Pd/C (100.00 mg, 10% Pd) was added to a solution of compound 18-1 (40.00 mg, 151.35 μmol, 1.00 eq) in methanol (3.00 mL). The atmosphere was replaced with hydrogen gas three times. The mixture was stirred at 15° C. at a hydrogen balloon (15 psi) condition for 3 hours. The reaction mixture was filtered with diatomaceous earth. The filtrate was directly concentrated under reduced pressure to give compound 18-2, which was directly used in the next step without the need for any further purification. ¹H NMR (400 MHz, CDCl₃) δppm 6.86-6.99 (m, 1H), 6.44-6.56 (m, 2H), 4.41-4.53 (m, 4H), 1.43 (s, 9H).

Synthesis of Compound 18-3

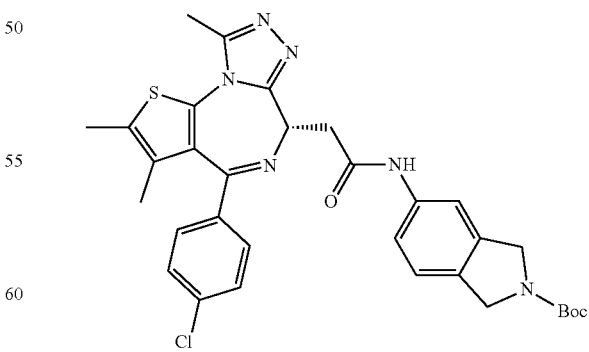

Compound 1-11 (40.00 mg, 99.78 μmol, 1.00 eq) and compound 18-2 (30.00 mg, 128.05 μmol, 1.28 eq) were successively added to a solution of HATU (48.00 mg, 126.24 μmol, 1.27 eq) in anhydrous N,N-dimethyl formamide (3.00 mL), and then triethylamine (29.20 mg, 288.57 μmol, 40.00 μL, 2.89 eq) was slowly added dropwisely. The mixture was stirred at 15° C. under the protection of nitrogen gas for 4 hours. Water (3 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure. The above crude product was purified with a preparative chromatography to give compound 18-3. LCMS (ESI) m/z: 617.0 (M+1).

Synthesis of Compound 18

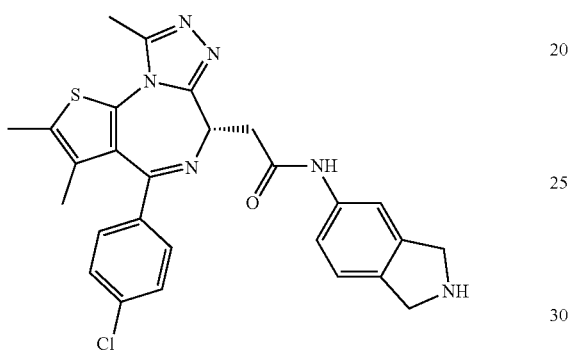

At 15° C. and under the protection of nitrogen gas, trifluoroacetic acid (3.08 g, 27.01 mmol, 2.00 mL, 333.41 eq) was added to a solution of compound 18-3 (50.00 mg, 81.02 μmol, 1.00 eq) in anhydrous methylene chloride (6.00 mL). The mixture was stirred at 15° C. for 4 hours. The reaction mixture was directly concentrated under reduced pressure, adjusted with a saturated aqueous sodium bicarbonate solution to pH=7, and extracted with methylene chloride (3×5 mL). The above organic phases were combined. The organic phase was washed with a saturated saline solution (5 mL), then dried over anhydrous sodium sulfate and filtered. The filtrate was concentrated under reduced pressure. The above crude product was purified with a preparative chromatography to give compound 18. $^1$H NMR (400 MHz, CDCl$_3$) δppm 9.12 (s, 1H), 7.57 (s, 1H), 7.32-7.47 (m, 5H), 7.13-7.15 (m, 1H), 4.68-4.71 (m, 1H), 3.82-3.88 (m, 1H), 3.50-3.55 (m, 1H), 2.71 (s, 3H), 2.43 (s, 3H), 1.70 (s, 3H). LCMS (ESI) m/z: 539.1 (M+1).

Scheme 19

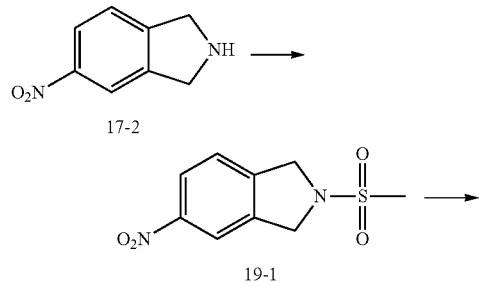

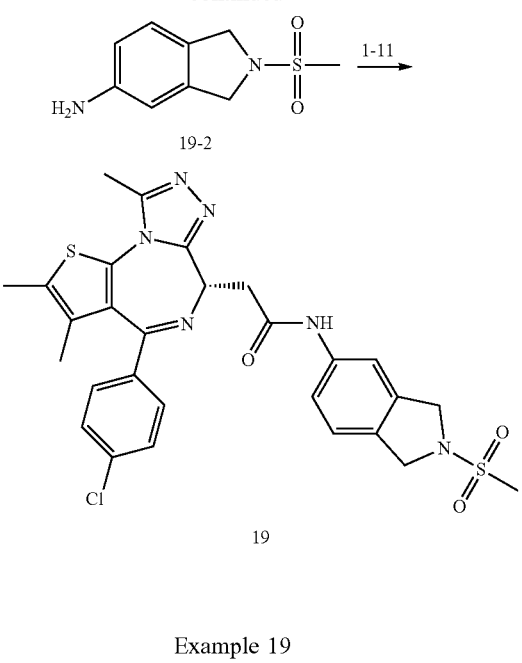

Example 19

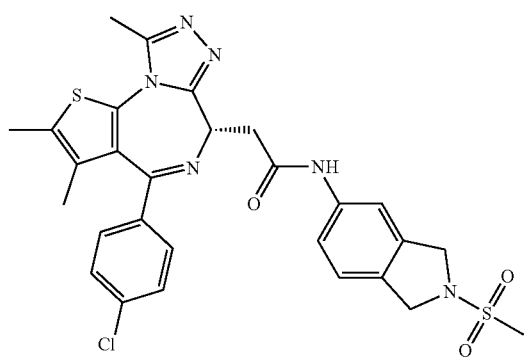

Synthesis of Compound 19-1

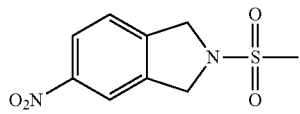 [SMILES: CS(=O)(=O)N1Cc2ccc([N+](=O)[O-])cc2C1]

Triethylamine (948.78 mg, 9.38 mmol, 1.30 mL, 2.96 eq) was added to a solution of compound 17-2 (520.00 mg, 3.17 mmol, 1.00 eq) in methylene chloride (5.00 mL). The mixture was cooled to 0° C. under the protection of nitrogen gas. To the reaction mixture was slowly added dropwisely methylsulfonyl chloride (370.00 mg, 3.23 mmol, 250.00 μL, 1.02 eq). After the completion of the dropwise addition, the mixture was warmed up to 15° C. and stirred for 2 hours.

The reaction mixture was directly concentrated under reduced pressure. The above crude product was purified with a flash chromatography column to give compound 19-1. $^1$H NMR (400 MHz, CDCl$_3$) δppm 8.24 (d, J=8.4 Hz, 1H), 8.17 (s, 1H), 7.46 (d, J=8.4 Hz, 1H), 4.83 (s, 4H), 2.97 (s, 3H).

Synthesis of Compound 19-2

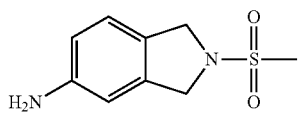

Wet Pd/C (100.00 mg, 10% Pd) was added to a solution of compound 19-1 (50.00 mg, 206.40 μmol, 1.00 eq) in methanol (3.00 mL). The atmosphere was replaced with hydrogen gas three times. The mixture was stirred at 15° C. at a hydrogen balloon (15 psi) condition for 3 hours. The reaction mixture was filtered with diatomaceous earth. The filtrate was directly concentrated under reduced pressure to give compound 19-2, which was directly used in the next step without the need for any further purification. $^1$H NMR (400 MHz, CDCl$_3$) δppm 6.95 (d, J=8.28 Hz, 1H), 6.54-6.57 (m, 1H), 6.50 (s, 1H), 4.52 (s, 4H), 2.78 (s, 3H).

Synthesis of Compound 19

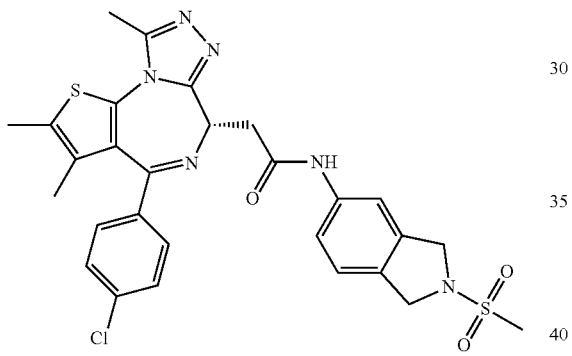

Compound 1-11 (60.00 mg, 149.67 μmol, 1.00 eq) and compound 19-2 (40.00 mg, 188.58 μmol, 1.26 eq) were successively added to a solution of HATU (73.00 mg, 191.99 μmol, 1.28 eq) in anhydrous methylene chloride (3.00 mL), and then triethylamine (43.80 mg, 432.55 μmol, 60.00 μL, 2.89 eq) was slowly added dropwisely. The mixture was stirred at 15° C. under the protection of nitrogen gas for 2 hours. Water (3 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure. The above crude product purified with a thin-layer chromatography plate to give compound 19. $^1$H NMR (400 MHz, CDCl$_3$) δppm 9.82 (s, 1H), 7.51 (s, 1H), 7.17-7.40 (m, 5H) 6.96-6.98 (m, 1H), 4.68-4.70 (m, 1H), 4.49 (d, J=17.2 Hz, 4H), 3.83-3.89 (m, 1H), 3.46-3.51 (m, 1H), 2.82 (s, 3H), 2.62 (s, 3H), 2.35 (s, 3H), 1.62 (s, 3H). LCMS (ESI) m/z: 595 (M+1).

Scheme 20

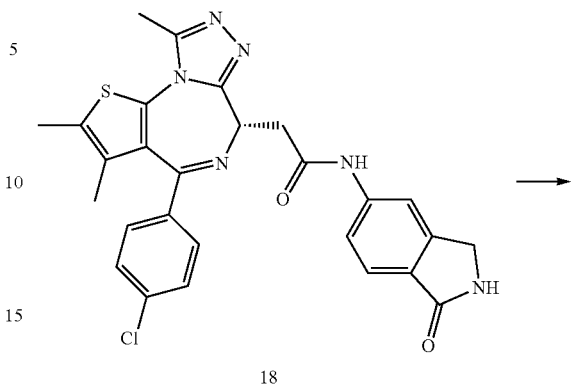

18

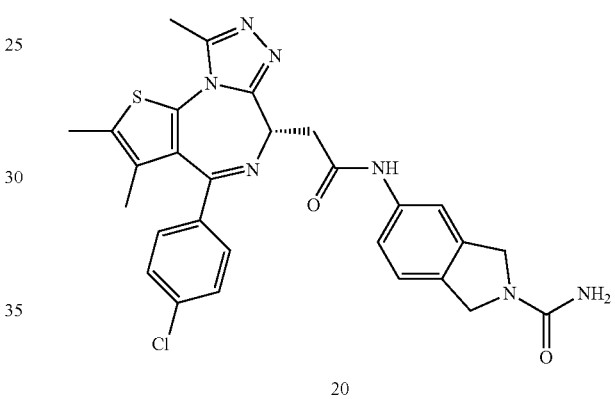

20

Example 20

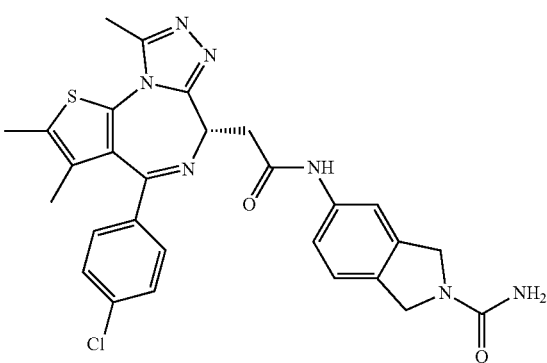 [SMILES: Cc1sc2c(c1C)C(c1ccc(Cl)cc1)=N[C@@H](CC(=O)Nc1ccc3c(c1)CN(C(N)=O)C3)c1nnc(C)n1-2]

Synthesis of Compound 20

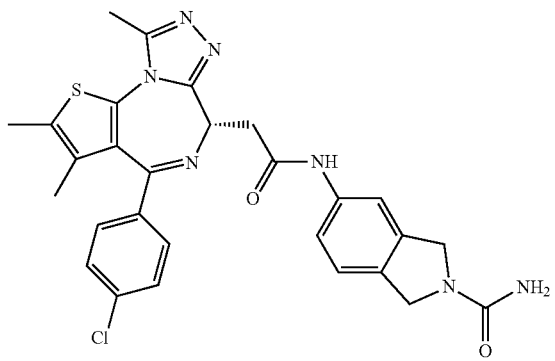 [SMILES: Cc1sc2c(c1C)C(c1ccc(Cl)cc1)=N[C@@H](CC(=O)Nc1ccc3c(c1)CN(C(N)=O)C3)c1nnc(C)n1-2]

Compound 18 (140.00 mg, 270.77 μmol, 1.00 eq) was added to a mixed liquor of glacial acetic acid (2.00 mL) and H$_2$O (2 mL). Then to the reaction mixture was slowly added dropwisely a solution of sodium cyanate (35.00 mg, 538.38 μmol, 1.99 eq) in water (2 mL). The mixture was stirred at 15° C. for 18 hours. The reaction mixture was directly concentrated under reduced pressure. The crude product was purified with a preparative chromatography to give compound 20. $^1$H NMR (400 MHz, CDCl$_3$) δppm 9.09 (s, 1H), 7.58 (s, 1H), 7.24-7.37 (m, 5H), 7.08 (d, J=8.4 Hz, 1H), 4.50-4.58 (m, 5H), 4.42 (br s, 2H), 3.73-3.79 (m, 1H), 3.39-3.44 (m, 1H), 2.62 (s, 3H), 2.34 (s, 3H), 1.62 (s, 3H). LCMS (ESI) m/z: 560.0 (M+1).

Scheme 21

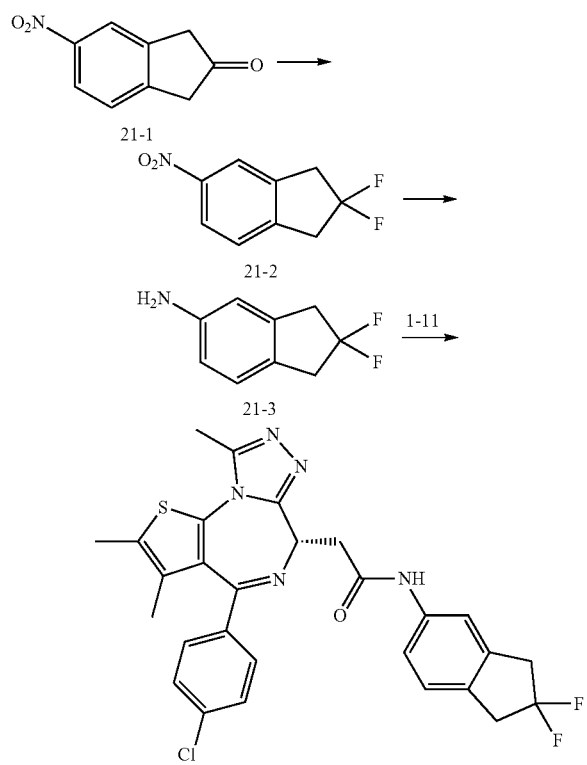

Example 21

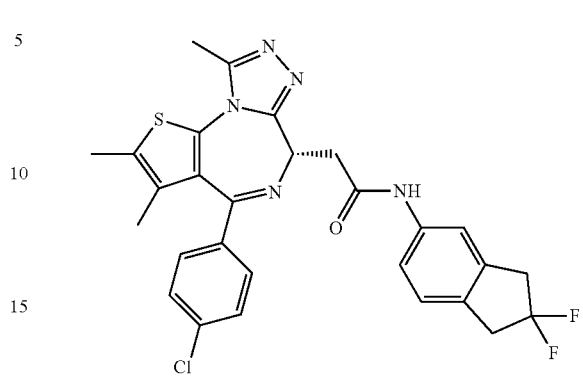

Synthesis of Compound 21-2

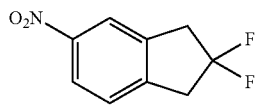 [SMILES: O=[N+]([O-])c1ccc2c(c1)CC(F)(F)C2]

Compound 21-1 (300.00 mg, 1.69 mmol, 1.00 eq) and diethylaminosulfur trifluoride (545.91 mg, 3.39 mmol, 447.47 μL, 2.00 eq) were dissolved in anhydrous methylene chloride (10.00 mL). The mixture was stirred at 15° C. in a nitrogen atmosphere for 16 hours. To the reaction mixture was added water (30 mL). Then, the mixture was extracted with methylene chloride (20 mL×2). The organic phase was washed with a saturated saline solution (30 mL), dried over anhydrous sodium sulfate, filtered and concentrated under reduced pressure. The crude product was purified with a thin-layer chromatography plate to give compound 21-2. $^1$H NMR (400 MHz, CDCl$_3$) δ ppm 8.13-8.17 (m, 2H), 7.39-7.42 (m, 1H), 3.51-3.59 (m, 4H).

Synthesis of Compound 21-3

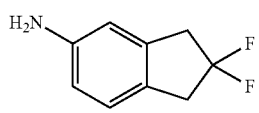

Compound 21-2 (70.00 mg, 351.49 μmol, 1.00 eq) and Pd(OH)$_2$/C (50 mg, 10% purity) were added to methanol (5.00 mL). The mixture was stirred at 15° C. under a hydrogen balloon atmosphere for 16 hours. The reaction mixture was filtered through a pad of celite and concentrated under reduced pressure to give compound 21-3, which was directly used in the next step without the need for any further purification.

Synthesis of Compound 21

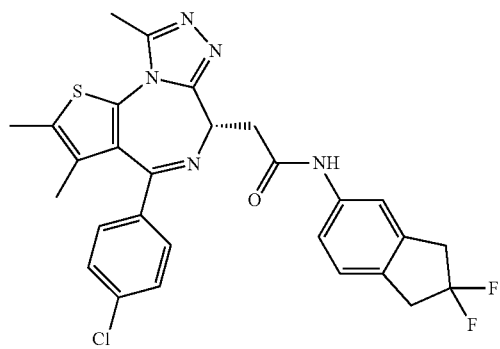 [SMILES: Cc1sc2c(c1C)C(c1ccc(Cl)cc1)=N[C@@H](CC(=O)Nc1ccc3c(c1)CC(F)(F)C3)c1nnc(C)n1-2]

Compound 1-11 (60.00 mg, 149.67 μmol, 1.00 eq) and compound 21-3 (30.38 mg, 179.60 μmol, 1.20 eq) were added to anhydrous methylene chloride (5.00 mL), then HATU (56.91 mg, 149.67 μmol, 1.00 eq) was added, and diisopropylethylamine (58.03 mg, 449.01 μmol, 78.42 μL, 3.00 eq) was added dropwisely. The atmosphere was replaced with nitrogen gas three times. The mixture was stirred at 15° C. in a nitrogen atmosphere for 16 hours. The reaction mixture was directly concentrated under reduced pressure, then shaking washed with water (10 mL), and extracted with ethyl acetate (10 mL×2). The organic phase was washed with a saturated saline solution (20 mL), dried over anhydrous sodium sulfate, filtered and concentrated under reduced pressure. The crude product was purified with a preparative chromatography to give compound 21. LCMS (ESI) m/z: 551.9 (M+1). $^1$H NMR (400 MHz, CDCl$_3$) δ ppm 9.00 (s, 1H), 7.60 (s, 1H), 7.43 (d, J=8.4 Hz, 2H), 7.33-7.38 (m, 3H), 7.14 (d, J=8.0 Hz, 1H), 4.64-4.67 (m, 1H), 3.52-3.80 (m, 1H), 3.51-3.52 (m, 1H), 3.34-3.44 (m, 4H), 2.70 (s, 3H), 2.43 (s, 3H), 1.71 (s, 3H).

Scheme 22

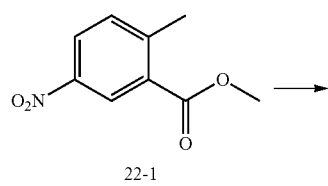

22-1

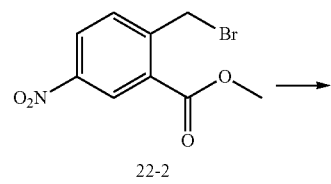

22-2

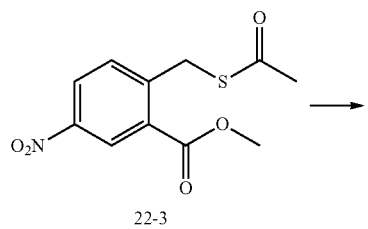

22-3

-continued

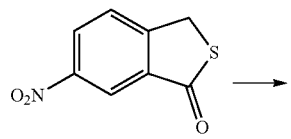

22-4

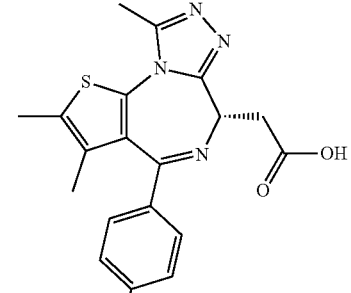

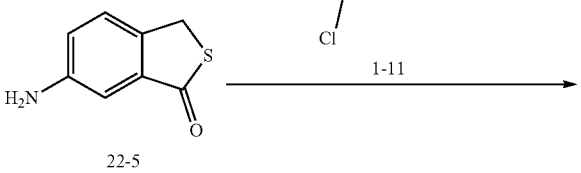

22-5

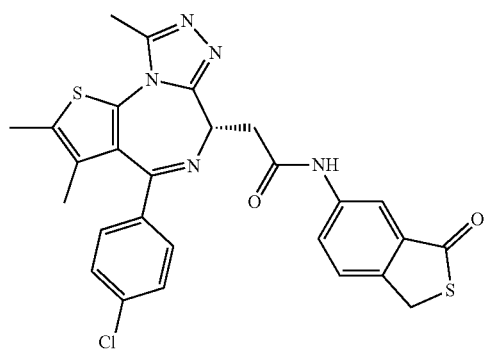

22

Example 22

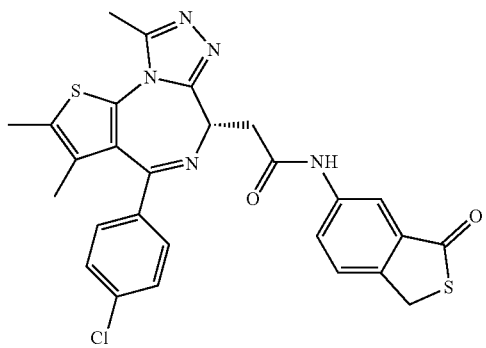 [SMILES: Cc1sc2c(c1C)C(c1ccc(Cl)cc1)=N[C@@H](CC(=O)Nc1ccc3c(c1)C(=O)SC3)c1nnc(C)n1-2]

Synthesis of Compound 22-2

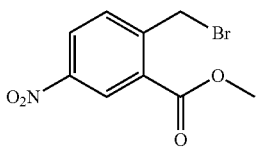

To a solution of compound 22-1 (1.00 g, 5.12 mmol, 1.00 eq) and NBS (1.00 g, 5.63 mmol, 1.10 eq) in carbon tetrachloride (10.00 mL) was added benzoyl peroxide (124.02 mg, 512.00 μmol, 0.10 eq). The mixture was reacted under being stirred at 85° C. for 4 hours. The reaction mixture was directly concentrated under reduced pressure. The crude product was purified with a flash chromatography column to give compound 22-2. $^1$H NMR (400 MHz, CDCl$_3$) δppm 8.85 (d, J=2.4 Hz, 1H), 8.34-8.37 (m, 1H), 7.71 (d, J=8.8 Hz, 1H), 5.02 (s, 2H), 4.03 (s, 3H).

Synthesis of Compound 22-3

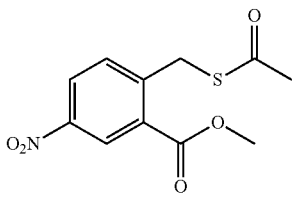 [SMILES: COC(=O)c1cc([N+](=O)[O-])ccc1CSC(C)=O]

At 0° C. and under the protection of nitrogen gas, thioacetic acid (288.90 mg, 3.80 mmol, 270.00 μL, 1.04 eq) slowly added dropwisely to a solution of compound 22-2 (1.00 g, 3.65 mmol, 1.00 eq) and potassium carbonate (948.40 mg, 6.86 mmol, 1.88 eq) in acetone (4.00 mL). After the completion of the dropwise addition, the mixture was stirred at 0° C. under the protection of nitrogen gas for 30 minutes, and then warmed up to 15° C. and stirred for 3 hours. The reaction mixture was concentrated to remove acetone. The resulting mixture was diluted with water (10 mL) and extracted with ethyl acetate (3×10 mL). The above organic phases were combined, dried over anhydrous sodium sulfate and filtered. The filtrate was concentrated under reduced pressure. The above crude product purified with a thin-layer chromatography plate to give compound 22-3. $^1$H NMR (400 MHz, CDCl$_3$) δppm 8.83 (s, 1H), 8.31-8.32 (m, 1H), 7.77 (m, J=8.4 Hz, 1H), 4.56 (s, 2H), 4.00 (s, 3H), 2.34 (s, 3H).

Synthesis of Compound 22-4

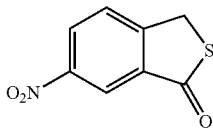 [SMILES: O=C1SCc2ccc([N+](=O)[O-])cc21]

Compound 22-3 (800.00 mg, 2.97 mmol, 1.00 eq) was added to concentrated hydrochloric acid (5.88 g, 47.76 mmol, 4.00 mL, 16.08 eq), and the mixture was stirred at 90° C. for 2 hours. The reaction mixture was cooled to room temperature, and adjusted with a saturated sodium bicarbonate solution to pH=7. The mixture was extracted with ethyl acetate (3×10 mL) and separated into two phases. The above organic phases were combined. The organic phase was dried over anhydrous sodium sulfate and filtered. The filtrate was concentrated under reduced pressure. The above crude product was purified with a flash chromatography column to give compound 22-4. $^1$H NMR (400 MHz, CDCl$_3$) δppm 8.59 (m, J=2.0 Hz, 1H), 8.43 (dd, J=8.4, 2.0 Hz, 1H), 7.66 (d, J=8.4 Hz, 1H), 4.53 (s, 2H).

Synthesis of Compound 22-5

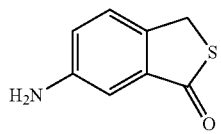

Wet Pd/C (50.00 mg, 10% Pd) was added to a solution of compound 22-4 (100.00 mg, 512.30 μmol, 1.00 eq) in methanol (3.00 mL). The atmosphere was replaced with hydrogen gas three times. The mixture was stirred at 15° C. at a hydrogen balloon (15 psi) condition for 18 hours. The reaction mixture was filtered with diatomaceous earth. The filtrate was directly concentrated under reduced pressure. The above crude product was purified with a thin-layer chromatography plate to give compound 22-5. LCMS (ESI) m/z: 165.8 (M+1).

Synthesis of Compound 22

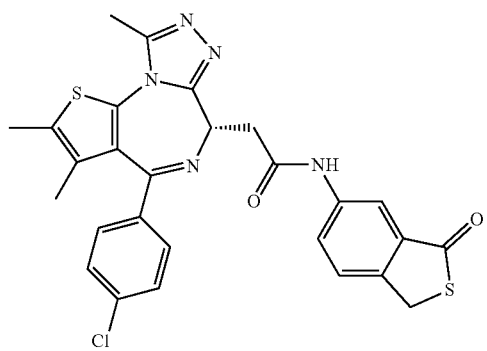 [SMILES: Cc1sc2c(c1C)C(c1ccc(Cl)cc1)=N[C@@H](CC(=O)Nc1ccc3c(c1)C(=O)SC3)c1nnc(C)n1-2]

Compound 1-11 (30 mg, 74.84 μmol, 1.00 eq) and compound 22-5 (99.218% purity) were successively added to a solution of HATU (36 mg, 94.68 μmol, 1.27 eq) in anhydrous N,N-dimethyl formamide (2 mL), and then triethylamine (21.90 mg, 216.42 μmol, 30 μL, 2.89 eq) was slowly added dropwisely. The mixture was stirred at 15° C. under the protection of nitrogen gas for 18 hours. Water (3 mL) was added to the reaction mixture to quench the reaction. The mixture was separated into two phases. The aqueous phase was extracted with methylene chloride (3×5 mL). The above organic phases were combined. The organic phase was washed with a saturated sodium bicarbonate solution (5 mL) and a saturated saline solution (5 mL), then dried over anhydrous sodium sulfate and filtered. The filtrate was concentrated under reduced pressure. The above crude product was purified with a preparative chromatography to give compound 22. LCMS (ESI) m/z: 548.1 (M+1). $^1$H NMR (400 MHz, CDCl$_3$) δppm 10.08 (s, 1H), 8.01 (s, 1H), 7.66 (d, J=8.0 Hz, 1H), 7.29-7.46 (m, 5H), 4.80-4.83 (m, 1H), 4.30 (s, 2H), 3.97-4.03 (m, 1H), 3.58-3.63 (m, 1H), 2.78 (s, 3H), 2.45 (s, 3H), 1.71 (s, 3H).

Schemes 23 and 24

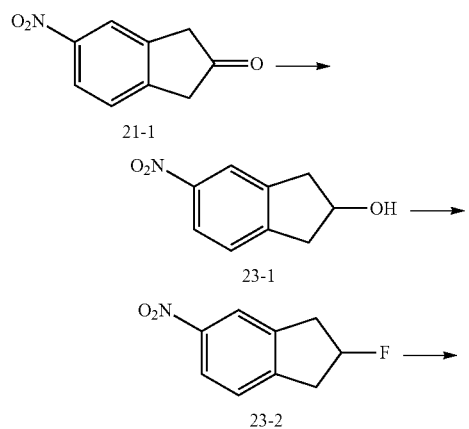

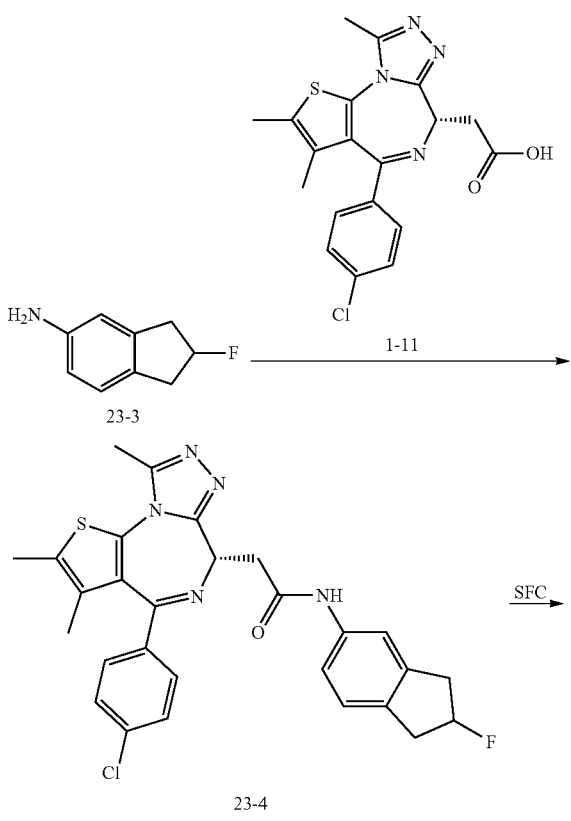

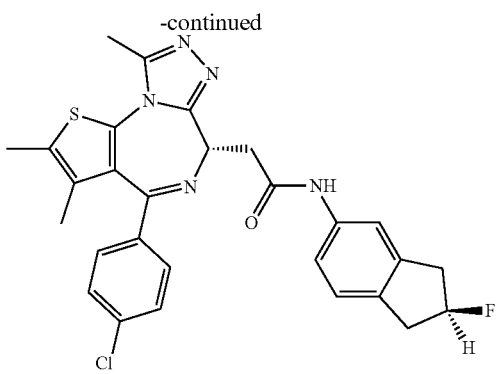

Examples 23 and 24

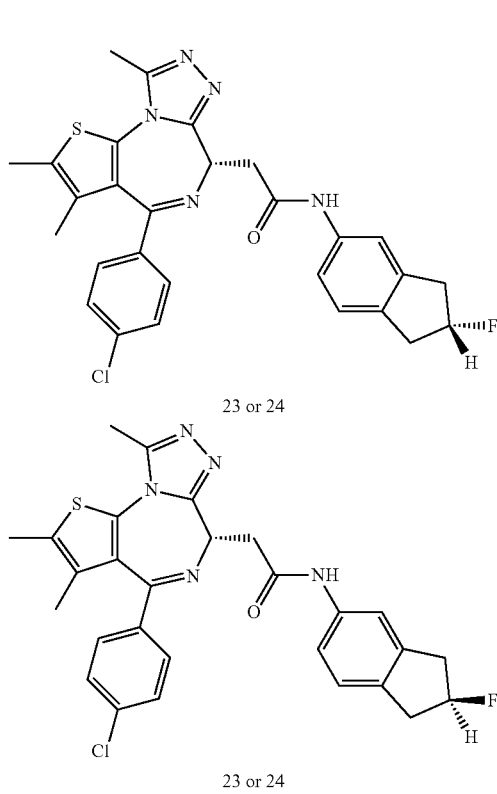

Synthesis of Compound 23-1

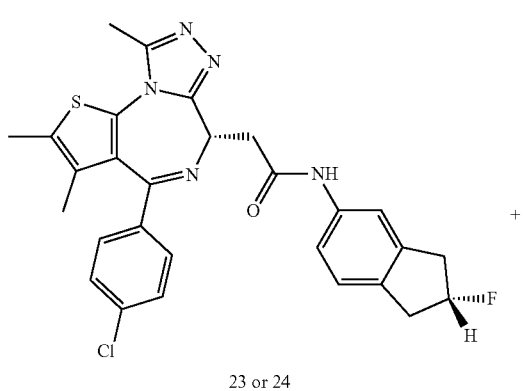

Compound 21-1 (200.00 mg, 1.13 mmol, 1.00 eq) and sodium borohydride (85.50 mg, 2.26 mmol, 2.00 eq) were dissolved in absolute methanol (5.00 mL), and the mixture was stirred at 15° C. in a nitrogen atmosphere for 1 hour. The reaction mixture was directly concentrated under reduced pressure, and water (20 mL) was added thereto. Then the mixture was extracted with ethyl acetate (10 mL×2). The organic phase was washed with a saturated saline solution (30 mL), dried over anhydrous sodium sulfate, filtered and concentrated under reduced pressure to give compound 23-1, which was directly used in the next step without the need for any further purification. $^1$H NMR (400 MHz, CDCl$_3$) δppm 8.00-8.03 (m, 2H), 7.31 (d, J=8.0 Hz, 1H), 4.75 (br s, 1H), 3.18-3.25 (m, 2H), 2.92-2.97 (m, 2H), 1.61 (br s, 1H).

Synthesis of Compound 23-2

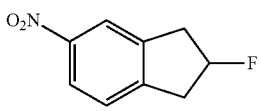

Compound 23-1 (190 mg, 1.06 mmol, 1.00 eq) and diethylaminosulfur trifluoride (188.02 mg, 1.17 mmol, 154.12 μL, 1.1 eq) were dissolved in anhydrous methylene chloride (5.00 mL). The mixture was stirred at 15° C. in a nitrogen atmosphere for 16 hours. To the reaction mixture was added water (20 mL). Then, the mixture was extracted with methylene chloride (20 mL×2). The organic phase was washed with a saturated saline solution (30 mL), dried over anhydrous sodium sulfate, filtered and concentrated under reduced pressure. The crude product was purified with a thin-layer chromatography plate to give compound 23-2. $^1$H NMR (400 MHz, CDCl$_3$) δppm 8.03-8.07 (m, 2H), 7.31-7.35 (m, 1H), 5.27-5.61 (m, 1H), 3.26-3.28 (m, 2H), 3.19-3.20 (m, 2H).

Synthesis of Compound 23-3

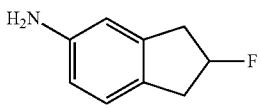

Compound 23-2 (30 mg, 165.60 μmol, 1.00 eq) and Pd/C (30 mg, 10% purity) were added to methanol (3 mL). The mixture was stirred at 15° C. under a hydrogen balloon atmosphere for 2 hours. The reaction mixture was directly filtered and concentrated under reduced pressure to give compound 23-3, which was directly used in the next step without the need for any further purification. $^1$H NMR (400 MHz, CDCl$_3$) δppm 6.90-6.95 (m, 1H), 6.52 (s, 1H), 6.41-6.49 (m, 1H), 5.24-5.50 (m, 1H), 2.95-3.11 (m, 4H).

Synthesis of Compound 23-4

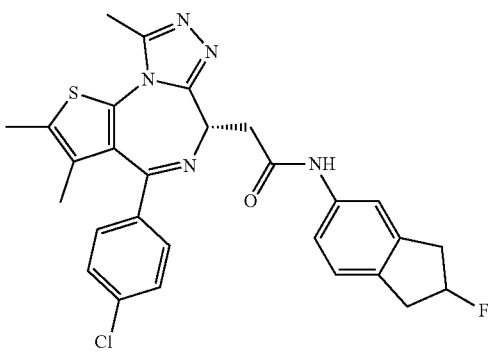 [SMILES: Cc1sc2c(c1C)C(c1ccc(Cl)cc1)=N[C@@H](CC(=O)Nc1ccc3c(c1)CC(F)C3)c1nnc(C)n1-2]

Compound 1-11 (60 mg, 149.67 μmol, 1.00 eq) and compound 23-3 (25 mg, 165.37 μmol, 1.10 eq) were added to anhydrous methylene chloride (3 mL), then HATU (56.91 mg, 149.67 μmol, 1.00 eq) was added, and diisopropylethylamine (58.03 mg, 449.01 μmol, 78.21 μL, 3.00 eq) was added dropwisely. The atmosphere was replaced with nitrogen gas three times. The mixture was stirred at 15° C. in a nitrogen atmosphere for 1 hour. The reaction mixture was directly concentrated under reduced pressure, then shaking washed with water (10 mL), and then extracted with ethyl acetate (10 mL×2). The organic phases were washed with a saturated saline solution (15 mL), dried over anhydrous sodium sulfate, filtered and concentrated under reduced pressure. The crude product was purified with a preparative chromatography to give compound 23-4. LCMS (ESI) m/z: 534.1 (M+1). $^1$H NMR (400 MHz, CDCl$_3$) δ ppm 8.66 (br s, 1H), 7.60 (br s, 1H), 7.43 (d, J=8.4 Hz, 2H), 7.30-7.37 (m, 3H), 7.20 (d, J=8.4 Hz, 1H), 5.33-5.64 (m, 1H), 4.61-4.65 (m, 1H), 3.79-3.80 (m, 1H), 3.46-3.51 (m, 1H), 3.06-3.30 (m, 4H), 2.70 (s, 3H), 2.42 (s, 3H), 1.70 (s, 3H).

Synthesis of Compounds 23 and 24

23 or 24

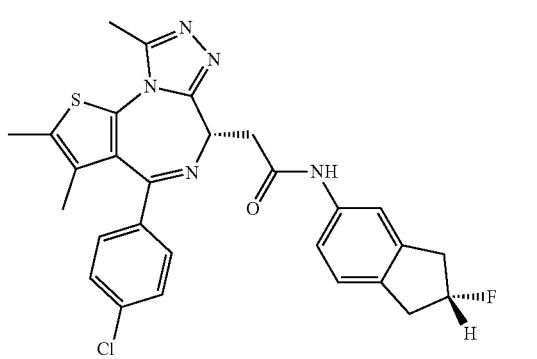

23 or 24

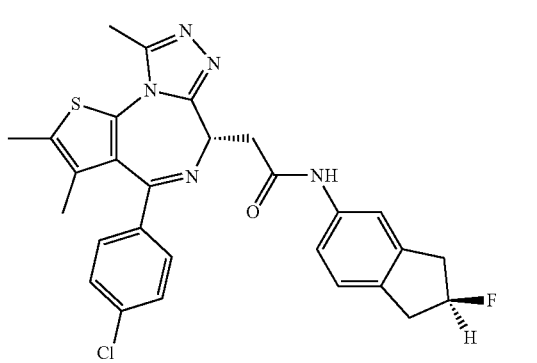

Compound 23-4 (28 mg, 52.43 μmol) was subjected to the SFC separation ((chromatography column: OJ (250 mm×30 mm, 5 μm); mobile phase: [0.1% NH$_3$H$_2$O EtOH]; B %: 30%-30%, 60 mL/min)) to give compound 23 (Rt=5.404 min). LCMS (ESI) m/z: 534.1 (M+1). $^1$H NMR (400 MHz, CDCl$_3$) δppm 8.99 (br s, 1H), 7.50 (s, 1H), 7.23-7.34 (m, 5H), 7.06 (br d, J=8.0 Hz, 1H), 5.36 (d, J=53.2 Hz 1H), 4.58-4.61 (m, 1H), 3.71-3.75 (m, 1H), 3.43-3.47 (m, 1H), 2.78-3.20 (m, 4H), 2.60 (s, 3H), 2.33 (s, 3H), 1.60 (s, 3H).

Compound 24 (Rt=5.702 min). LCMS (ESI) m/z: 534.1 (M+1). $^1$H NMR (400 MHz, CDCl$_3$) δppm 9.00 (s, 1H), 7.52 (s, 1H), 7.20-7.34 (m, 5H), 7.07 (br d, J=8.0 Hz, 1H), 5.36 (d, J=52.0 Hz, 1H), 4.58-4.61 (bm, 1H), 3.65-3.72 (m, 1H), 3.45-3.49 (m, 1H), 3.02-3.31 (m, 4H), 2.60 (s, 3H), 2.33 (s, 3H), 1.60 (s, 3H).

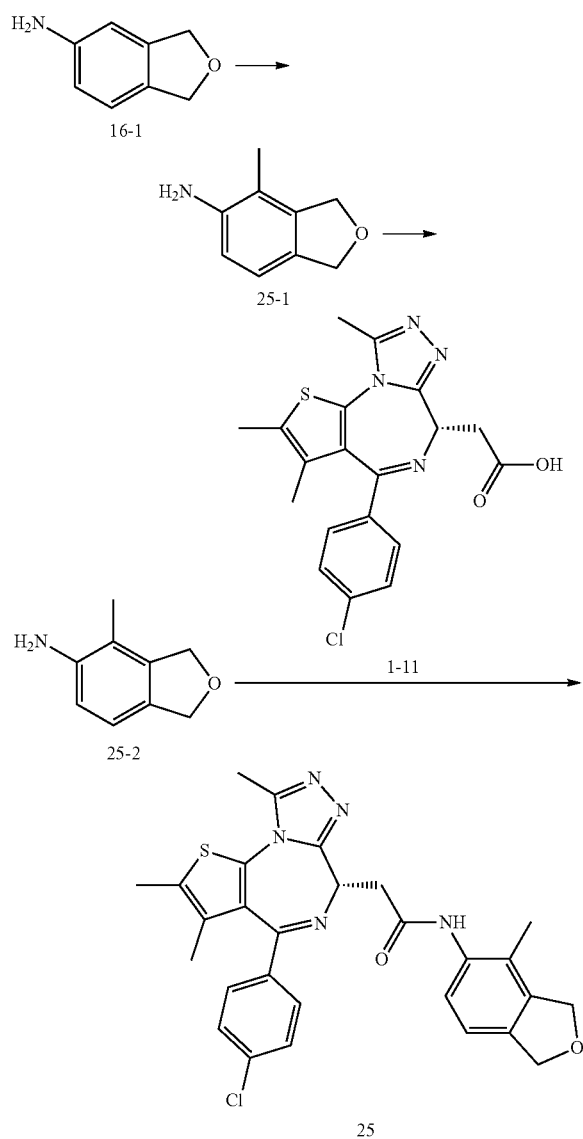

Example 25

Synthesis of Compound 25-1

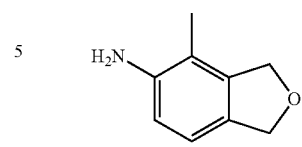

At 15° C. and in a nitrogen atmosphere, to a mixed liquor of compound 16-1 (300 mg, 2.22 mmol, 1 eq), sodium bicarbonate (279.70 mg, 3.33 mmol, 129.49 µL, 1.5 eq) in methylene chloride (10 mL) and methanol (2.5 mL) was added dropwisely iodine chloride (1 M, 2.44 mL, 1.1 eq), and then the mixture was stirred at the same temperature for 4 hours. At 15° C. and under being stirred, to the reaction mixture was added dropwisely a saturated Na$_2$SO$_3$ solution (25 mL), and then the mixture was extracted with methylene chloride (10 mL×2). The organic phase was washed with a saturated saline solution (20 mL), dried over anhydrous sodium sulfate, filtered and concentrated under reduced pressure. The crude product was purified with a flash chromatography column to give compound 25-1. LCMS (ESI) m/z: 261.8 (M+1). $^1$H NMR (400 MHz, CDCl$_3$) δppm 6.88 (d, J=8.0 Hz, 1H), 6.57 (d, J=8.0 Hz, 1H), 5.12 (s, 2H), 4.89 (s, 2H), 4.00 (br s, 2H).

Synthesis of Compound 25-2

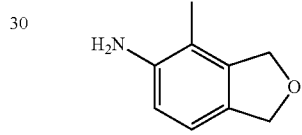

At 15° C., compound 25-1 (140 mg, 489.22 µmol, 1 eq), cesium fluoride (260.10 mg, 1.71 mmol, 63.13 µL, 3.5 eq), [1,1'-bis(diphenylphosphine)ferrocene]palladium (II) dichloride (35.80 mg, 48.92 µmol, 0.1 eq) and methylboronic acid (87.85 mg, 1.47 mmol, 3 eq) were dissolved in dioxane (5 mL), and the mixture was stirred at 80° C. in a nitrogen atmosphere for 4 hours. The reaction mixture was filtered, then shaking washed with water (20 mL), and then extracted with ethyl acetate (10 mL×2). The organic phases were combined, washed with a saturated saline solution (20 mL), dried over anhydrous sodium sulfate, filtered and concentrated under reduced pressure. The crude product was purified with a thin-layer chromatography plate to give compound 25-2. $^1$H NMR (400 MHz, CDCl$_3$) δppm 6.81 (d, J=8.0 Hz, 1H), 6.56 (d, J=8.00 Hz, 1H), 4.99 (s, 4H), 3.52 (br s, 2H), 1.98 (s, 3H).

Synthesis of Compound 25

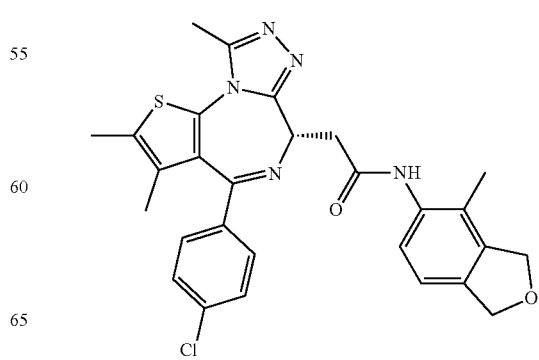

Compound 1-11 (50 mg, 124.73 μmol, 1.00 eq) and compound 25-2 (27.91 mg, 187.09 μmol, 1.5 eq) were dissolved in anhydrous methylene chloride (3 mL), HATU (47.42 mg, 124.73 μmol, 1.00 eq) was added, and diisopropylethylamine (48.36 mg, 374.18 μmol, 65.17 μL, 3.00 eq) was added dropwisely. The mixture was stirred at 15° C. and in a nitrogen atmosphere for 2 hours. The reaction mixture was shaking washed with water (10 mL). The organic phase was washed with a saturated saline solution (20 mL), dried over anhydrous sodium sulfate, filtered and concentrated under reduced pressure. The crude product was purified with a preparative chromatography to give compound 25. LCMS (ESI) m/z: 532.1 (M+1). $^1$H NMR (400 MHz, CDCl$_3$) δppm 8.44 (s, 1H), 7.57 (d, J=7.6 Hz, 1H), 7.35 (d, J=8.4 Hz, 2H), 7.26 (d, J=8.4 Hz, 2H), 6.96 (d, J=8.0 Hz, 1H), 4.99-5.02 (m, 4H), 4.55-4.59 (m, 1H), 3.70-3.75 (m, 1H), 3.45-3.50 (m, 1H), 2.61 (s, 3H), 2.34 (s, 3H), 2.08 (s, 3H), 1.61 (s, 3H).

Scheme 26

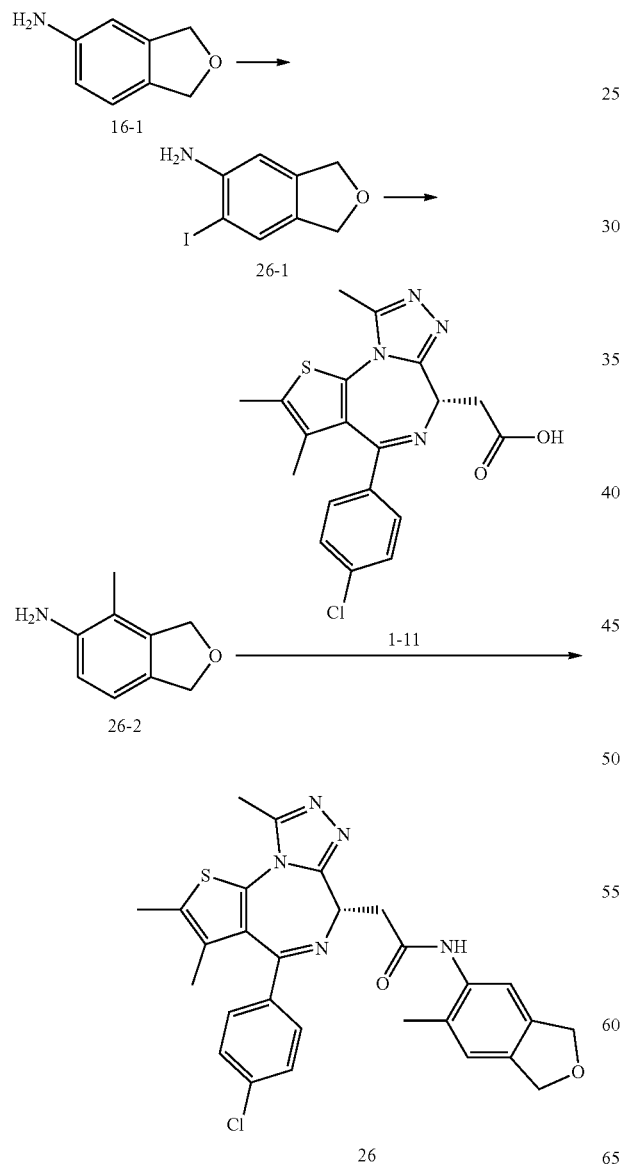

Example 26

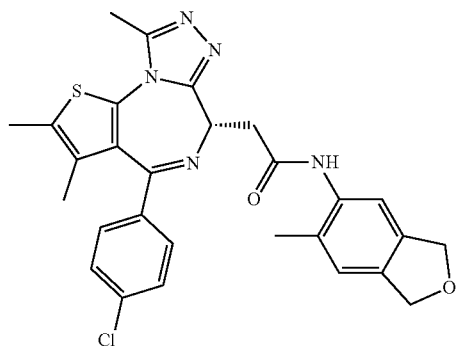 [SMILES: Cc1cc2c(cc1NC(=O)C[C@@H]1N=C(c3ccc(Cl)cc3)c3c(sc(C)c3C)-n3c(C)nnc31)COC2]

Example 26 was synthesized with reference to Example 25.

LCMS (ESI) m/z: 532.1 (M+1). $^1$H NMR (400 MHz, CDCl$_3$) δppm 8.39 (s, 1H), 7.75 (s, 1H), 7.36 (d, J=8.8 Hz, 2H), 7.27 (d, J=8.8 Hz, 2H), 6.97 (s, 1H), 4.98 (d, J=9.6 Hz, 4H), 4.53-4.57 (m, 1H), 3.73-3.78 (m, 1H), 3.42-3.47 (m, 1H), 2.62 (s, 3H), 2.34 (s, 3H), 2.24 (s, 3H), 1.62 (s, 3H).

Scheme 27

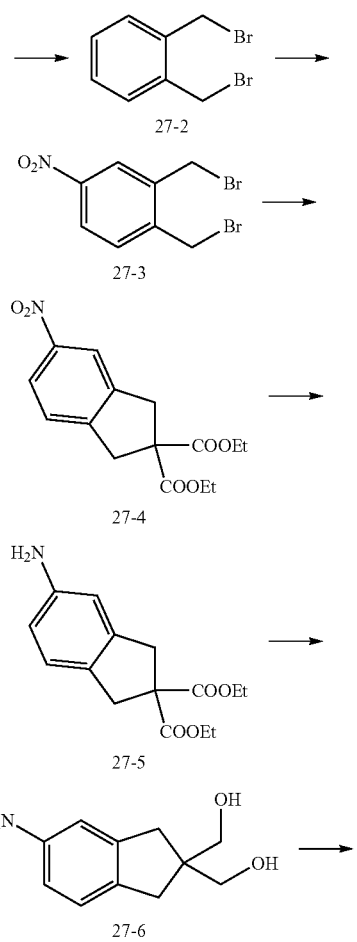

93

-continued

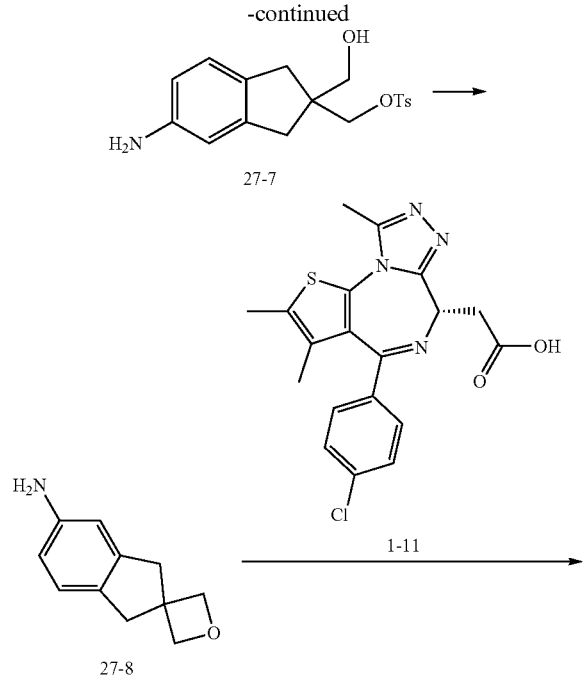

27-7

27-8

Example 27

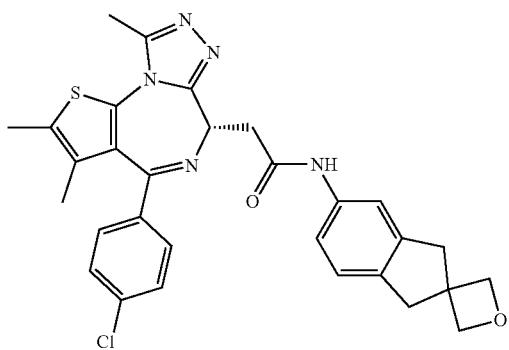 [SMILES: Cc1sc2c(c1C)C(c1ccc(Cl)cc1)=N[C@@H](CC(=O)Nc1ccc3c(c1)CC1(COC1)C3)c1nnc(C)n1-2]

94

Synthesis of Compound 27-2

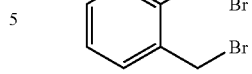

A mixture of ortho-xylene (20.00 g, 188.39 mmol, 22.73 mL, 1.00 eq), NBS (70.41 g, 395.62 mmol, 2.10 eq), benzoyl peroxide (912.70 mg, 3.77 mmol, 0.02 eq) and chloroform (200.00 mL) was stirred at 80° C. for 5 hours. The reaction mixture was cooled to room temperature, then diluted with methylene chloride (200 mL), and washed with water (100 mL×2) and washed with a saturated saline solution (100 mL) respectively. The organic phase was dried over anhydrous sodium sulfate and filtered. The filtrate was concentrated under reduced pressure. The obtained solid was recrystallized at 80° C. with (petroleum ether/ethanol=30:1; 240 mL/8 mL) and cooled to room temperature. A solid precipitated and was filtered. The filter cake washed with petroleum ether (50 mL). The filter cake was oven-dried to give compound 27-2. $^1$H NMR (400 MHz, CDCl$_3$) δppm 7.41-7.35 (m, 2H), 7.35-7.29 (m, 2H), 4.68 (s, 4H).

Synthesis of Compound 27-3

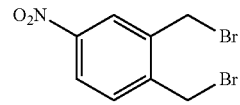 [SMILES: O=[N+]([O-])c1ccc(CBr)c(CBr)c1]

At 0° C., to a solution of compound 27-2 (5 g, 18.94 mmol, 2.55 mL, 1 eq) and concentrated sulphuric acid (30 mL) was added in batch potassium nitrate (2.30 g, 22.73 mmol, 1.2 eq). Then the mixture was stirred at 0° C. for 3 hours. The reaction mixture became red-brown. The reaction mixture was slowly added dropwisely to a 500 mL beaker containing ice cubes (200 g), and a light yellow solid precipitated. Then the mixture was stirred at 0° C. for 1 hour and then filtered. The filter cake was washed with water (100 mL). The filter cake was oven-dried to give compound 27-3, which was directly used in the next step without any further purification. $^1$H NMR (400 MHz, DMSO-d$_6$) δppm 8.39 (d, J=2.5 Hz, 1H), 8.19 (dd, J=2.4, 8.4 Hz, 1H), 7.78 (d, J=8.3 Hz, 1H), 4.94 (s, 2H), 4.90 (s, 2H).

Synthesis of Compound 27-4

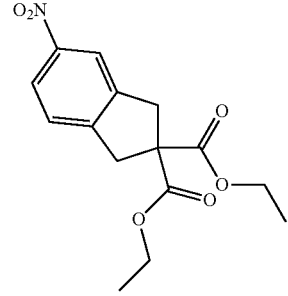 [SMILES: CCOC(=O)C1(C(=O)OCC)Cc2ccc([N+](=O)[O-])cc2C1]

Sodium metal (892.94 mg, 38.84 mmol, 920.56 µL, 2.4 eq) was added to ethanol (20 mL). At 10° C., the mixture was stirred for 0.5 hour until Na completely disappeared. Then a solution of diethyl malonate (3.00 g, 18.73 mmol, 2.83 mL, 1.16 eq) in tetrahydrofuran (10 mL) was added, and a mixed liquor of compound 27-3 (5 g, 16.18 mmol, 1 eq) and tetrahydrofuran (10 mL) was quickly added. Then, the resulting mixture was refluxed at 80° C. under the protection of nitrogen gas for 1 hour. The reaction mixture was concentrated under reduced pressure. Water (60 mL) was added. Then the mixture was extracted with ethyl acetate (50 mL×3). The combined organic phases were washed with a saturated saline solution (50 mL), then dried over anhydrous sodium sulfate and filtered. The filtrate was concentrated under reduced pressure, separated and purified with column chromatography to give compound 27-4. $^1$H NMR (400 MHz, DMSO-d$_6$) δppm 8.13 (s, 1H), 8.06 (dd, J=2.3, 8.3 Hz, 1H), 7.51 (d, J=8.3 Hz, 1H), 4.18-4.13 (m, 4H), 3.59 (s, 4H), 1.19-1.16 (m, 6H).

Synthesis of Compound 27-5

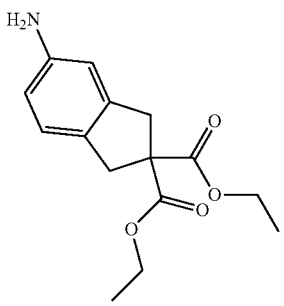

Compound 27-4 (1.3 g, 4.23 mmol, 1 eq) was dissolved in ethanol (20 mL), and then stannous chloride dihydrate (4.77 g, 21.15 mmol, 1.76 mL, 5 eq) was added. The mixture was stirred at 80° C. for 3 hours. The reaction mixture was concentrated under reduced pressure, then adjusted with NaOH solution (4 N) to pH=10, and then extracted with ethyl acetate (40 mL×3). The combined organic phases were washed with a saturated saline solution (50 mL), then dried over anhydrous sodium sulfate and filtered. The filtrate was concentrated under reduced pressure, separated and purified with column chromatography to give compound 27-5. LCMS (ESI) m/z: 277.9 (M+1). $^1$H NMR (400 MHz, CDCl$_3$) δppm 6.97 (d, J=8.0 Hz, 1H), 6.56-6.48 (m, 2H), 4.20 (q, J=7.2 Hz, 4H), 3.62 (br s, 2H), 3.50 (s, 2H), 3.48 (s, 2H), 1.27-1.24 (t, J=7.2 Hz, 6H).

Synthesis of Compound 27-6

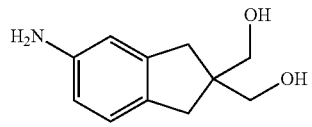 [SMILES: Nc1ccc2c(c1)CC(CO)(CO)C2]

Compound 27-5 (500 mg, 1.80 mmol, 1 eq) was dissolved in tetrahydrofuran (10 mL) at 0° C., and then lithium aluminum hydride (157.39 mg, 4.15 mmol, 2.3 eq) was added. The mixture was stirred at 0° C. for 1 hour. Water (0.2 mL) was added to quench the reaction. Then the mixture was concentrated under reduced pressure, then slurried with ethyl acetate (100 mL) for 10 minutes at 10° C., and filtered. The filter cake was washed with ethyl acetate (50 mL). The filtrate was concentrated under reduced pressure to give compound 27-6, which was directly used in the next step without any further purification.

Synthesis of Compound 27-7

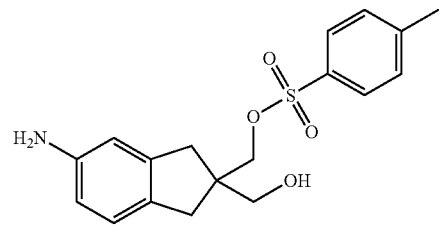 [SMILES: Cc1ccc(S(=O)(=O)OCC2(CO)Cc3ccc(N)cc3C2)cc1]

Compound 27-6 (150 mg, 776.23 μmol, 1 eq) was dissolved in tetrahydrofuran (3 mL). Sodium hydride (46.57 mg, 1.16 mmol, 60% purity, 1.5 eq) was added at 0° C. The mixture was stirred 40 minutes. Then a mixed liquor of para-toluenesulfonyl chloride (147.99 mg, 776.23 μmol, 1 eq) and tetrahydrofuran (3 mL) was added. The mixture was stirred at 0° C. for 40 minutes and then concentrated under reduced pressure to give an oily substance. To the oily substance was added water (50 mL). The mixture was extracted with ethyl acetate (50 mL×3). The combined organic phases were washed with a saturated saline solution (50 mL), then dried over anhydrous sodium sulfate and filtered. The filtrate was concentrated under reduced pressure, and purified with a thin-layer chromatography plate to give compound 27-7. LCMS (ESI) m/z: 348.1 (M+1).

Synthesis of Compound 27-8

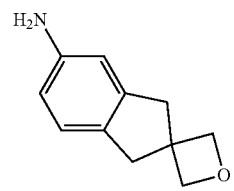

Compound 27-7 (50 mg, 143.91 μmol, 1 eq) was dissolved in tetrahydrofuran (3 mL), and then sodium hydride (57.56 mg, 1.44 mmol, 60% purity, 10 eq) was added. The mixture was stirred at 70° C. for 5 hours. Water (0.5 mL) was added to quench the reaction. The reaction mixture was concentrated under reduced pressure to give an oily substance. To the oily substance was added water (30 mL). The mixture was extracted with (methylene chloride/methanol=10/1) (40 mL×3). The combined organic phases were washed with a saturated saline solution (50 mL), then dried over anhydrous sodium sulfate and filtered. The filtrate was concentrated under reduced pressure, and purified with a thin-layer chromatography plate to give compound 27-8. LCMS (ESI) m/z: 175.9 (M+1). $^1$H NMR (400 MHz, CDCl$_3$) δppm 6.98 (d, J=8.0 Hz, 1H), 6.57 (s, 1H), 6.51 (dd, J=2.1, 7.9 Hz, 1H), 4.67 (s, 4H), 3.62 (br s, 2H), 3.16 (s, 2H), 3.14 (s, 2H).

Synthesis of Compound 27

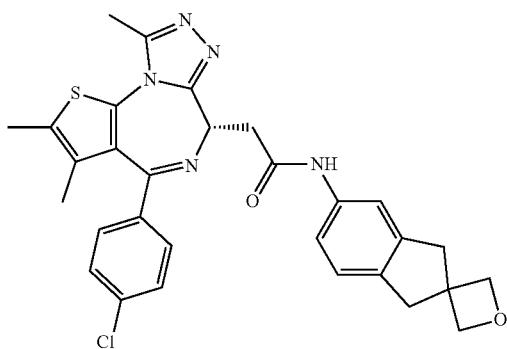 [SMILES: Cc1sc2c(c1C)C(c1ccc(Cl)cc1)=N[C@@H](CC(=O)Nc1ccc3c(c1)CC1(COC1)C3)c1nnc(C)n1-2]

Diisopropylethylamine (58.03 mg, 449.01 μmol, 78.21 μL, 3 eq) was added to a solution of compound 1-11 (0.06 g, 149.67 μmol, 1 eq), compound 27-8 (15.74 mg, 89.80 μmol, 388.88 μL, 0.6 eq) and HATU (62.60 mg, 164.64 μmol, 1.1 eq) in anhydrous methylene chloride (10 mL). The mixture was reacted under being stirred at 15° C. under the protection of nitrogen gas for 1 hour. The reaction mixture was diluted with methylene chloride (10 mL), then successively washed with 1N hydrochloric acid (5 mL), water (5 mL) and a saturated saline solution (10 mL), dried over anhydrous sodium sulfate, filtered, and then concentrated under reduced pressure. The crude product was purified with a preparative chromatography to give compound 27. LCMS (ESI) m/z: 558.1 (M+1). $^1$HNMR (CDCl$_3$ 400 MHz) δppm 8.58 (s, 1H), 7.52 (s, 1H), 7.42 (d, J=8.8 Hz, 2H), 7.33 (d, J=8.8 Hz, 2H), 7.23-7.26 (m, 1H), 7.11-7.23 (m, 1H), 4.66 (s, 4H), 4.58-4.65 (m, 1H), 3.74-3.79 (m, 1H), 3.43-3.48 (m, 1H), 3.21 (s, 2H), 3.18 (s, 2H), 2.67 (s, 3H), 2.40 (s, 3H), 1.69 (s, 3H).

Scheme 28

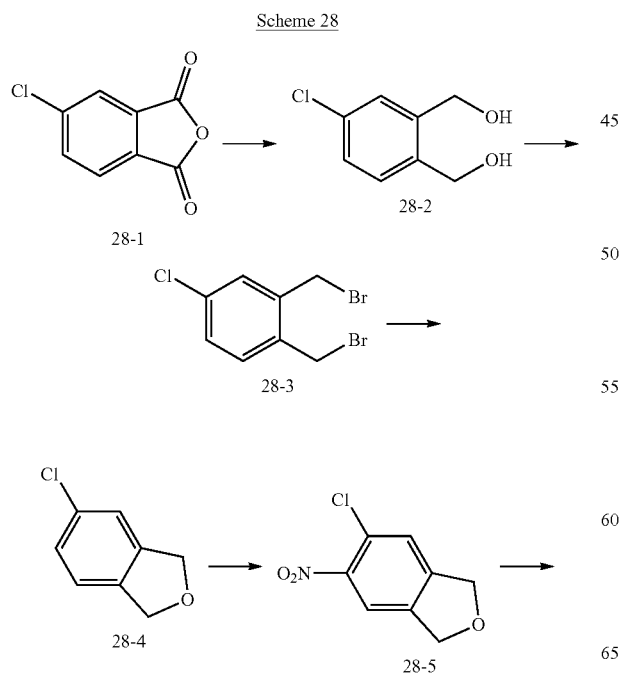

-continued

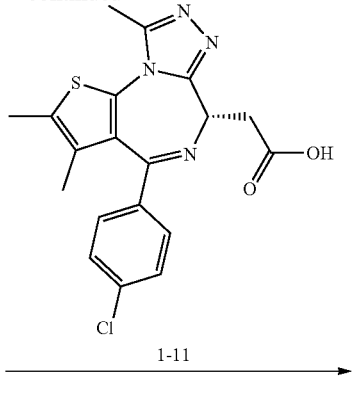

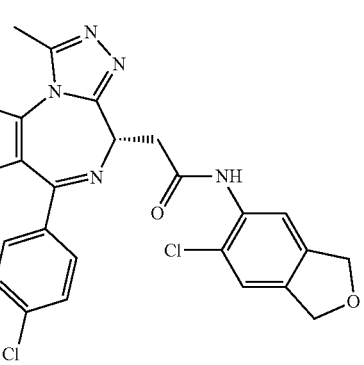

Example 28

Synthesis of Compound 28-2

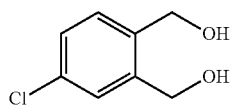 [SMILES: OCc1ccc(Cl)cc1CO]

At 0° C. and under the protection of nitrogen gas, a solution of compound 28-1 (6 g, 32.87 mmol, 1 eq) in tetrahydrofuran (10 mL) was slowly added dropwisely to a suspension of lithium aluminum hydride (2.50 g, 65.76 mmol, 2 eq) and zinc chloride (2.69 g, 19.72 mmol, 923.71 μL, 0.6 eq) in tetrahydrofuran (20 mL). After the completion of the dropwise addition, the mixture was warmed up to 10°

C. and stirred for 6 hours. The reaction mixture was cooled to 0° C. Water (10 mL) was added to quench the reaction (a white precipitate occurred in the quenching process). The mixture was adjusted with an aqueous hydrochloric acid solution (2M) to pH=about 6. The above-mixed solution was extracted with ethyl acetate (3×20 mL) and separated into two phases. The organic phases were combined, then dried over anhydrous sodium sulfate and filtered. The filtrate was concentrated under reduced pressure. The above crude product was added to ethyl acetate (3 mL) and petroleum ether (10 mL). The mixture was heated to 75° C. and stirred under reflux for 30 minutes, and cooled to room temperature. Then petroleum ether (20 mL) was added, and the mixture was stirred for 20 minutes (a white solid precipitated) and filtered. The filter cake was directly oven-dried to give compound 28-2. $^1$H NMR (400 MHz, CDCl$_3$) δppm 7.30 (s, 1H), 7.21-7.22 (m, 2H), 4.63 (s, 4H), 2.76 (br s, 1H), 2.67 (br s, 1H).

Synthesis of Compound 28-3

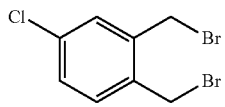

At 0° C. and under the protection of nitrogen gas, phosphorus tribromide (4.70 g, 17.38 mmol, 1.2 eq) was slowly added dropwisely to a solution of compound 28-2 (2.5 g, 14.48 mmol, 1 eq) in methylene chloride (20 mL). After the completion of the dropwise addition, the mixture was warmed up to 10° C., stirred for 5 hours, diluted, and extracted with methylene chloride (3×20 mL). The above organic phases were combined, dried over anhydrous sodium sulfate and filtered. The filtrate was concentrated under reduced pressure. The above crude product was purified with a flash chromatography column to give compound 28-3. $^1$H NMR (400 MHz, CDCl$_3$) δppm 7.30 (d, J=2.4 Hz, 1H), 7.21-7.24 (m, 2H), 4.53 (d, J=8.8 Hz, 4H).

Synthesis of Compound 28-4

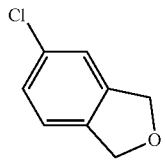

Neutral alumina (30 g, 294.23 mmol, 35.12 eq) was added to a solution of compound 28-3 (2.5 g, 8.38 mmol, 1 eq) in n-hexane (40 mL). The mixture was stirred at 75° C. for 3 hours. The reaction mixture was cooled to 10° C. and filtered. The filtrate was concentrated under reduced pressure. The above crude product was purified with a flash chromatography column to give compound 28-4. $^1$H NMR (400 MHz, CDCl$_3$) δppm 7.22-7.25 (m, 2H), 7.15-7.17 (m, 1H), 5.08 (s, 4H).

Synthesis of Compound 28-5

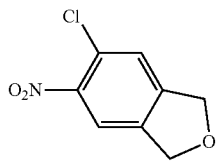

At −10° C., a solution of compound 28-4 (300 mg, 1.94 mmol, 1 eq) in concentrated sulphuric acid (2 mL) was slowly added dropwisely to a solution of potassium nitrate (195.00 mg, 1.93 mmol, 9.94e-1 eq) in concentrated sulphuric acid (6 mL). After the completion of the dropwise addition, the mixture was stirred at −10° C. for 20 minutes. The reaction mixture was poured into ice (about 10 mL). The mixture was stirred for 10 minutes, and extracted with ethyl acetate (3×10 mL). The above organic phases were combined, dried over anhydrous sodium sulfate and filtered. The filtrate was concentrated under reduced pressure. The above crude product was purified with a flash chromatography column to give compound 28-5. $^1$H NMR (400 MHz, CDCl$_3$) δppm 7.78 (s, 1H), 7.44 (s, 1H), 5.15 (s, 4H).

Synthesis of Compound 28-6

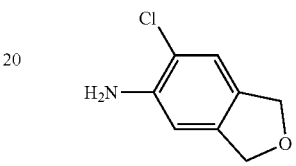

Stannous chloride dihydrate (900 mg, 3.99 mmol, 332.10 μL, 3.98 eq) was added to a solution of compound 28-5 (200 mg, 1.00 mmol, 1.00 eq) in methanol (4 mL). The mixture was stirred at 20° C. for 5 hours. The reaction mixture was directly concentrated under reduced pressure. The above crude product was purified with a thin-layer chromatography plate to give compound 28-6. $^1$H NMR (400 MHz, CD$_3$OD) δppm 7.33 (s, 1H), 7.0-7.06 (m, 1H), 5.01 (m, 4H).

Synthesis of Compound 28

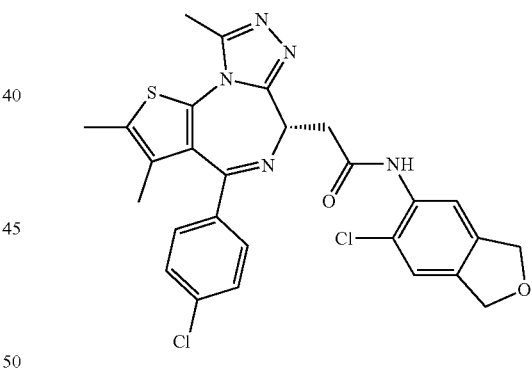

At 0° C., POCl$_3$ (133.87 mg, 873.08 μmol, 81.13 μL, 5 eq) was slowly added dropwisely to a solution of compound 28-6 (40 mg, 235.84 μmol, 1.35 eq) and compound 1-11 (70 mg, 174.62 μmol, 1.00 eq) in pyridine (3 mL). At 0° C. and under the protection of nitrogen gas, the mixture was stirred for 1 hour. Ice water (3 mL) was added to the reaction mixture to quench the reaction. The above-mixed solution was adjusted with a dilute aqueous hydrochloric acid solution (0.5M) to pH=about 6 and extracted with ethyl acetate (3×5 mL). The above organic phases were combined, dried over anhydrous sodium sulfate and filtered. The filtrate was concentrated under reduced pressure. The above crude product was purified with a preparative chromatography to give compound 28. LCMS (ESI) m/z: 552.0 (M+1). $^1$H NMR (400 MHz, CDCl$_3$) δppm 8.71 (s, 1H), 8.22 (s, 1H), 7.36 (d, J=8.4 Hz, 2H), 7.26 (d, J=8.4 Hz, 2H), 7.17 (s, 1H), 4.98 (d, J=4.0 Hz, 4H), 4.58 (t, J=6.8 Hz, 1H), 3.66-3.72 (m, 1H), 3.51-3.57 (m, 1H), 2.62 (s, 3H), 2.34 (s, 3H), 1.62 (s, 3H).

Scheme 29

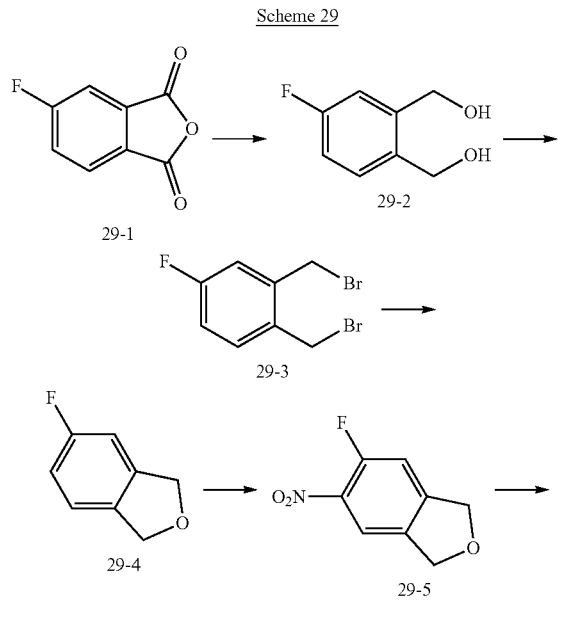

Example 29

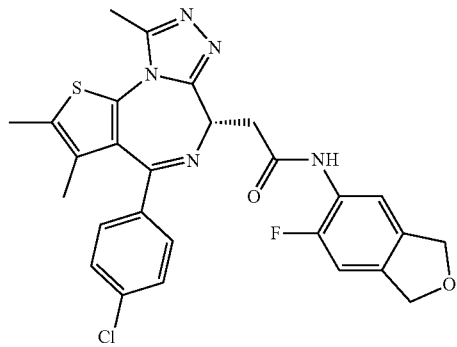

Synthesis of Compound 29-2

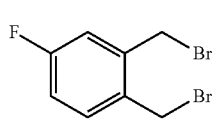

At 0° C. and under the protection of nitrogen gas, a solution of compound 29-1 (5 g, 30.10 mmol, 1 eq) in anhydrous tetrahydrofuran (40 mL) was slowly added to a suspension of lithium aluminum hydride (2.28 g, 60.20 mmol, 2 eq) and zinc chloride (2.46 g, 18.06 mmol, 845.91 µL, 0.6 eq) in anhydrous tetrahydrofuran (100 mL). After the addition, the mixture was reacted at 10° C. for 16 hours. Water (3 mL) was slowly added to the reaction mixture to quench the reaction, and then water (50 mL) was added to the reaction mixture. The aqueous phase was extracted with ethyl acetate (50 mL×2). The organic phases were combined, dried over anhydrous sodium sulfate, filtered, and then concentrated under reduced pressure to give compound 29-2, which was directly used in the next step without purification. $^1$H NMR (400 MHz, CDCl$_3$) δppm 7.21-7.23 (m, 1H), 6.93-7.03 (m, 2H), 4.53-4.55 (m, 4H).

Synthesis of Compound 29-3

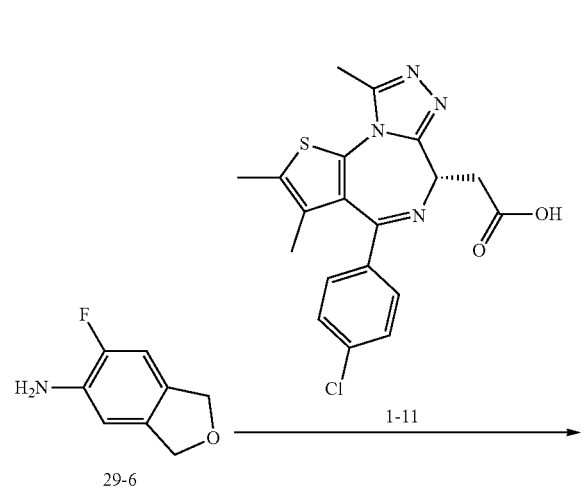

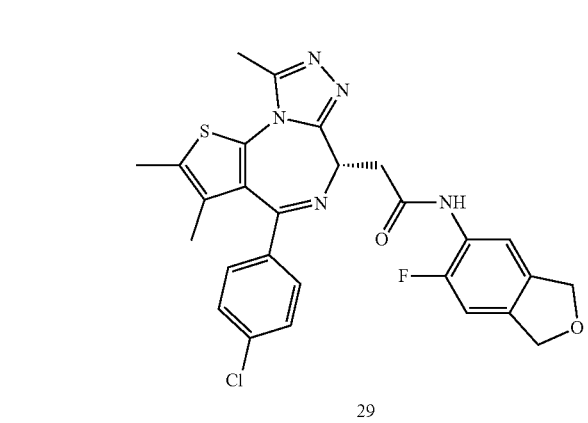

At 0° C. and under the protection of nitrogen gas, phosphorus tribromide (7.76 g, 28.66 mmol, 1.2 eq) was slowly added to a solution of compound 29-2 (3.73 g, 23.89 mmol, 1 eq) in anhydrous methylene chloride (100 mL). After the addition, the mixture was reacted at 10° C. under the protection of nitrogen gas for 6 hours. The reaction mixture was washed with water (50 mL). The organic phase was dried over anhydrous sodium sulfate and filtered and concentrated under reduced pressure. The crude product was purified with a flash chromatography column to give compound 29-3.

Synthesis of Compound 29-4

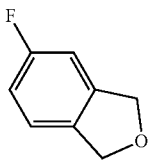

Neutral alumina (40 g, 392.31 mmol, 29.89 eq) was added to a solution of compound 29-3 (3.7 g, 13.12 mmol, 1 eq) in n-hexane (80 mL). After the addition, the mixture was reacted at 75° C. for 20 hours. The reaction mixture was cooled to 50° C., and the insoluble substance was filtered off while hot. Then the filter cake was washed with methylene chloride (50 mL). The filtrates were combined and evaporated to dryness under reduced pressure to give compound 29-4, which was directly used in the next step without purification. $^1$H NMR (400 MHz, CDCl$_3$) δppm 7.07-7.09 (m, 1H), 6.84-6.90 (m, 2H), 5.00 (s, 4H).

Synthesis of Compound 29-5

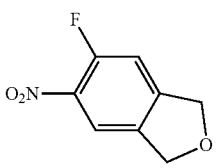 [SMILES: O=[N+]([O-])c1cc2c(cc1F)COC2]

Potassium nitrate (878.27 mg, 8.69 mmol, 1 eq) was added to a solution of concentrated sulphuric acid (10 mL). Compound 29-4 (1.2 g, 8.69 mmol, 1 eq) was dissolved in concentrated sulphuric acid (5 mL) that was cooled down at −10° C. in an iced salt bath, and then added to the above reaction mixture in an iced salt bath. After the addition, the mixture was reacted at −10° C. in an iced salt bath for 30 minutes. The reaction mixture was slowly added dropwisely to the continuously stirred crushed ice (100 mL). The mixture was filtered to give a light brown solid as a crude product. The crude product was dissolved in ethyl acetate (50 mL). Then the mixture was dried over anhydrous sodium sulfate, filtered, and then concentrated under reduced pressure to give compound 29-5, which was directly used in the next step without any further purification. $^1$H NMR (400 MHz, CDCl$_3$) δppm 8.71 (d, J=1.6 Hz, 1H), 8.51 (dd, J=2.0, 8.4 Hz, 1H), 7.65 (d, J=8.4 Hz, 1H), 5.38 (s, 4H).

Synthesis of Compound 29-6

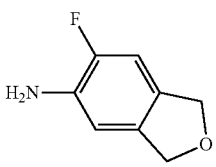

Compound 29-5 (0.183 g, 999.25 μmol, 1 eq) and stannous chloride dihydrate (901.91 mg, 4.00 mmol, 332.81 μL, 4 eq) were added to absolute methanol (5 mL). After the addition, the mixture was reacted at 30° C. for 4 hours. The reaction mixture was directly concentrated under reduced pressure. The residue was dissolved in ethyl acetate (50 mL). The insoluble substance was filtered off. The filtrate was dried over anhydrous sodium sulfate, filtered, and then concentrated under reduced pressure to give compound 29-6, which was directly used in the next step without any further purification. LCMS (ESI) m/z: 153.9 (M+1).

Synthesis of Compound 29

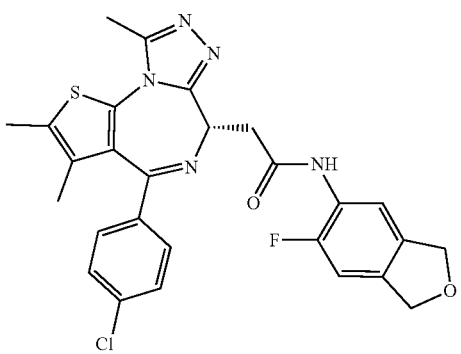 [SMILES: Cc1sc2c(c1C)C(c1ccc(Cl)cc1)=N[C@@H](CC(=O)Nc1cc3c(cc1F)COC3)c1nnc(C)n1-2]

At 0° C. and under the protection of nitrogen gas, POCl$_3$ (71.27 mg, 464.83 μmol, 43.20 μL, 2 eq) was added to a solution of compound 1-11 (100 mg, 232.41 μmol, 1 eq) and compound 29-6 (42.71 mg, 278.90 μmol, 1.2 eq) in pyridine (2 mL). After the addition, the mixture was reacted at 15° C. for 2 hours. Water (5 mL) was added to the reaction mixture. The aqueous phase was adjusted with hydrochloric acid to pH=7 and extracted with methylene chloride (5 mL×3). The organic phases were combined, dried over anhydrous sodium sulfate, filtered, then concentrated under reduced pressure, and purified with a thin-layer chromatography plate to give compound 29. LCMS (ESI) m/z: 536.1 (M+1). $^1$H NMR (400 MHz, CDCl$_3$) δppm 8.80 (br s, 1H), 8.13 (d, J=6.8 Hz, 1H), 7.36 (d, J=8.4 Hz, 2H), 7.26 (d, J=8.8 Hz, 2H), 6.88 (d, J=10.0 Hz, 1H), 4.97 (s, 4H), 4.5-4.57 (m, 1H), 3.64-3.66 (m, 1H), 3.52-3.54 (m, 1H), 2.61 (s, 3H), 2.34 (s, 3H), 1.62 (s, 3H).

Scheme 30

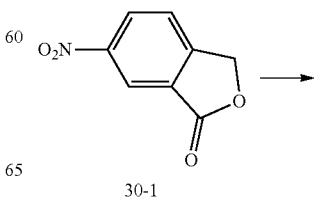

30-1

-continued

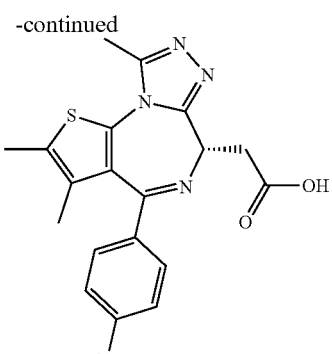
1-11

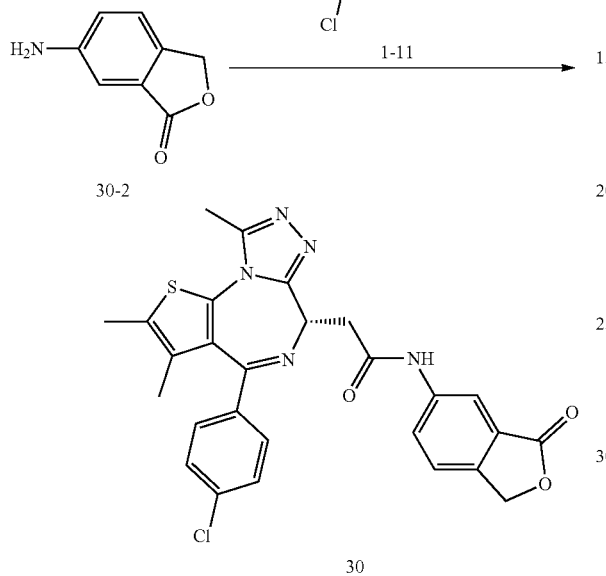
30-2

30

Example 30

Synthesis of Compound 30-2

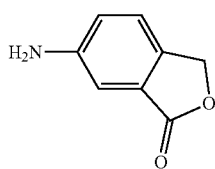

Compound 30-1 (0.5 g, 2.79 mmol, 1 eq) and Pd/C (0.5 g, 10% purity) were added to methanol (5 mL). After the addition, the atmosphere was replaced with a balloon filled with hydrogen gas for 3 times. Then the mixture was reacted at 20° C. under the protection of hydrogen balloon (15 psi) for 12 hours. The insoluble substance was filtered off. The filtrate was concentrated under reduced pressure. The residue was dissolved in methylene chloride (50 mL). The mixture was filtered to obtain a filtrate. Then the filtrate was concentrated under reduced pressure to give compound 30-2, which was directly used in the next step without any further treatment. $^1$H NMR (400 MHz, CD$_3$OD) δppm 7.19 (d, J=9.2 Hz, 1H), 6.96-6.98 (m, 2H), 5.12 (s, 3H).

Synthesis of Compound 30

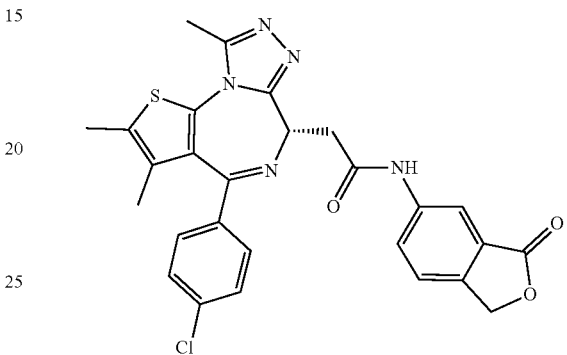

Compound 1-11 (0.1 g, 232.41 μmol, 1 eq), compound 30-2 (52.00 mg, 348.62 μmol, 1.5 eq) and HATU (106.04 mg, 278.90 μmol, 1.2 eq) were added to anhydrous N,N-dimethyl formamide (2 mL). Then diisopropylethylamine (60.08 mg, 464.83 μmol, 80.96 μL, 2 eq) was added to the above solution at 20° C. After the addition, the mixture was reacted at 20° C. for 12 hours. Water (5 mL) was added to the reaction mixture. The resulting mixture was extracted with methylene chloride (5 mL×3). The organic phase was concentrated under reduced pressure. Then water (10 mL) was added. The mixture was lyophilized to remove the residual N,N-dimethyl formamide, and purified with a preparative chromatography to give compound 30. LCMS (ESI) m/z: 532.1 (M+1). $^1$H NMR (400 MHz, CDCl$_3$) δppm 9.65 (br s, 1H), 8.09 (d, J=6.8 Hz, 1H), 7.68 (d, J=8.0 Hz, 1H), 7.33-7.35 (m, 2H), 7.24-7.27 (m, 3H), 5.15 (s, 2H), 4.62-4.66 (m, 1H), 3.80-3.86 (m, 1H), 3.46-3.51 (m, 1H), 2.64 (s, 3H), 2.35 (s, 3H), 1.63 (s, 3H).

Scheme 31

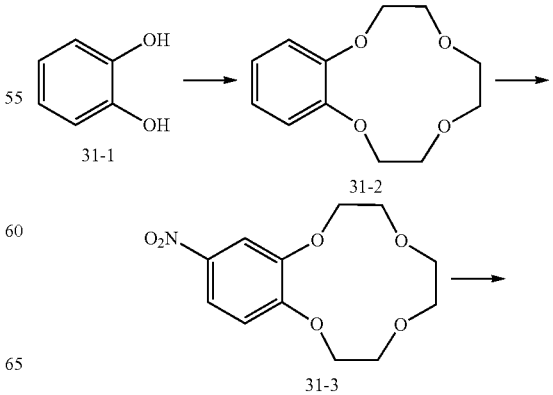

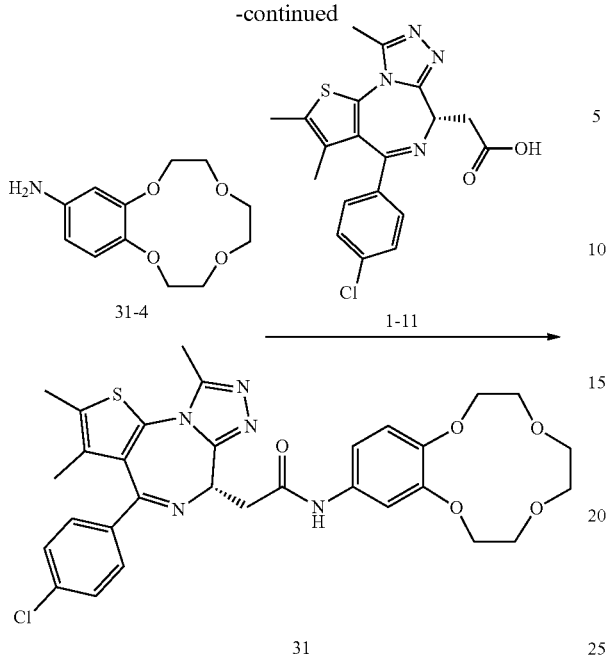

Example 31

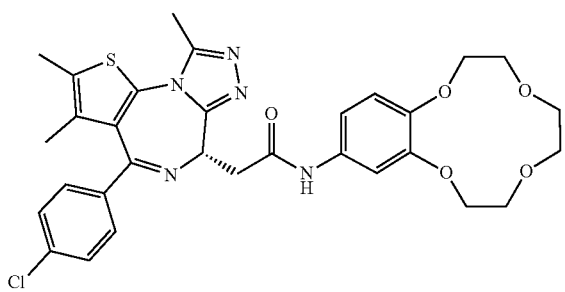 [SMILES: Cc1sc2c(c1C)C(c1ccc(Cl)cc1)=N[C@@H](CC(=O)Nc1ccc3c(c1)OCCOCCOCCO3)c1nnc(C)n1-2]

Synthesis of Compound 31-2

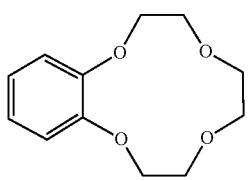 [SMILES: c1ccc2c(c1)OCCOCCOCCO2]

At 20° C. and under the protection of nitrogen gas, to a constantly stirred solution of compound 31-1 (0.5 g, 4.54 mmol, 757.58 μL, 1 eq) dissolved in n-butyl alcohol (10 mL) was added dropwisely a solution of lithium bromide monohydrate (1.19 g, 11.35 mmol, 2.5 eq) and lithium hydroxide monohydrate (400.16 mg, 9.53 mmol, 2.1 eq) dissolved in water (1 mL). After the completion of the dropwise addition, the reaction mixture was warmed up to 110° C. and stirred for 0.1 hours. Then 1,2-di(2-chloroethoxy)ethane (849.27 mg, 4.54 mmol, 532.29 μL, 1 eq) was added. The stirring at the same temperature was kept on for 5 hours. The reaction mixture was adjusted with concentrated HCl to pH=4, and then directly concentrated under reduced pressure. To the residue were added methylene chloride (50 mL) and water (30 mL). The mixture was stirred for 0.5 hour and separated into two phases. The organic phase was washed with a saturated saline solution (30 mL), dried over anhydrous sodium sulfate, filtered, and then concentrated under reduced pressure. The compound as a crude product was purified with a flash chromatography column to give compound 31-2. $^1$H NMR (400 MHz, CDCl$_3$) δppm 6.89-6.90 (m, 4H), 4.09-4.11 (m, 4H), 3.73-3.79 (m, 8H).

Synthesis of Compound 31-3

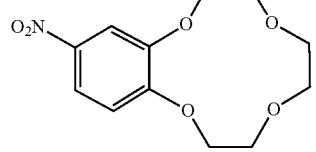

A solution of compound 31-2 (50 mg, 222.96 μmol, 1 eq) in acetonitrile (2 mL) was warmed up to 85° C. Concentrated nitric acid (38 mg, 337.71 μmol, 27.14 μL, 56% purity, 1.51 eq) was slowly added dropwisely. After the completion of the dropwise addition, the mixture was stirred at 85° C. for 0.5 hour. The reaction mixture was cooled to room temperature and poured into ice (about 10 mL) to quench the reaction. The mixture was extracted with ethyl acetate (3×10 mL). The above organic phases were combined, dried over anhydrous sodium sulfate and filtered. The filtrate was concentrated under reduced pressure to give compound 31-3, which was directly used in the next step without the need for any further purification. $^1$H NMR (400 MHz, CDCl$_3$) δppm 7.86-7.89 (m, 1H), 7.81 (d, J=2.8 Hz, 1H), 6.93 (d, J=8.8 Hz, 1H), 4.17-4.23 (m, 4H), 3.84-3.85 (m, 2H), 3.77-3.80 (m, 2H), 3.71 (s, 4H).

Synthesis of Compound 31-4

Wet Pd/C (50 mg, 10% purity) was added to a solution of compound 31-3 (50 mg, 185.70 μmol, 1.00 eq) in methanol (10 mL). The atmosphere was replaced with hydrogen gas three times. The mixture was stirred at 15° C. at a hydrogen balloon (15 psi) condition for 2 hours. The reaction mixture was filtered with diatomaceous earth. The filtrate was directly concentrated under reduced pressure to give compound 31-4, which was directly used in the next step without the need for any further purification. $^1$H NMR (400 MHz, CDCl$_3$) δppm 6.75 (d, J=8.4 Hz, 1H), 6.26 (d, J=2.4 Hz, 1H), 6.18 (dd, J=8.4, 2.4 Hz, 1H), 3.98-4.05 (m, 4H), 3.75-3.84 (m, 2H), 3.71 (s, 6H), 3.27 (br s, 2H).

Synthesis of Compound 31

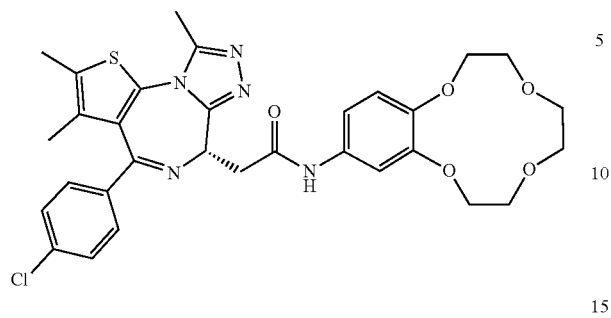

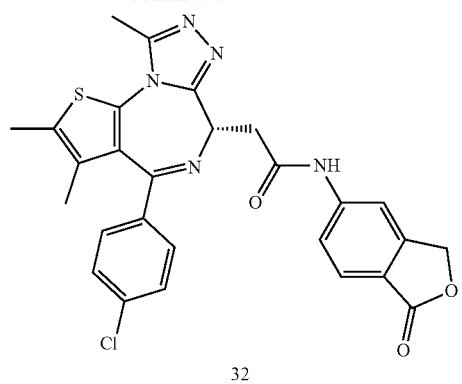

Compound 1-11 (35 mg, 87.31 μmol, 1.00 eq) and compound 31-4 (25 mg, 104.49 μmol, 1.20 eq) were successively added to a solution of HATU (35.00 mg, 92.05 μmol, 1.05 eq) in anhydrous methylene chloride (2 mL), and then triethylamine (29.08 mg, 287.38 μmol, 40 μL, 3.29 eq) was slowly added dropwisely. The mixture was stirred at 10° C. under the protection of nitrogen gas for 6 hours. Water (3 mL) was added to the reaction mixture to quench the reaction. The mixture was extracted with methylene chloride (3×5 mL), and the above organic phases were combined, dried over anhydrous sodium sulfate and filtered. The filtrate was concentrated under reduced pressure. The above crude product was purified with a preparative chromatography to give compound 31. LCMS (ESI) m/z: 622.1 (M+1). $^1$H NMR (400 MHz, CDCl$_3$) δppm 8.82 (m, 1H), 7.23-7.38 (m, 5H), 6.92-6.94 (m, 1H), 6.81-6.83 (m, 1H), 4.57-4.59 (m, 1H), 3.97-4.15 (m, 4H), 3.70-3.80 (m, 9H), 3.43-3.45 (m, 1H), 2.61 (s, 3H), 2.34 (s, 3H), 1.61 (s, 3H).

Scheme 32

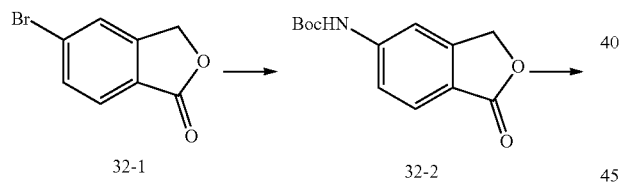

Example 32

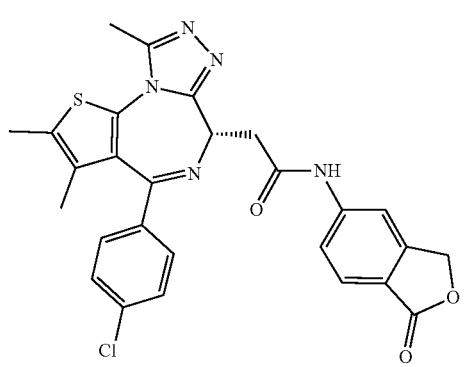 [SMILES: Cc1sc2c(c1C)C(c1ccc(Cl)cc1)=N[C@@H](CC(=O)Nc1ccc3c(c1)COC3=O)c1nnc(C)n1-2]

Synthesis of Compound 32-2

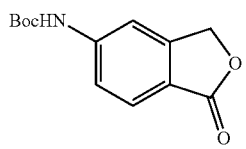 [SMILES: CC(C)(C)OC(=O)Nc1ccc2c(c1)COC2=O]

Compound 32-1 (0.78 g, 3.66 mmol, 1 eq), tert-butyl carbamate (643.39 mg, 5.49 mmol, 1.5 eq), tris(dibenzylideneacetone) dipalladium (335.29 mg, 366.15 μmol, 0.1 eq), cesium carbonate (2.39 g, 7.32 mmol, 2 eq) and 4,5-bis(diphenylphosphine)-9,9-dimethylxanthene (211.86 mg, 366.15 μmol, 0.1 eq) were added to 1,4-dioxane (10 mL). After the addition, the mixture was reacted at 100° C. under the protection of nitrogen gas for 12 hours. To the reaction mixture was added water (20 mL) and then ethyl acetate (20 mL). The insoluble substance was filtered off. Then the aqueous phase was extracted with ethyl acetate (10 mL). The organic phases were combined, dried over anhydrous sodium sulfate, filtered, then concentrated under reduced pressure, and purified with a flash chromatography column to give compound 32-2. LCMS (ESI) m/z: 250.1 (M+1).

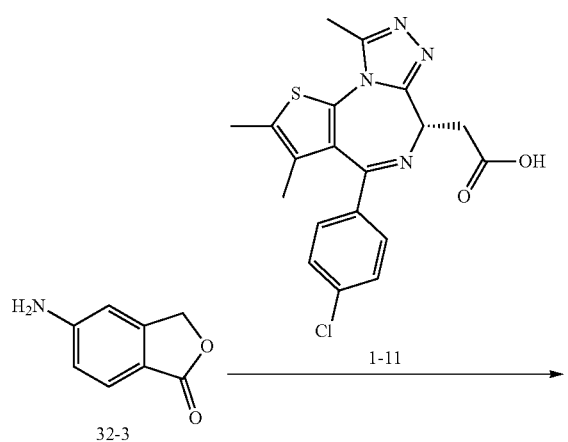

Synthesis of Compound 32-3

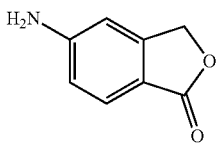

Trifluoroacetic acid (3.85 g, 33.77 mmol, 2.5 mL, 18.30 eq) was added to compound 32-2 (0.46 g, 1.85 mmol, 1 eq) in anhydrous methylene chloride (20 mL). After the addition, the mixture was reacted at 20° C. for 12 hours. The reaction mixture was washed with water (20 mL). The aqueous phase was adjusted with a saturated sodium bicarbonate solution to pH=7 and then extracted with methylene chloride (10 mL×2). The organic phases were combined, dried over anhydrous sodium sulfate, filtered, and then concentrated under reduced pressure to give compound 32-3, which was directly used in the next step without any further purification. LCMS (ESI) m/z: 149.8 (M+1).

Synthesis of Compound 32

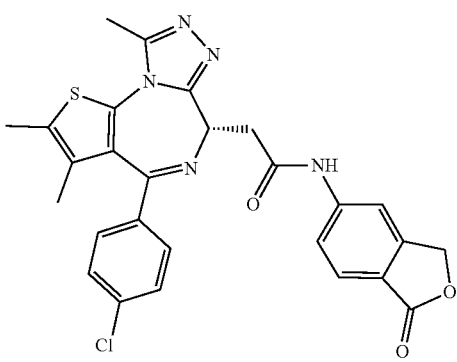 [SMILES: Cc1sc2c(c1C)C(c1ccc(Cl)cc1)=N[C@@H](CC(=O)Nc1ccc3c(c1)COC3=O)c1nnc(C)n1-2]

At 0° C., POCl$_3$ (76.50 mg, 498.90 µmol, 46.36 µL, 2 eq) was added to a solution of compound 1-11 (100 mg, 249.45 µmol, 1 eq) and compound 32-3 (44.65 mg, 299.34 µmol, 1.2 eq) in pyridine (2 mL). After the addition, the mixture was warmed up to 20° C. and reacted for 1.5 hours. Water (3 mL) was added to the reaction mixture to quench the reaction. Then the aqueous phase was adjusted with hydrochloric acid (2N) to pH=7. The aqueous phase was extracted with methylene chloride (5 mL×3). The organic phase was dried over anhydrous sodium sulfate, filtered, then concentrated under reduced pressure, and purified with a preparative thin layer chromatography plate to give compound 32. LCMS (ESI) m/z: 532.1 (M+1). $^1$H NMR (400 MHz, CDCl$_3$) δppm 9.98 (br s, 1H), 7.94 (d, J=6.8 Hz, 1H), 7.67 (d, J=8.0 Hz, 1H), 7.32-7.36 (m, 3H), 7.24-7.27 (m, 2H), 5.08-5.16 (m, 2H), 4.57-4.61 (m, 1H), 3.78-3.84 (m, 1H), 3.45-3.50 (m, 1H), 2.63 (s, 3H), 2.36 (s, 3H), 1.63 (s, 3H).

Scheme 33

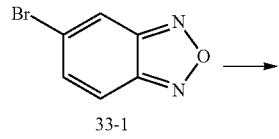

-continued

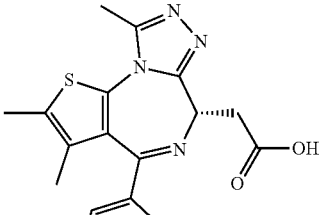

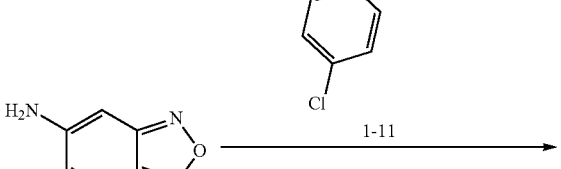

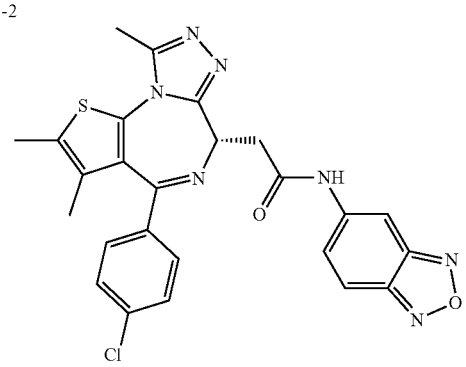

Example 33

Synthesis of Compound 33-2

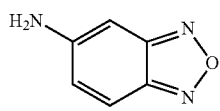

Compound 33-1 (0.5 g, 2.51 mmol, 1 eq), CuO (19.99 mg, 251.25 µmol, 3.16 µL, 0.1 eq) and cuprous iodide (478.51 mg, 2.51 mmol, 1 eq) was added to concentrated ammonia water (5.46 g, 155.80 mmol, 6 mL, 62.01 eq). To the obtained solution was added dropwisely a few drops of N-methyl pyrrolidone. In a microwave synthesis instrument,

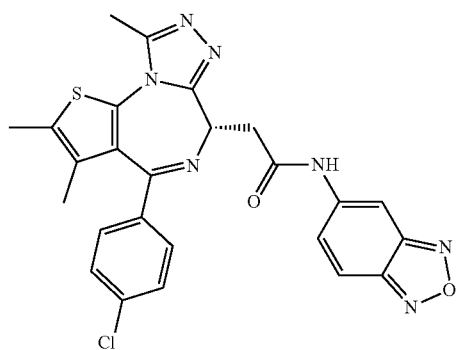 [SMILES: Cc1sc2c(c1C)C(c1ccc(Cl)cc1)=N[C@@H](CC(=O)Nc1ccc3nonc3c1)c1nnc(C)n1-2]

the reaction was carried out at 140° C. for 0.5 hour and then at 150° C. for 1 hour. To the reaction mixture was added water (10 mL) to dilute the reaction mixture, and then methylene chloride (10 mL) was added. The resulting mixture was filtered to remove the insoluble substance. The aqueous phase was extracted with methylene chloride (10 mL×2). The organic phase was dried over anhydrous sodium sulfate, filtered, and then concentrated under reduced pressure to give compound 33-2, which was directly used in the next step without any further purification. LCMS (ESI) m/z: 136.0 (M+1). $^1$H NMR (400 MHz, CDCl$_3$) δppm 7.55 (d, J=9.6 Hz, 1H), 7.67 (dd, J=2.0, 9.6 Hz, 1H), 6.50 (s, 1H), 4.63 (br s, 2H).

Synthesis of Compound 33

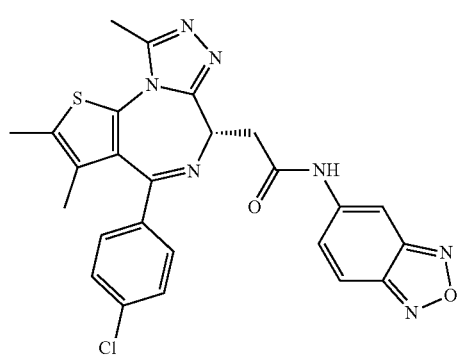 [SMILES: Cc1sc2c(c1C)C(c1ccc(Cl)cc1)=N[C@@H](CC(=O)Nc1ccc3nonc3c1)c1nnc(C)n1-2]

At 0° C. and under the protection of nitrogen gas, POCl$_3$ (35.64 mg, 232.41 μmol, 21.60 μL, 2 eq) was added to a solution of compound 1-11 (50 mg, 116.21 μmol, 1 eq) and compound 33-2 (23.55 mg, 174.31 μmol, 1.5 eq) in pyridine (1 mL). After the addition, the mixture was reacted at 20° C. for 2 hours. Water (2 mL) was added to the reaction mixture to quench the reaction. Then the aqueous phase was adjusted with 2N HCl to pH=7. The aqueous phase was extracted with methylene chloride (5 mL×3). The organic phase was dried over anhydrous sodium sulfate, filtered, then concentrated under reduced pressure, purified with a preparative chromatography to give compound 33. LCMS (ESI) m/z: 518.1 (M+1). $^1$H NMR (400 MHz, CDCl$_3$) δppm 9.87 (br s, 1H), 8.33 (s, 1H), 7.60 (d, J=9.2 Hz, 1H), 7.37 (d, J=8.8 Hz, 2H), 7.27 (d, J=8.8 Hz, 2H), 7.16-7.17 (m, 1H), 4.55-4.58 (m, 1H), 3.76-3.82 (m, 1H), 3.44-3.48 (m, 1H), 2.64 (s, 3H), 2.36 (s, 3H), 1.64 (s, 3H).

Schemes 34 and 35

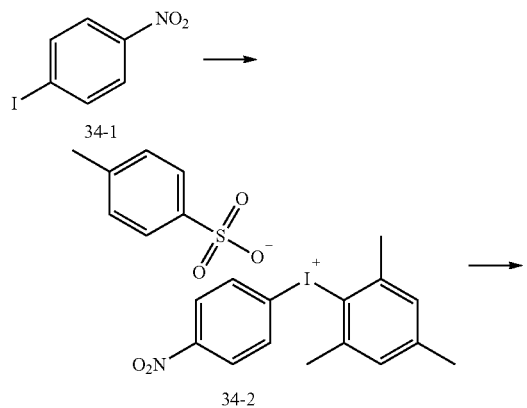

34-1

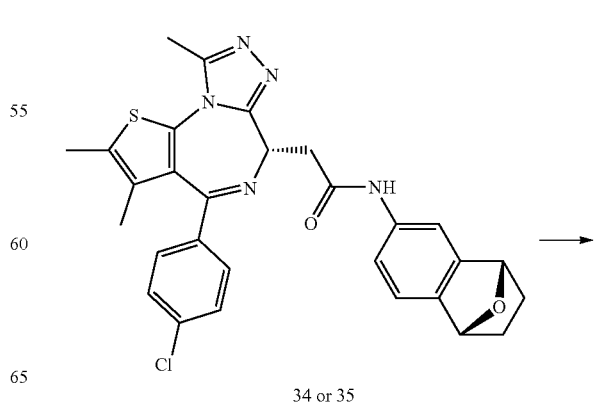

34-2

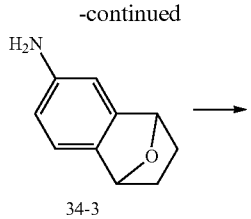

34-3

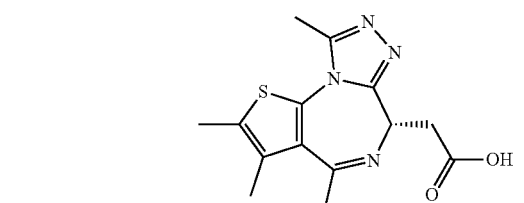

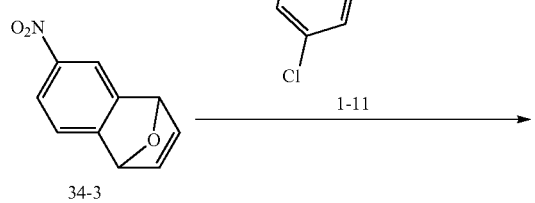

34-3
1-11

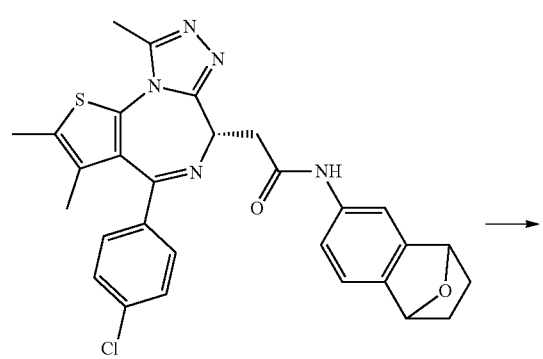

34-5

34 or 35

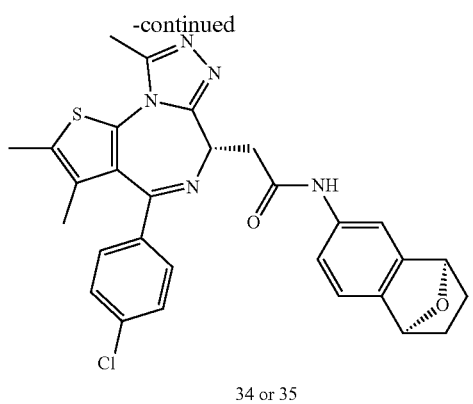

34 or 35

Examples 34 and 35

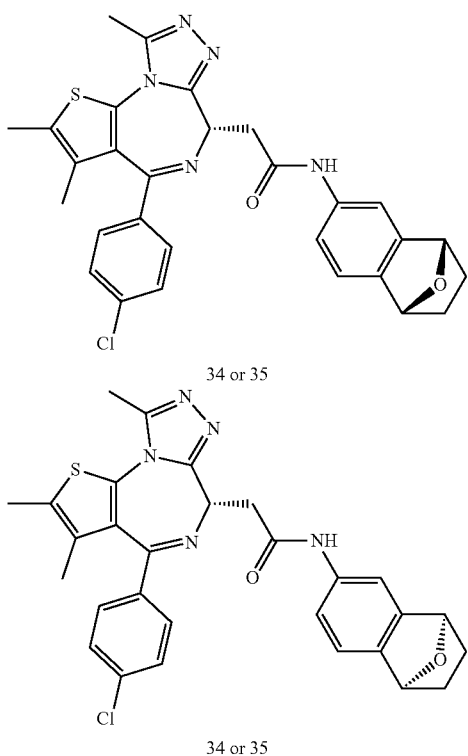

34 or 35

34 or 35

Synthesis of Compound 34-2

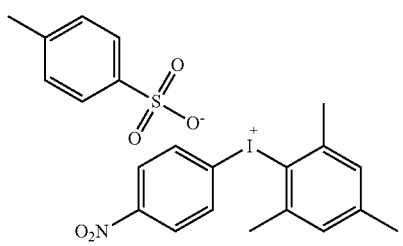

3-chloroperbenzoic acid (3.09 g, 15.23 mmol, 85% purity) was added to a solution of compound 34-1 (4.45 g, 17.89 mmol, 1 eq) and p-toluenesulfonic acid monohydrate (3.43 g, 18.01 mmol, 1.01 eq) in acetonitrile (25 mL). The resulting mixture was warmed up to 77° C. and stirred for 30 minutes. Then 1,3,5-trimethylbenzene (2.16 g, 17.99 mmol, 2.5 mL, 1.01 eq) was slowly added dropwisely. After the completion of the dropwise addition, the resulting mixture was stirred at 77° C. for 3 hours. The reaction mixture was cooled to room temperature, and concentrated under reduced pressure. The residue was washed with petroleum ether (20 mL) and filtered. The filter cake was oven-dried to give compound 34-2, which was directly used in the next step without any further purification. $^1$H NMR (400 MHz, DMSO-$d_6$) δppm 8.24 (d, J=9.2 Hz, 1H), 8.17 (d, J=8.8 Hz, 1H), 8.06 (d, J=8.8 Hz, 2H), 7.97 (d, J=8.8 Hz, 2H), 7.49 (d, J=8.0 Hz, 2H), 7.12 (d, J=8.8 Hz, 2H), 2.58 (s, 3H), 2.51 (s, 9H).

Synthesis of Compound 34-3

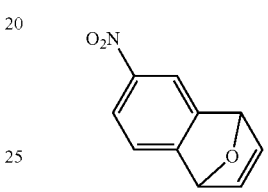

At 0° C. and under the protection of nitrogen gas, furan (5.60 g, 82.26 mmol, 5.98 mL, 5.55 eq) was added dropwisely to a solution of compound 34-2 (8 g, 14.83 mmol, 1 eq) in toluene (20 mL), and then lithium bis(trimethylsilyl) amide (1 M, 14.82 mL) was slowly added dropwisely. After the completion of the dropwise addition, the mixture was stirred at 0° C. under the protection of nitrogen gas for 3 hours. The reaction mixture was cooled to 0° C., and a saturated ammonium chloride solution (4 mL) was added to quench the reaction. The mixture was extracted with ethyl acetate (3×5 mL). The above organic phases were combined, dried over anhydrous sodium sulfate and filtered. The filtrate was concentrated under reduced pressure. The above crude product was purified with a flash chromatography column to give compound 34-3. $^1$H NMR (400 MHz, CDCl$_3$) δppm 8.21 (s, 1H), 8.19 (s, 1H), 7.48-7.50 (m, 1H), 7.11-7.13 (m, 1H), 7.06-7.08 (m, 1H), 5.82-5.84 (m, 2H).

Synthesis of Compound 34-4

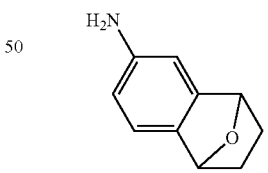

Under the protection of nitrogen gas, a solution of sodium borohydride (12.00 mg, 317.18 μmol, 1 eq) in water (1 mL) was slowly added dropwisely to a suspension of compound 34-3 (60 mg, 317.18 μmol, 1 eq) and Pd/C (5 mg, 10% purity) in methanol (2 mL). The mixture was stirred at 25° C. under the protection of nitrogen gas for 1 hour. The reaction mixture was filtered with a funnel containing diatomaceous earth. The filtrate was directly concentrated under reduced pressure to give compound 34-4, which was directly used in the next step without the need for any further purification. LCMS (ESI) m/z: 162.1 (M+1).

Synthesis of Compound 34-5

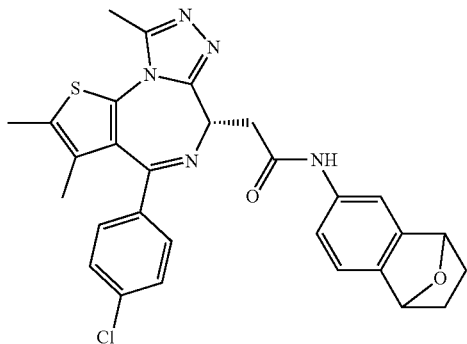 [SMILES: Cc1sc2c(c1C)C(c1ccc(Cl)cc1)=N[C@@H](CC(=O)Nc1ccc3c(c1)C1CCC3O1)c1nnc(C)n1-2]

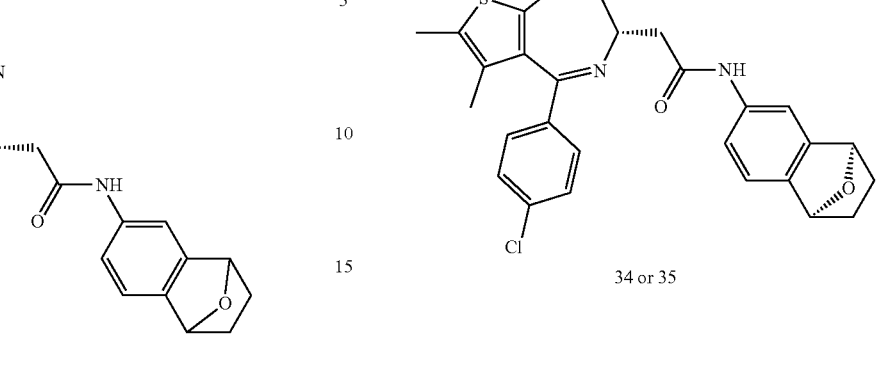

34 or 35

Compound 1-11 (35 mg, 87.31 μmol, 1.00 eq) and compound 34-4 (17 mg, 105.46 μmol, 1.21 eq) were successively added to a solution of HATU (35.00 mg, 92.05 μmol, 1.05 eq) in anhydrous N,N-dimethyl formamide (2 mL), and then triethylamine (28.00 mg, 276.71 μmol, 38.51 μL, 3.17 eq) was slowly added dropwisely. The mixture was stirred at 25° C. under the protection of nitrogen gas for 1 hour. Water (3 mL) was added to the reaction mixture to quench the reaction, The mixture was separated into two phases. The aqueous phase was extracted with methylene chloride (3×5 mL). The above organic phases were combined and washed with a saturated sodium bicarbonate solution (5 mL) and a saturated saline solution (5 mL). The organic phase was dried over anhydrous sodium sulfate and filtered. The filtrate was concentrated under reduced pressure. The obtained crude product was purified with a thin-layer chromatography plate to give compound 34-5. LCMS (ESI) m/z: 544.1 (M+1). $^1$H NMR (400 MHz, CDCl$_3$) δppm 8.73 (s, 1H), 7.52 (d, J=46.4 Hz, 1H), 7.34 (d, J=8.4 Hz, 2H), 7.26 (d, J=7.6 Hz, 2H), 7.05-7.22 (m, 2H), 5.28 (s, 2H), 4.52-4.56 (m, 1H), 3.68-3.74 (m, 1H), 3.37-3.41 (m, 1H), 2.60 (s, 3H), 2.33 (s, 3H), 1.61 (s, 3H), 1.27 (d, J=6.8 Hz, 2H), 1.19 (d, J=6.8 Hz, 2H).

Synthesis of Compounds 34 and 35

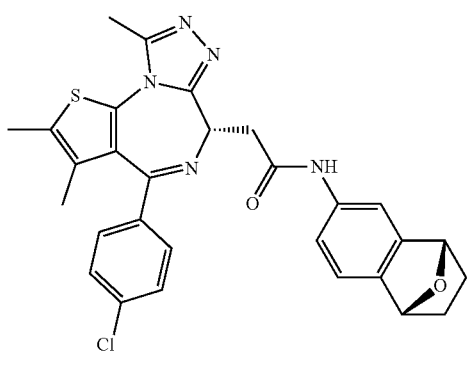

34 or 35

Compound 34-5 (20 mg, 36.73 μmol) was purified with a chiral separation (chromatography column: AD (250 mm×30 mm, 10 μm); mobile phase: [0.1% NH$_3$H$_2$O EtOH]; B %: 50%-50%) to give compound 34 (Rt=0.735 minutes). LCMS (ESI) m/z: 544.1 (M+1). $^1$H NMR (400 MHz, CDCl$_3$) δppm 8.79 (s, 1H), 7.58 (s, 1H), 7.34 (d, J=8.4 Hz, 2H), 7.26 (d, J=8.4 Hz, 2H), 7.11-7.15 (m, 1H), 7.05-7.07 (m, 1H), 5.29 (t, J=3.8 Hz, 2H), 4.53-4.57 (m, 1H), 3.67-3.73 (m, 1H), 3.38-3.42 (m, 1H), 2.60 (s, 3H), 2.33 (s, 3H), 1.91-1.96 (m, 2H), 1.61 (s, 3H), 1.25-1.29 (m, 2H).

Compound 35 (Rt=1.300 minutes). LCMS (ESI) m/z: 544.1 (M+1). $^1$H NMR (400 MHz, CDCl$_3$) δppm 8.76 (s, 1H), 7.46 (s, 1H), 7.34 (d, J=8.8 Hz, 2H), 7.26 (d, J=8.8 Hz, 2H), 7.21-7.22 (m, 1H), 7.05-7.07 (m, 1H), 5.28 (s, 2H), 4.53-4.57 (m, 1H), 3.68-3.74 (m, 1H), 3.37-3.42 (m, 1H), 2.60 (s, 3H), 2.33 (s, 3H), 1.94-1.96 (m, 2H), 1.61 (s, 3H), 1.25-1.29 (m, 2H).

Scheme 36

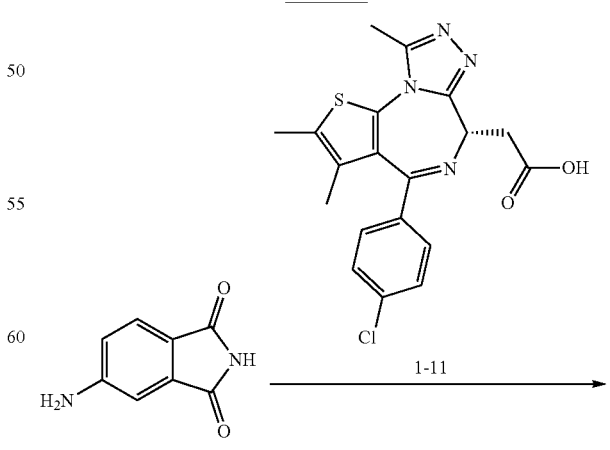

36-1   1-11 →

119
-continued
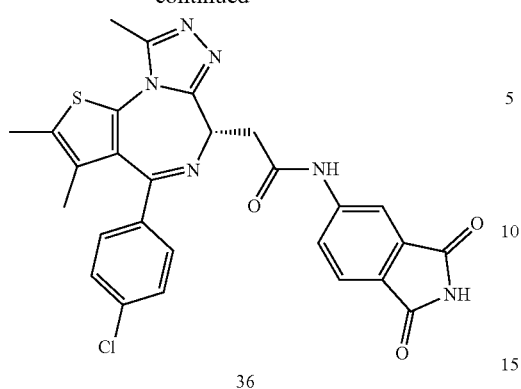
36
Example 36
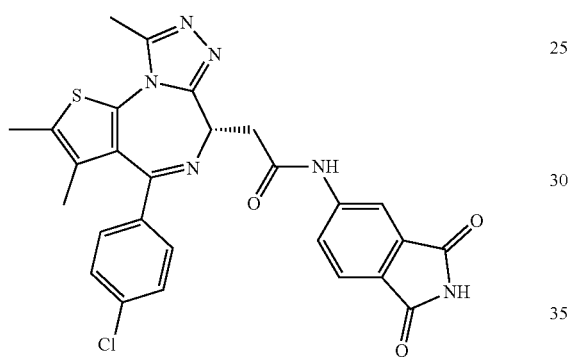
Example 36 was synthesized with reference to Example 1.
LCMS (ESI) m/z: 545.1 (M+1). $^1$H NMR (400 MHz, CDCl$_3$) δppm 10.10 (s, 1H), 8.08 (s, 1H), 7.73 (d, J=8.0 Hz, 1H), 7.60 (d, J=8.0 Hz, 2H), 7.34 (d, J=8.8 Hz, 2H), 7.25 (d, J=8.8 Hz, 2H), 4.61-4.65 (m, 2H), 3.80-3.86 (m, 1H), 3.48-3.53 (m, 1H), 2.65 (s, 3H), 2.36 (s, 3H), 1.63 (s, 3H).
Scheme 37
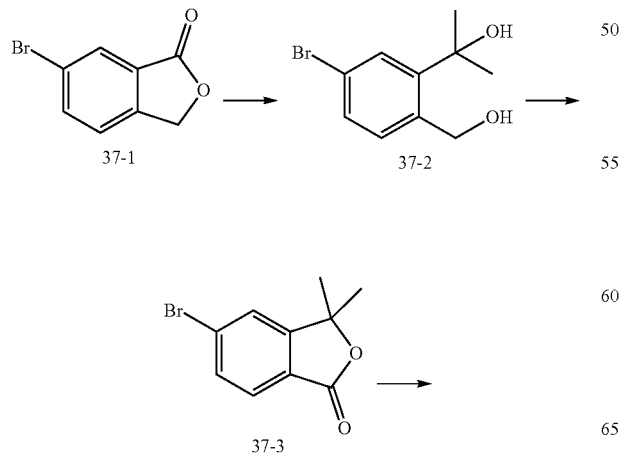
120
-continued
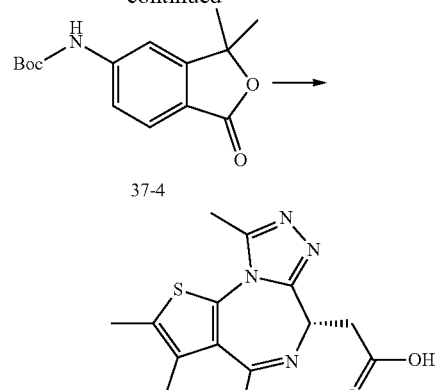
Example 37
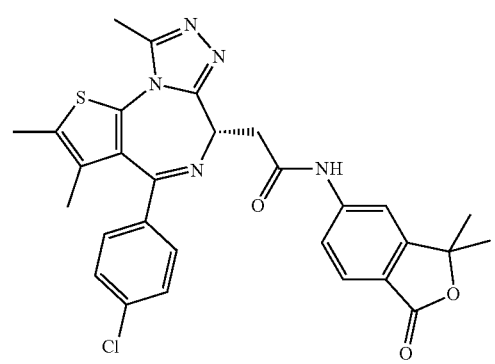

Synthesis of Compound 37-2

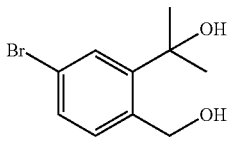

At 0° C. and under the protection of nitrogen gas, magnesium methyl bromide (3 M, 9.39 mL, 3 eq) was slowly added dropwisely to a solution of compound 37-1 (2 g, 9.39 mmol, 1 eq) in anhydrous tetrahydrofuran (20 mL). After the completion of the dropwise addition, the mixture was warmed up to 30° C. and stirred under the protection of nitrogen gas for 3 hours. The reaction mixture was cooled to 0° C., and a saturated ammonium chloride solution (10 mL) was slowly added dropwisely to quench the reaction. The mixture was extracted with methylene chloride (3×10 mL). The above organic phases were combined, dried over anhydrous sodium sulfate and filtered. The filtrate was concentrated under reduced pressure to give compound 37-2, which was directly used in the next step without the need for any further purification. $^1$H NMR (400 MHz, CDCl$_3$) δppm 7.44 (d, J=2.0 Hz, 1H), 7.39 (dd, J=8.4, 2.0 Hz, 1H), 7.22 (d, J=8.4, 1H), 4.81 (s, 2H), 1.70 (s, 6H).

Synthesis of Compound 37-3

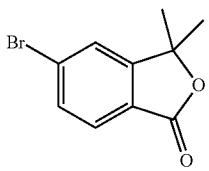

Compound 37-2 (2.1 g, 8.57 mmol, 1 eq) was added to a suspension of active manganese peroxide (7.35 g, 84.54 mmol, 9.87 eq) in anhydrous tetrahydrofuran (15 mL). The mixture was stirred at 70° C. for 3 hours. The reaction mixture was cooled to room temperature and filtered. The filtrate concentrated under reduced pressure to give compound 37-3, which was directly used in the next step without the need for any further purification. $^1$H NMR (400 MHz, CDCl$_3$) 7.65 (d, J=8.0 Hz, 1H), 7.57 (dd, J=8.0, 1.2 Hz, 1H), 7.49 (d, J=1.2 Hz, 1H), 1.59 (s, 6H).

Synthesis of Compound 37-4

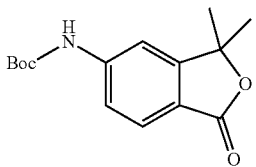

Tris(dibenzylideneacetone) dipalladium (380.00 mg, 414.98 μmol, 0.1 eq), 4,5-bis(diphenylphosphine)-9,9-dimethylxanthene (240.0 mg, 414.78 μmol, 0.1 eq) and cesium carbonate (2.70 g, 8.29 mmol, 2 eq) were successively added to a solution of compound 37-3 (1 g, 4.15 mmol, 1 eq) and tert-butyl carbamate (700.00 mg, 5.98 mmol, 1.44 eq) in anhydrous 1,4-dioxane (10 mL). The mixture was stirred at 100° C. under the protection of nitrogen gas for 2 hours. The reaction mixture was cooled to room temperature. Water (10 mL) was added to the reaction mixture. The mixture was extracted with methylene chloride (3×10 mL). The above organic phases were combined, dried over anhydrous sodium sulfate and filtered. The filtrate was concentrated under reduced pressure. The obtained crude product was purified with a silica gel column (elution condition: petroleum ether:ethyl acetate=1:1) to give compound 37-4. $^1$H NMR (400 MHz, CDCl$_3$) δppm 7.75 (s, 1H), 7.67 (d, J=8.0 Hz, 1H), 7.04 (dd, J=8.4, 1.6 Hz, 1H), 6.79 (br s, 1H), 1.58 (s, 6H), 1.47 (s, 9H).

Synthesis of Compound 37-5

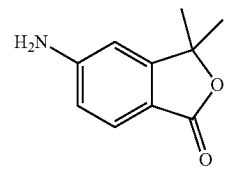

Trifluoroacetic acid (7.70 g, 67.53 mmol, 5 mL, 18.73 eq) was slowly added dropwisely to a solution of compound 37-4 (1 g, 3.61 mmol, 1 eq) in anhydrous methylene chloride (10 mL). The mixture was stirred at 30° C. for 1 hour. Water (5 mL) was added to the reaction mixture to quench the reaction. The mixture was adjusted with a saturated sodium bicarbonate solution to pH=7 and then extracted with methylene chloride (3×10 mL). The above organic phases were combined, dried over anhydrous sodium sulfate and filtered. The filtrate was concentrated under reduced pressure to give compound 37-5, which was directly used in the next step without the need for any further purification. LCMS (ESI) m/z: 177.8 (M+1).

Synthesis of Compound 37

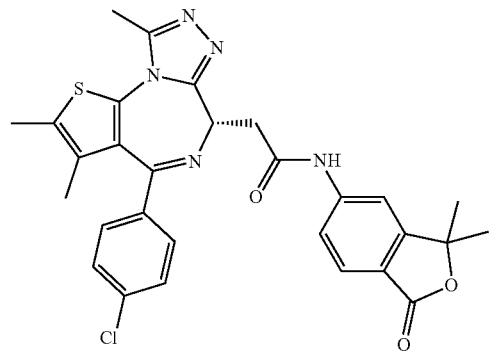

At 0° C., phosphorus oxychloride (140.00 mg, 913.05 μmol, 84.85 μL, 5.23 eq) was slowly added dropwisely to a solution of compound 1-11 (70 mg, 174.62 μmol, 1.00 eq) and compound 37-5 (40 mg, 225.73 μmol 1.29 eq) in pyridine (2 mL). The mixture was stirred at 0° C. under the protection of nitrogen gas for 1 hour. Water (3 mL) was added to the reaction mixture to quench the reaction. The above reaction mixture was adjusted with a hydrochloric acid solution (1 mol/L) to pH=7 and extracted with methylene chloride (3×5 mL). The above organic phases were combined and washed with a saturated sodium bicarbonate solution (5 mL) and a saturated saline solution (5 mL). The organic phase was dried over anhydrous sodium sulfate and filtered. The filtrate was concentrated under reduced pressure. The above crude product was purified with a thin-layer chromatography plate to give compound 37. LCMS (ESI) m/z: 560.0 (M+1). $^1$H NMR (400 MHz, CDCl$_3$) δppm 9.89 (br s, 1H), 7.92 (s, 1H), 7.62 (d, J=8.4 Hz, 1H), 7.36 (d, J=8.4 Hz, 2H), 7.25-7.30 (m, 3H), 4.57-4.61 (m, 1H), 3.78-3.81 (m, 1H), 3.45-3.50 (m, 1H), 2.62 (s, 3H), 2.35 (s, 3H), 1.64 (s, 3H), 1.54 (s, 3H), 1.53 (s, 3H).

BRD4 Biochemical Activity Test

Experiment Preparation:

1) BRD4-BD1 and BRD4-BD2 proteins of BPS Company, polypeptide of ANASPEC Company, and test reagent of PerkinElmer Company were used in the experiments;

2) The TR-FRET experimental principle was used in the experiment to screen compounds.

3) Relevant control compounds

Experiment Steps:

1) Preparation of the Compound Plate:

Preparation of the compound plate in the experiment was achieved by Echo:

Compound dilution was completed with Echo, and a three-fold serial dilution to 10 concentrations: 20000, 6666.67, 2222.22, 740.74, 246.91, 82.305, 27.435, 9.145, 3.048, and 1.016 nM, was carried out.

2) Preparation of Reaction Reagents:

Relevant reaction reagents should be prepared on the day of the experiment:

a) Formulation of 1× assay buffer;

b) Formulation of 3× component solution for the experiment:

1. The reagent was taken out and placed on ice to naturally melt for later use;

2. "Solution A" (protein solution), "solution B" (polypeptide solution), and "solution C" (test reagent solution) used in the experiment were formulated with the 1× assay buffer, and during the formation of the 3× solution from the components used in the experiment reaction system, the amounts of solutions A, B and C must be enough for the required amounts in the experiment.

3) Experimental Operation Steps:

The experiment plate was a plate that contained a gradient concentration of the compound and a corresponding DMSO solution and was prepared with ECHO before the experiment:

a) The experiment plate was taken out, and 5 μL/well of "solution A" (protein solution) was added to columns 2-23 of the experiment plate, then 5 μL/well of 1× assay buffer was added to columns 1 and 24 of the experiment plate, and columns 1 and 24 were used as Min control in the experiment system;

b) Centrifugation at 1000 rpm was carried out for 30 seconds;

c) The plate was incubated at 23° C. for 20 minutes;

d) After 20 minutes of incubation, 5 μL/well of "solution B" (polypeptide solution) was added to columns 1-24 of the experiment plate;

e) Centrifugation at 1000 rpm was carried out for 30 seconds;

f) The plate was incubated at 23° C. for 20 minutes;

g) After 20 minutes of incubation, 5 μL/well of "solution C" (test reagent solution) was added to columns 1-24 of the experiment plate;

h) Centrifugation at 1000 rpm was carried out for 30 seconds;

i) The plate was incubated at 23° C. for 40 minutes;

j) The experiment plate was placed on EnVision to read the plate.

4) Data Analysis:

a) The corresponding Max control and Min control of each experiment plate were used to convert to the Z' value of the experiment plate, and the Z' value of each plate was ensured to be >0.5;

b) The IC$_{50}$ value was calculated from the signal of the control compound by XLFIT5, and ensured to be maintained within 3 times of the average value of historical data. The results were shown in Table 1.

TABLE 1

IC$_{50}$ test results of the BRD4 test

| Compound | BRD4 Binding (BD1, BD2), IC$_{50}$(nM) |
| --- | --- |
| 1 | 65, 11 |
| 2 | 49, 10 |
| 3 | 87, 15 |
| 4 | 129, 14 |
| 5 | 83, 9 |
| 6 | 327, 90 |
| 7 | 100, 21 |
| 8 | 51, 11 |
| 9 | 49, 11 |
| 10 | 81, 16 |
| 11 | 49, 14 |
| 12 | 40, 12 |
| 13 | 50, 8 |
| 14 | 69, 8 |
| 15 | 91, 11 |
| 16 | 60, 12 |
| 17 | 24, 7 |
| 18 | 23, 8 |
| 19 | 49, 8 |
| 20 | 169, 11 |
| 21 | 522, 34 |
| 22 | 199, 10 |
| 23 | 158, 22 |
| 24 | 206, 17 |
| 25 | 79, 20 |
| 26 | 112, 30 |
| 27 | 55, 9 |
| 28 | 60, 15 |
| 29 | 74, 16 |
| 30 | 51, 9 |
| 31 | 37, 5 |
| 32 | 66, 10 |
| 33 | 248, 19 |
| 34 | 117, 11 |
| 35 | 155, 12 |
| 36 | 126, 10 |
| 37 | 148, 11 |

Conclusion: The compounds of the present invention had significant BET Bromodomain inhibitory activities.

In Vivo Pharmacodynamics Study of Compound 32 on Human Breast Cancer MDA-MB-231_luc Cell Subcutaneous Xenograft Tumor Model 1. Experiment Design

TABLE 2

Formulation method of the substance to be tested

| Compound | Packaging or starting concentration | Formulation method | Concentration (mg/mL) | Storage condition |
|---|---|---|---|---|
| Medium | — | 5% DMSO + 40% PEG400 + 10% Kolliphor ® HS 15 + 45% $H_2O$ | — | 4° C. |
| Compound 32 50 mg/kg, BID | 511 mg | 126.52 mg of Compound 32 was added to a brown bottle, and then 1.26 mL of DMSO was added thereto. The mixture was stirred by vortex to a homogeneous solution. 10.080 mL of PEG400 and 2.52 mL of solutol were added and stirred by vortex to a homogeneous solution, and then 11.340 mL of $H_2O$ was added and stirred by vortex to obtain a solution containing Compound 32 at a concentration of 5 mg/mL. | 5 | 4° C. |

TABLE 3

Animal grouping and dosage regimen for in vivo pharmacodynamic experiments

| Group | Number of animals | Compound treatment | Dosage (mg/kg) | Administration volume parameter (µL/g) | Administration route | Administration frequency |
|---|---|---|---|---|---|---|
| 1 | 6 | Vehicle | — | 10 | PO | BID × 21 days |
| 2 | 6 | Compound 32 | 50 | 10 | PO | BID × 21 days |

2. Experiment Material
2.1 Experiment Animals
Species: mouse
Strain: BALB/c nude mouse
Week-age and weight: 6-8 weeks of age, 18-22 grams of body weight
Sex: Female
Supplier: Shanghai Sippr-BK laboratory animal Co. Ltd.
3. Experiment Methods and Steps
3.1 Cell Culture
Human breast cancer MDA-MB-231_luc cells were cultured in monolayer in vitro and the culture conditions were RPMI-1640 culture medium (supplier: Gibco; article number: 22400-089; manufacturing batch number: 4868546) with 10% fetal bovine serum, 100 U/ml penicillin and 100 µg/ml streptomycin. The culture was performed at 37° C. in 5% $CO_2$. Conventional digestion treatment with pancreatin-EDTA for passage was carried out twice a week. When the cells were in the exponential growth phase, the cells were harvested, counted, and inoculated.
3.2 Tumor Cell Inoculation
0.2 mL of 10×10$^6$ MDA-MB-231_luc cells were subcutaneously inoculated into the right-back of each nude mouse (PBS:Matrigel=1:1). The grouping and administration was started when the average tumor volume reached 100-150 mm$^3$.
3.3 Tumor Measurement and Experiment Indices
The experiment index was to investigate whether tumor growth was inhibited, delayed or cured. Tumor diameter was measured twice a week with vernier calipers. The equation for calculating the tumor volume was V=0.5×a×b$^2$, wherein a and b represented the major and minor diameters of the tumor, respectively.
The tumor inhibition effect of the compound was evaluated by TGI (%) or relative tumor proliferation rate T/C (%). TGI (%) reflected the tumor growth inhibition rate. Calculation of TGI (%) was as follows: TGI (%)=[(1−(average tumor volume at the end of administration in a treatment group−average tumor volume at the beginning of administration in this treatment group))/(average tumor volume at the end of treatment in the solvent control group−average tumor volume at the beginning of treatment in the solvent control group)]×100%.
Relative tumor proliferation rate T/C (%) was calculated according to the below equation: T/C %=$T_{RTV}/C_{RTV}$×100% ($T_{RTV}$: RTV of the treatment group; $C_{RTV}$: RTV of the negative control group). The relative tumor volume (RTV) was calculated according to the results of the tumor measurement. The calculation equation was RTV=$V_t/V_0$, where $V_0$ was the average tumor volume measured at the grouping and administration (i.e. $d_0$), and $V_t$ was the average tumor volume at the time of a certain measurement. $T_{RTV}$ and $C_{RTV}$ were obtained from the data on the same day.
At the end of the experiment, the tumor weight would be measured and the $T_{weight}/C_{weight}$ percentage would be calculated. $T_{weight}$ and $C_{weight}$ represented the tumor weights of the administration group and the medium control group, respectively.
3.4 Statistical Analysis
Statistical analysis included mean value and standard error (SEM) of the tumor volume of each group at each time point. The treatment group showed the best treatment effect on the 21st day after the administration at the end of the experiment, so the statistical analysis was performed based on this data to evaluate the differences between the groups. The comparison between two groups was analyzed by T-test, and the comparison between three or more groups was analyzed by one-way ANOVA. If the F value was significantly different, the Games-Howell test was applied. If the F value was not significantly different, the Dunnet (2-sided) test was used for analysis. All data analysis was performed with SPSS 17.0. $p<0.05$ was considered significantly different.

4. Experiment Conclusion

On the 21st day after administration, for the test compound 32, the tumor growth inhibition rate TGI=54.85%, T/C=52.99%, p<0.05; there was no significant change in body weight of the animals, and they were well tolerated.

In Vivo Pharmacodynamics Study of Compound 32 on Human Prostatic Cancer PC-3 Cell Subcutaneous Xenograft Tumor Model 1. Experimental Design The formulation method of the test substance was the same as in Table 2, and the animal grouping and the dosage regimen were the same as in Table 3.

2. Experiment Material 2.1 Experiment Animals

Species: mouse

Strain: BALB/c nude mouse

Week-age and weight: 6-8 weeks of age, 18-22 grams of body weight

Sex: male

Supplier: Shanghai Sippr-BK laboratory animal Co. Ltd.

3. Experiment Methods and Steps 3.1 Cell Culture

Human prostatic cancer PC-3 cells were cultured in monolayer in vitro, and the culture conditions were F-12K culture medium (supplier: Gibco; article number: 21127-022; manufacturing batch number: 1868870) with 10% fetal bovine serum, 100 U/mL penicillin and 100 µg/mL streptomycin. The culture was performed at 37° C. in 5% $CO_2$. Conventional digestion treatment with pancreatin-EDTA for passage was carried out twice a week. When the cells were in the exponential growth phase, the cells were harvested, counted, and inoculated.

3.2 Tumor Cell Inoculation 0.1 mL of $10 \times 10^6$ PC-3 cells were subcutaneously inoculated into the right-back of each nude mouse. The grouping and administration was started when the average tumor volume reached 100-150 $mm^3$.

3.3 Tumor Measurement, Experiment Indices, and Statistical Analysis were the Same as MDA-MB-231 Model 4. Experiment Conclusion On the 21st day after administration, compared with the solvent control group, the test compound 32 had a significant tumor inhibition effect (T/C=44.63%, TGI=58.4%, p=0.033); the animals were well tolerated.

In Vivo Pharmacokinetics Test of Compound 32 in Mice

Female Balb/c mice were used as test animals. The compound 32 was administrated intravenously and intragastrically to mice, then the drug concentrations in the plasma at different time points were determined by the LC/MS/MS method. The in vivo pharmacokinetic behavior of compound 32 in mice was studied, and its pharmacokinetic characteristics were evaluated.

1. Experiment Protocol 1.1 Experiment drug: Compound 32

1.2 Experiment animals: Sixteen healthy adult female Balb/c mice were divided into four groups according to the principle of similar body weight, with four mice in each group. The animals were purchased from Shanghai Lingchang BioTech Co., Ltd. of Shanghai SLAC Laboratory Animal Co., Ltd., and the animal production license number was SCXK (Shanghai) 2013-0018.

1.3 Drug Formulation

An appropriate amount of the sample was taken, 5% final volume of DMSO was added, and then 95% final volume of 20% HP-β-CD was added. The mixture was ultrasonically stirred to obtain a 0.5 mg/mL clear solution. After filtration, it was used for the intravenous administration.

An appropriate amount of the sample was taken, and dissolved in a 0.5% sodium carboxymethyl cellulose solution. The mixture was ultrasonically stirred to obtain a 0.5 mg/mL homogeneous suspension, which was used for the intragastric administration.

1.4 Administration

Eight female Balb/c mice were divided into two groups. After fasting overnight, the first group was administered intravenously with the administration volume of 2.5 mL/kg and the dosage of 1 mg/kg. The second group was administered intragastrically with the administration volume of 5 mL/kg and the dosage of 2 mg/kg.

2. Operation

After the female Balb/c mice were intravenously administrated, 30 µL of blood was taken from different mice at each time point of 0.0833, 0.25, 0.5, 1, 2, 4, 8 and 24 hours, and placed in test tubes containing 2 µL of EDTA-$K_2$; and after the female Balb/c mice were intragastrically administrated, 30 µL of blood was taken at an alternative location at each time point of 0.25, 0.5, 1, 2, 4, 8 and 24 hours, and placed in test tubes containing 2 µL of EDTA-$K_2$. The tube was centrifuged at 3000 g for 15 minutes to separate the plasma, and the separated plasma was stored at −60° C. Animals could take food 2 hours after the administration.

The LC/MS/MS method was used to measure the content of the compound to be tested in the plasma after the intravenous and intragastric administration to the mice. The linear range of the method was 2.00-6000 nmol/L; the plasma samples were analyzed after the protein precipitation by acetonitrile treatment. The results of the pharmacokinetic parameters were shown in Table 4.

TABLE 4

Results of pharmacokinetic parameters

| | | Compound 32 Administration mode | |
|---|---|---|---|
| | | Intravenous | Intragastric |
| | | Administration dosage | |
| | | 1 mg/kg | 3 mg/kg |
| Drug concentration in blood | $C_{max}$ (nM) | — | 930 |
| Time to peak | $T_{max}$ (h) | — | 1.00 |
| Half life | $T_{1/2}$ (h) | 1.09 | 1.47 |
| Apparent distribution volume | Vdss (L/kg) | 1.19 | — |
| Clearance rate | Cl (mL/min/kg) | 12.5 | — |
| Curve area (0-t) | $AUC_{0-last}$ (nM · h) | 2490 | 2740 |
| Curve area (0-inf) | $AUC_{0-inf}$ (nM · h) | 2502 | 2818 |
| Bioavailability | Bioavailability (%) | — | 37.50% |

"—": Not available.

Experiment conclusion: Compound 32 had low pharmacokinetic clearance and good absorption.

In Vivo Anti-Tumor Effect of Compound 32 in MC38 Mouse Colon Cancer Cell Animal Transplantation Tumor Model 1. Experimental Design

| Group | 1 | 2 | 3 | 4 |
|---|---|---|---|---|
| Number of animals | 10 | 10 | 10 | 10 |
| Substance to be tested | Medium control | Compound 32 | Compound 32 | Compound 32 |
| Dosage mg/kg | — | 15 | 25 | 50 |
| Administration volume mL/kg | 10 | 10 | 10 | 10 |
| Administration route | p.o. | p.o. | p.o. | p.o. |
| Administration frequency and cycle | BID × 20 days | BID × 20 days | BID × 20 days | BID × 20 days |

2. Experiment Material 2.1 Experiment Animals

Species: mouse

Strain: C57BL6 mouse

Week-age and weight: 6-7 weeks of age, 16-20 grams of body weight

Sex: Female

Supplier: Shanghai SLAC Laboratory Animal Co., Ltd.

3. Experiment Methods and Steps 3.1 Cell Culture

Mouse colon cancer MC38 cells (OBiO Technology (Shanghai) Corp., Ltd.) were cultured in monolayer in vitro, and the culture conditions were DMEM culture medium (Gibco; article number: 12100) with 10% fetal bovine serum. The culture was performed at 37° C. in 5% $CO_2$ in an incubator. Conventional digestion treatment with 0.25% pancreatin-EDTA for passage was carried out. When the cells were in the exponential growth phase and the saturation was 80%-90%, the cells were harvested, counted, and inoculated.

3.2 Tumor Cell Inoculation 0.1 mL of $2 \times 10^5$ MC38 cells were subcutaneously inoculated into the right-back of each mouse. The random grouping and administration was carried out according to the tumor volume when the average tumor volume reached about 70 $mm^3$.

3.3 Tumor Measurement

Tumor diameter was measured twice a week with vernier calipers. The equation for calculating tumor volume was $V = 0.5 \times a \times b^2$, wherein a and b represented the major and minor diameters of the tumor, respectively.

The tumor inhibition effect of the compound was evaluated by TGI (%) or relative tumor proliferation rate T/C (%). Relative tumor proliferation rate T/C (%) = $T_{RTV}/C_{RTV} \times 100\%$ ($T_{RTV}$: RTV of the treatment group; $C_{RTV}$: RTV of the negative control group). The relative tumor volume (RTV) was calculated according to the results of the tumor measurement. The calculation equation was $RTV = V_t/V_0$, where $V_0$ was the average tumor volume measured at the grouping and administration (i.e. $D_0$), and $V_t$ was the average tumor volume at the time of a certain measurement. $T_{RTV}$ and $C_{RTV}$ were obtained from the data on the same day.

TGI (%) reflected the tumor growth inhibition rate. TGI (%) = [(1−(average tumor volume at the end of administration in a treatment group−average tumor volume at the beginning of administration in this treatment group))/(average tumor volume at the end of treatment in the solvent control group−average tumor volume at the beginning of treatment in the solvent control group)] × 100%.

At the end of the experiment, the tumor weight would be measured and the $T_{weight}/C_{weight}$ percentage would be calculated. $T_{weight}$ and $C_{weight}$ represented the tumor weights of the administration group and the medium control group, respectively.

3.4 Statistical Analysis

Statistical analysis was performed using SPSS software based on the tumor volume and the tumor weight at the end of the experiment. The comparison between two groups was analyzed by t-test, and the comparison between three or more groups was analyzed by one-way ANOVA. If the variance was homogeneous (the F value was not significantly different), the LSD method was used for analysis. If the variance was not homogeneous (the F value was significantly different), the Games-Howell method was used for the test. $p < 0.05$ was considered significantly different.

4. Experiment Conclusion

On the 20th day after administration, for the test compound 32, for the 15 mg/kg administration group: the relative tumor proliferation rate T/C=33.68%, the tumor growth inhibition rate TGI=68.81%, $p<0.0001$; for the 25 mg/kg administration group: the relative tumor proliferation rate T/C=27.59%, TGI=75.21%, $p<0.0001$; and for the 50 mg/kg administration group: T/C=10.04%, TGI=93.46%, $p<0.0001$. Significant tumor inhibition effects were shown in each administration group of animals with good tolerance.

The invention claimed is:

1. A compound represented by formula (I) or (II),

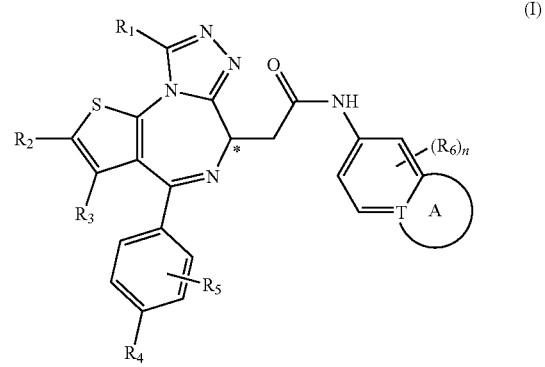

(I)

-continued (II)

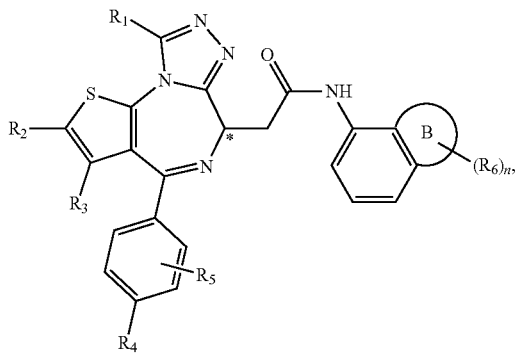

or a geometric isomer, a stereoisomer, a tautomer, or a pharmaceutically acceptable salt thereof, wherein, T is C or N;

$R_1$ is $C_{1-3}$ alkyl or $C_{1-3}$ alkoxyl, wherein the $C_{1-3}$ alkyl or $C_{1-3}$ alkoxyl is optionally substituted by 1, 2 or 3 independently selected R substituents;

each of $R_2$, $R_3$, and $R_4$ is independently H, F, Cl, Br, I, OH, $NH_2$, CN, $C_{1-6}$ alkyl, or $C_{1-6}$ heteroalkyl, wherein the $C_{1-6}$ alkyl or $C_{1-6}$ heteroalkyl is optionally substituted by 1, 2 or 3 independently selected R substituents, wherein the heteroatoms are 1, 2, 3, or 4 of N, —O—, —S—, —NH—, —C(=O)NH—, —C(=O)—, —C(=O)O—, —S(=O)$_2$—, —S(=O)—, or —C(=O)S—;

$R_5$ is H, or $C_{1-3}$ alkyl that is optionally substituted by 1, 2 or 3 independently selected R substituents;

each $R_6$ is independently H, F, Cl, Br, I, OH, $NH_2$, CN, $C_{1-6}$ alkyl, or $C_{1-6}$ heteroalkyl, wherein the $C_{1-6}$ alkyl or $C_{1-6}$ heteroalkyl is optionally substituted by 1, 2 or 3 independently selected R substituents, wherein the heteroatoms are 1, 2, 3, or 4 of N, —O—, —S—, —NH—, —C(=O)NH—, —C(=O)—, —C(=O)O—, —S(=O)2-, —S(=O)—, or —C(=O)S—; or two $R_6$ groups attached to the same carbon atom form C(=O) together with the carbon atom attached thereto;

either ring A is a $C_{3-7}$ cycloalkyl, a 5 or 7-12 membered heterocycloalkyl, or a 5-6 membered heteroaryl, wherein the heteroatoms are 1, 2, 3, or 4 of N, —O—, —S—, —NH—, —C(=O)NH—, —C(=O)—, —C(=O)O—, —S(=O)2-, —S(=O)—, or —C(=O)S—, or ring A is a 6 membered heterocycloalkyl, wherein the heteroatoms are 1, 2, 3, or 4 of N, —O—, —S—, —C(=O)—, —C(=O)O—, —S(=O)2-, —S(=O)—, or —C(=O)S—, provided that the structural unit

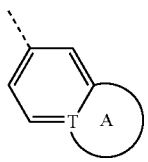

is not selected from a group consisting of

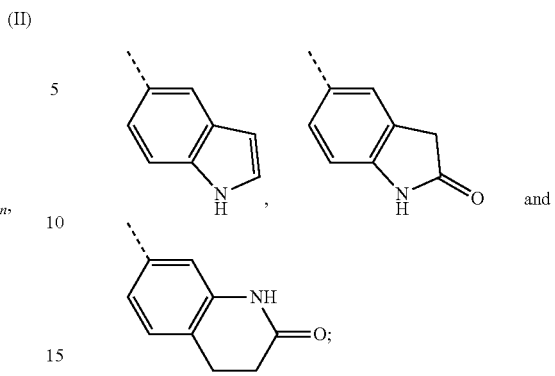

ring B is 4-7 membered heterocycloalkyl, wherein the heteroatoms are 1, 2, 3, or 4 of N, —O—, —S—, —NH—, —C(=O)NH—, —C(=O)—, —C(=O)O—, —S(=O)2-, —S(=O)—, or —C(=O)S—;

n is 0, 1, 2, 3, 4, 5, or 6;

each R is independently F, Cl, Br, I, OH, $NH_2$, CN, $C_{1-6}$ alkyl, or $C_{1-6}$ heteroalkyl, wherein the $C_{1-6}$ alkyl or $C_{1-6}$ heteroalkyl is optionally substituted by 1, 2 or 3 independently selected R' substituents, wherein the heteroatoms are 1, 2, 3, or 4 of N, —O—, —S—, —NH—, —C(=O)NH—, —C(=O)—, —C(=O)O—, —S(=O)2-, —S(=O)—, or —C(=O)S—;

each R' is independently F, Cl, Br, I, OH, $NH_2$, CN, or Me; and the carbon atom marked with "*" is a chiral carbon atom, which is present in the form of a single (R) or (S) enantiomer, or in the form of being enriched in one of two enantiomers.

2. The compound, geometric isomer, stereoisomer, tautomer, or pharmaceutically acceptable salt of claim 1, wherein each R is independently F, Cl, Br, I, OH, $NH_2$, CN, $C_{1-3}$ alkyl, or $C_{1-3}$ alkoxyl, wherein each $C_{1-3}$ alkyl and $C_{1-3}$ alkoxyl is optionally substituted by 1, 2 or 3 independently selected R' substituents.

3. The compound, geometric isomer, stereoisomer, tautomer, or pharmaceutically acceptable salt of claim 2, wherein each R is independently F, Cl, Br, I, OH, $NH_2$, CN, Me, $CF_3$, Et, or

4. The compound, geometric isomer, stereoisomer, tautomer, or pharmaceutically acceptable salt of claim 1, wherein $R_1$ is selected from a group consisting of Me, Et and

all of which are optionally substituted by 1, 2 or 3 independently selected R substituents.

5. The compound, geometric isomer, stereoisomer, tautomer, or pharmaceutically acceptable salt of claim 1, wherein $R_2$, $R_3$, and $R_4$ are independently H, F, Cl, Br, I, OH, $NH_2$, CN, $C_{1-3}$ alkyl, or $C_{1-3}$ alkoxy, wherein each $C_{1-3}$ alkyl and $C_{1-3}$ alkoxy is optionally substituted by 1, 2 or 3 independently selected R substituents.

6. The compound, geometric isomer, stereoisomer, tautomer, or pharmaceutically acceptable salt according to claim 5, wherein $R_2$, $R_3$, and $R_4$ are independently H, F, Cl, Br, I, OH, $NH_2$, CN, Me, or

.

7. The compound, geometric isomer, stereoisomer, tautomer, or pharmaceutically acceptable salt of claim 1, wherein $R_5$ is H or Me.

8. The compound, geometric isomer, stereoisomer, tautomer, or pharmaceutically acceptable salt of claim 1, wherein each $R_6$ is independently H, F, Cl, Br, I, OH, $NH_2$, CN, $C_{1-3}$ alkyl, or $C_{1-3}$ heteroalkyl, wherein each $C_{1-3}$ alkyl and $C_{1-3}$ heteroalkyl is optionally substituted by 1, 2 or 3 independently selected R substituents.

9. The compound, geometric isomer, stereoisomer, tautomer, or pharmaceutically acceptable salt of claim 8, wherein each $R_6$ is independently H, F, Cl, Br, I, OH, $NH_2$, CN, Me, Et,

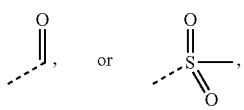

wherein the Me, Et,

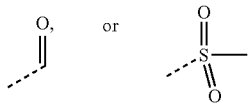

is optionally substituted by 1, 2 or 3 independently selected R substituents.

10. The compound, geometric isomer, stereoisomer, tautomer, or pharmaceutically acceptable salt of claim 9, wherein each $R_6$ is independently H, F, Cl, Br, I, OH, $NH_2$, CN, Me, Et,

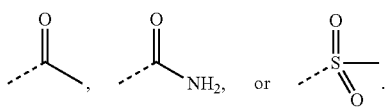.

11. The compound, geometric isomer, stereoisomer, tautomer, or pharmaceutically acceptable salt of claim 1, wherein ring A is $C_{4-6}$ cycloalkyl, pyrrolidin-2-onyl, pyrimidin-4(3H)-onyl, 5-azaspiro[2.4]heptan-4-onyl, 4-azaspiro[2.4]heptan-5-onyl, tetrahydrothiophene-1,1-dioxide group, tetrahydrothiophene-1-oxide group, tetrahydrofuranyl, pyrrolidinyl, dihydrothiophene-2(3H)-onyl, 2-oxaspiro[3.4]octyl, dihydrofuran-2(3H)-onyl, 1,4,7,10-tetraoxacyclododecyl, 1,2,5-oxadiazolyl, 7-oxabicyclo-[2.2.1]heptane, pyrrolidin-2,5-dione, or 5,5-dimethyl-dihydrofuran-2(3H)-onyl.

12. The compound, geometric isomer, stereoisomer, tautomer, or pharmaceutically acceptable salt of claim 1, wherein the structural unit

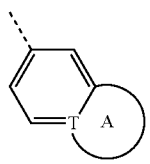

is

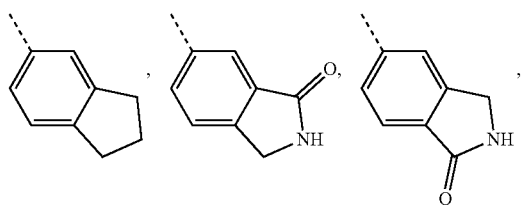

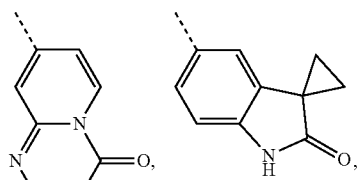

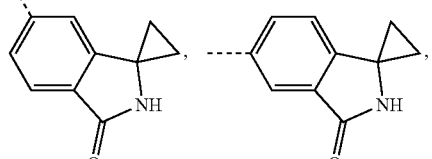

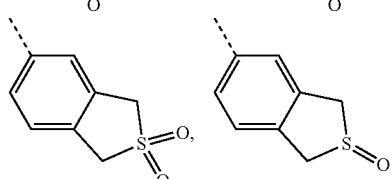

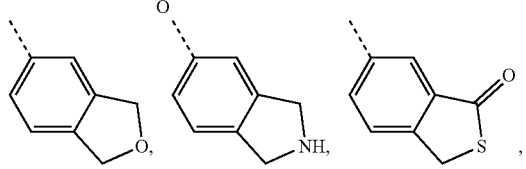

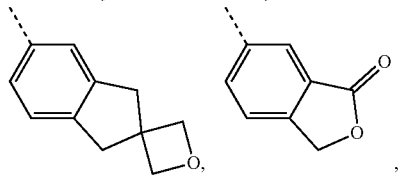

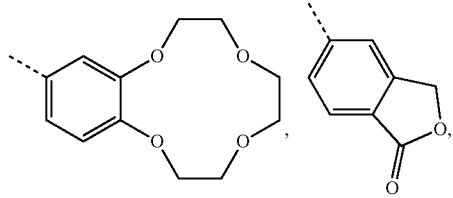

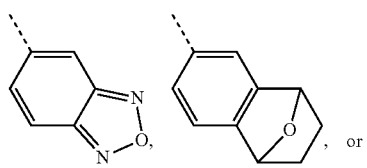

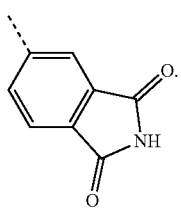
13. The compound, geometric isomer, stereoisomer, tautomer, or pharmaceutically acceptable salt of claim 12, wherein the structural unit
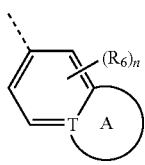
is
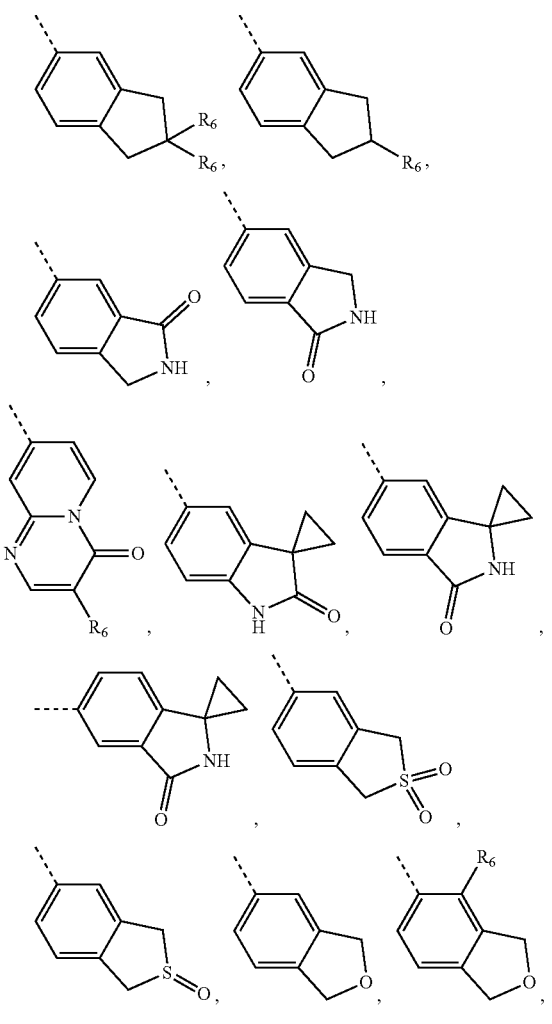
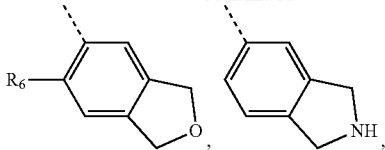
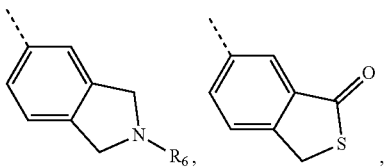
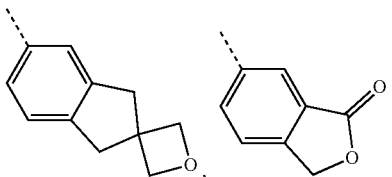
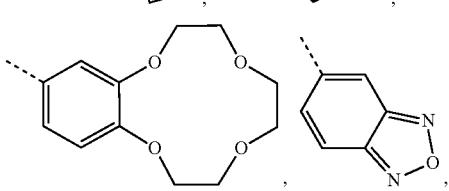
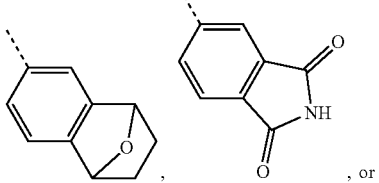
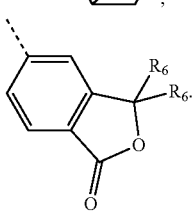
, or
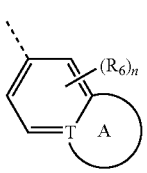
14. The compound, geometric isomer, stereoisomer, tautomer, or pharmaceutically acceptable salt of claim 13, wherein the structural unit
is
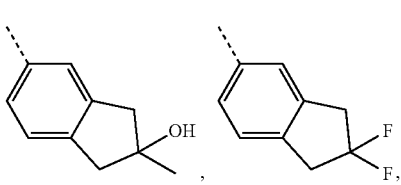

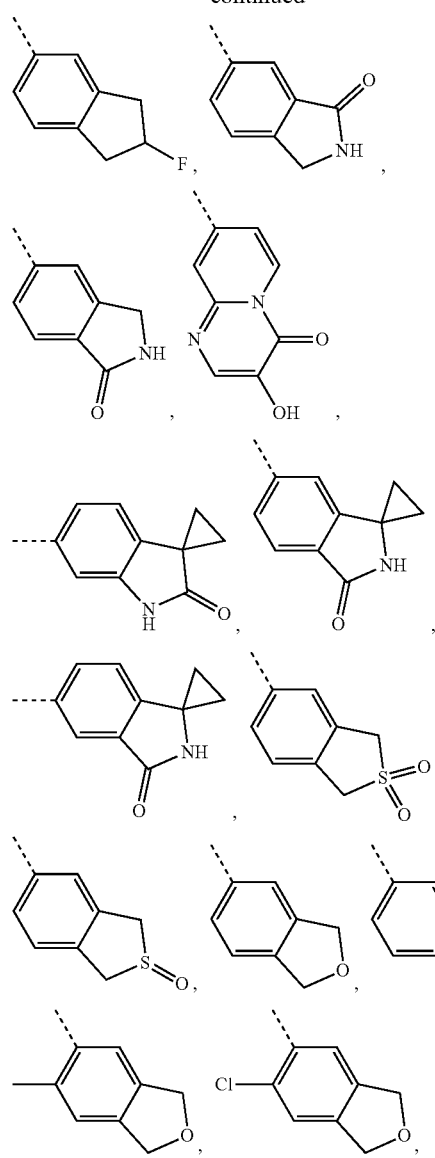
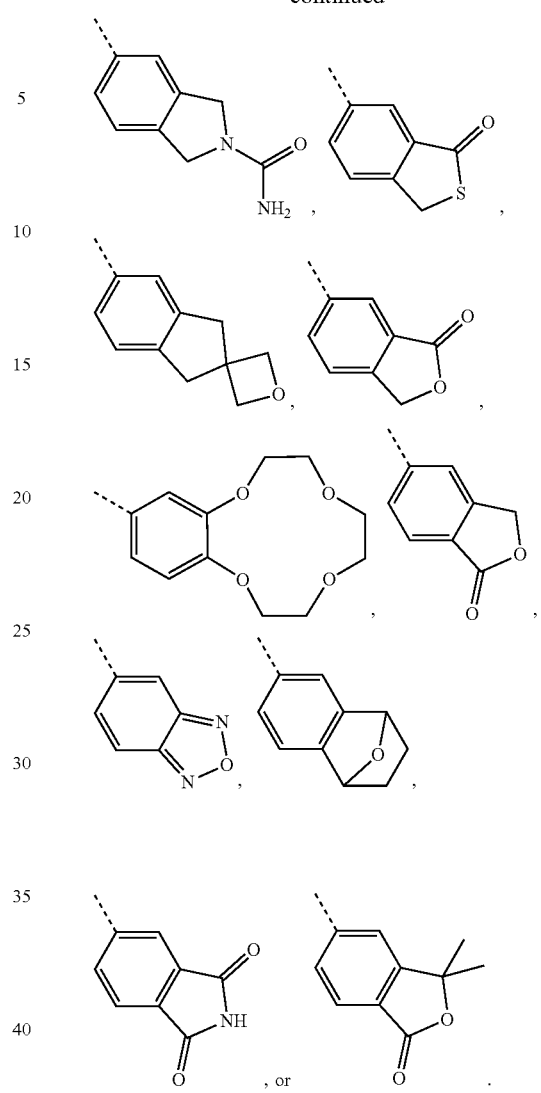
15. The compound, geometric isomer, stereoisomer, tautomer, or pharmaceutically acceptable salt of claim 1, wherein the structural unit
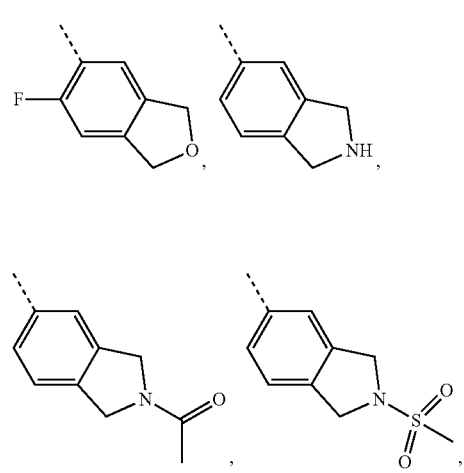
is
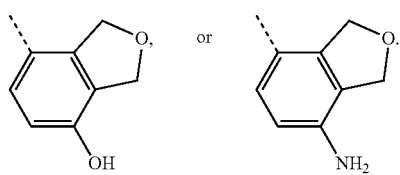

16. The compound, geometric isomer, stereoisomer, tautomer, or pharmaceutically acceptable salt of claim 1, which is
(I-1)
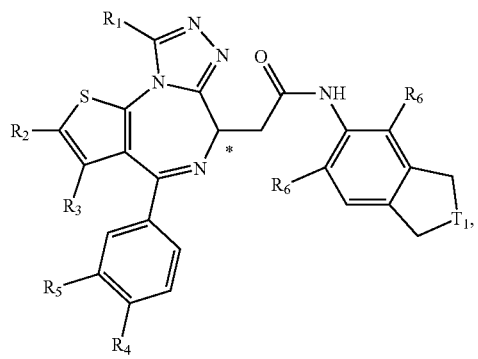
(I-2)
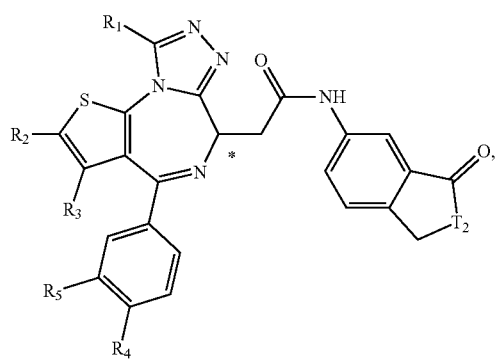
(I-3)
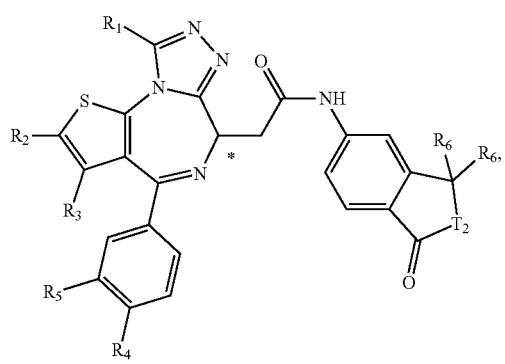
(I-4)
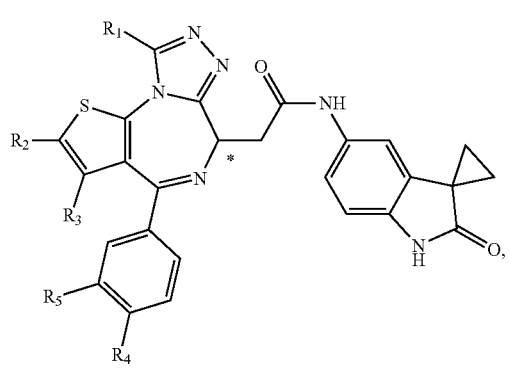
(I-5)
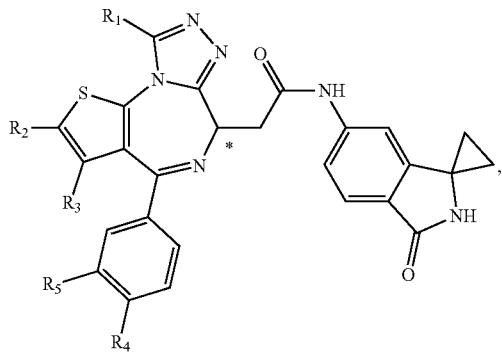
(I-6)
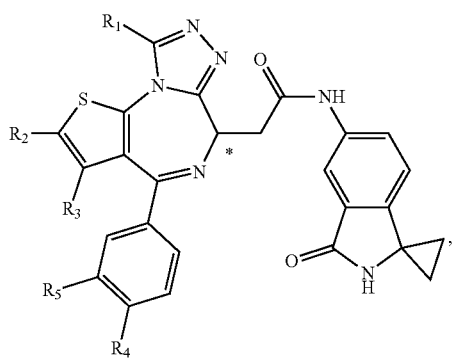
(I-7)
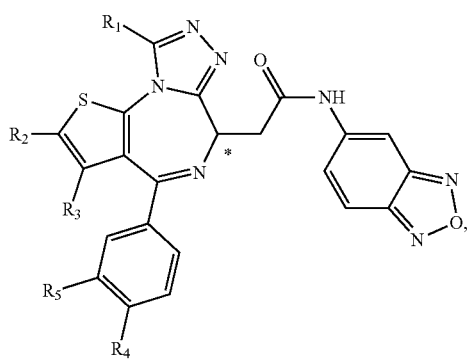
(I-8)
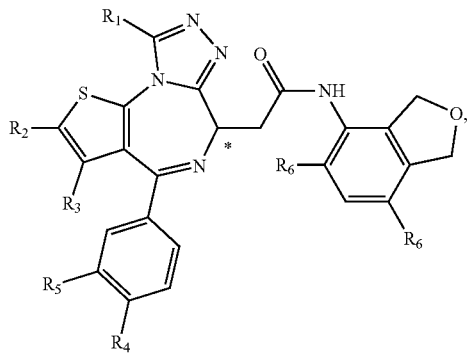

-continued (I-9)
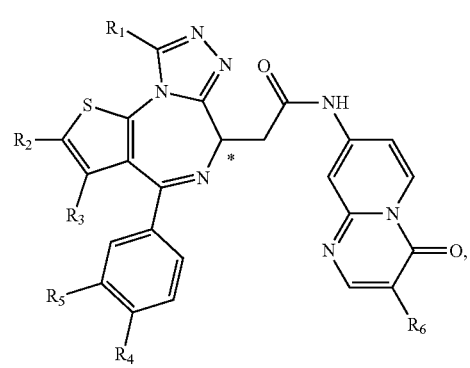

(I-10)
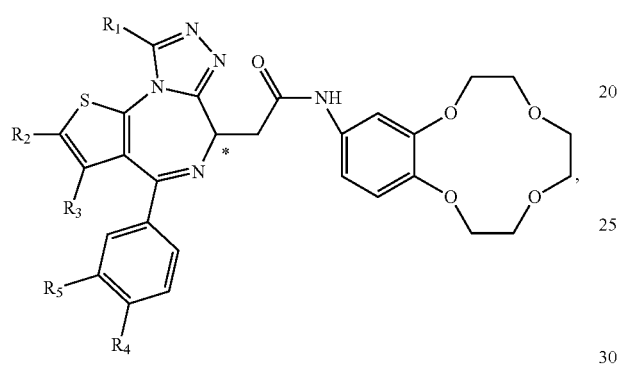

or (I-11)
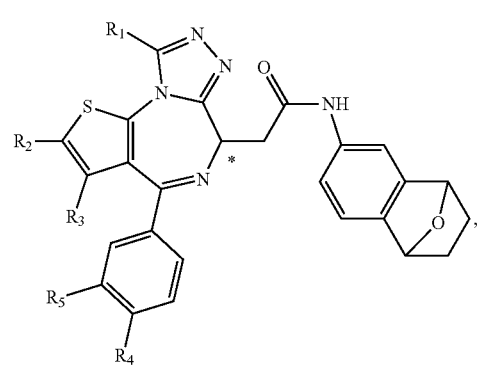

wherein,
T₁ is —S(=O)—, —S(=O)₂—, —N(R₆)—, —O—, —C(R₆)(R₆)—, or

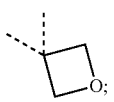

T₂ is independently —NH—, —O—, or —S—;
R₁-R₆ are as defined in claim 1; and
the carbon atom marked with "*" is a chiral carbon atom, which is present in the form of a single (R) or (S) enantiomer, or in the form of being enriched in one of two enantiomers.

17. The compound, geometric isomer, stereoisomer, tautomer, or pharmaceutically acceptable salt of claim 1, wherein the compound is

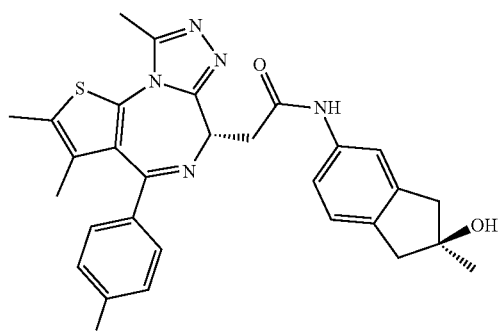

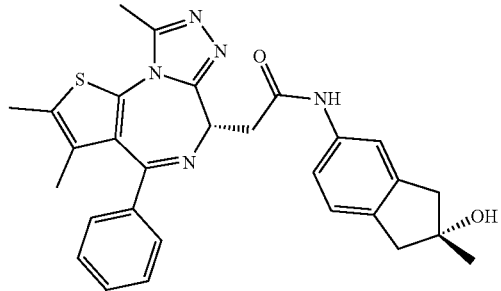

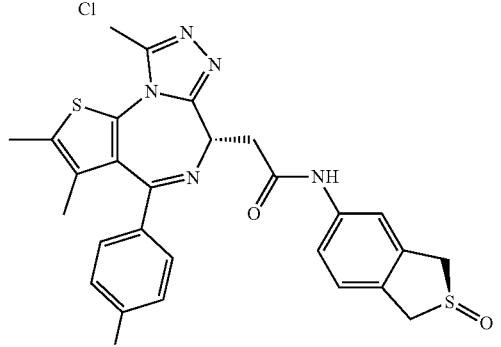

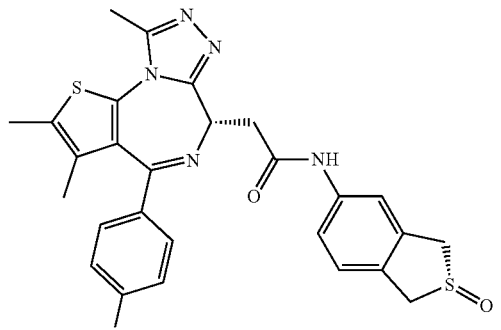

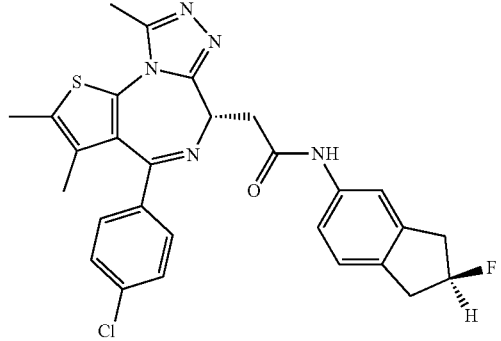

143
-continued
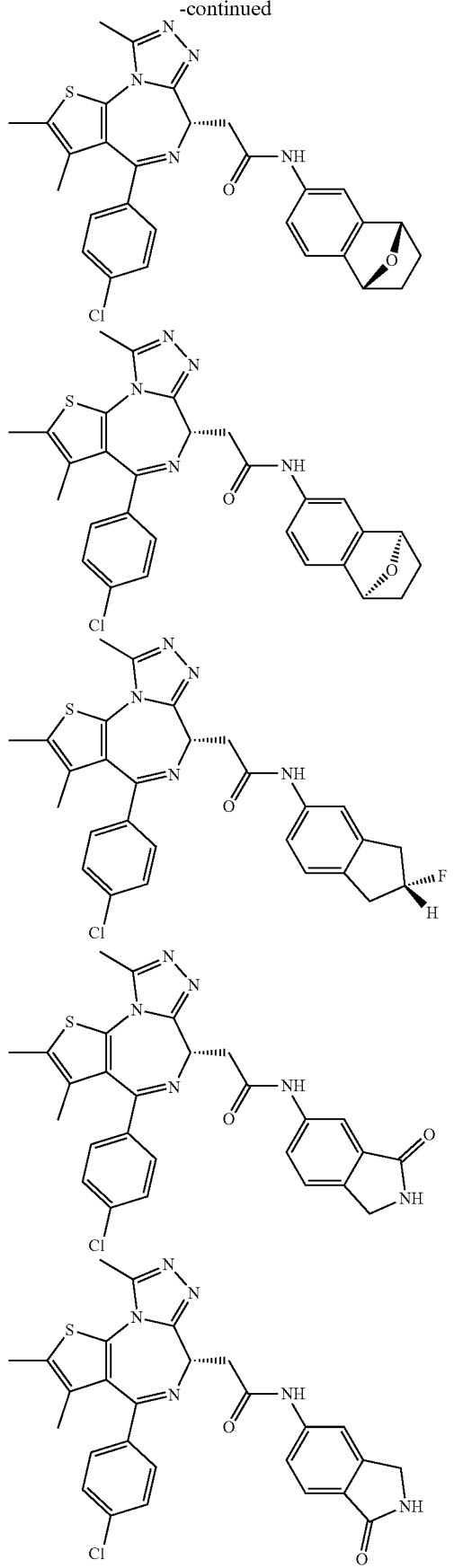
144
-continued
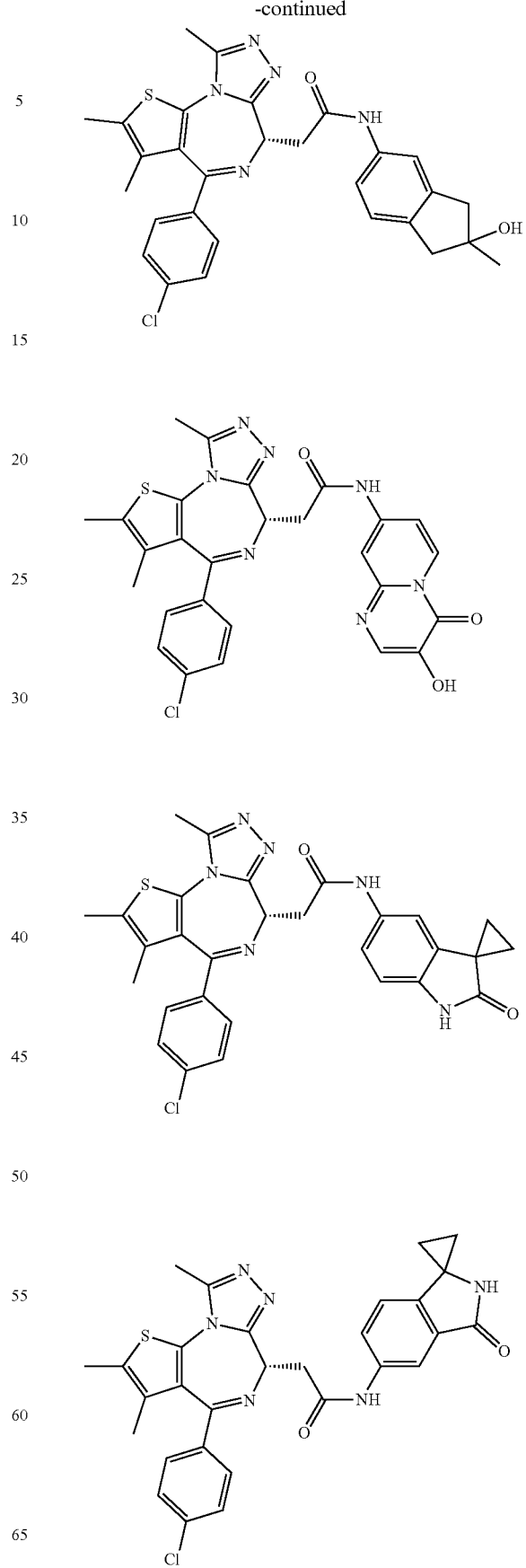

145
-continued
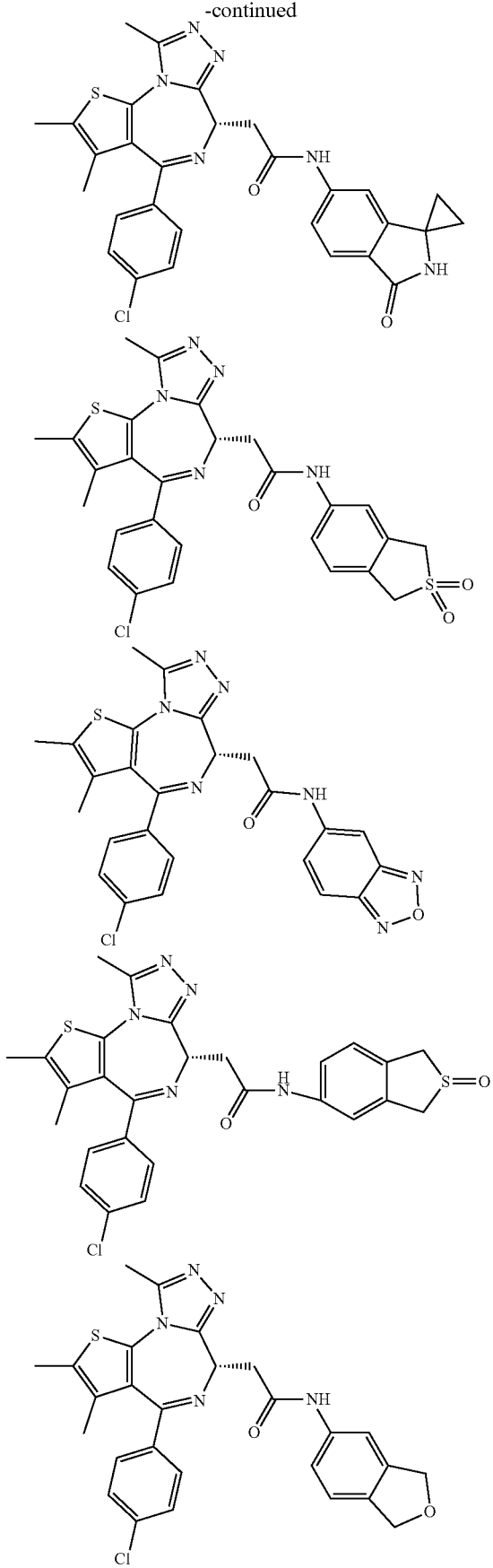
146
-continued
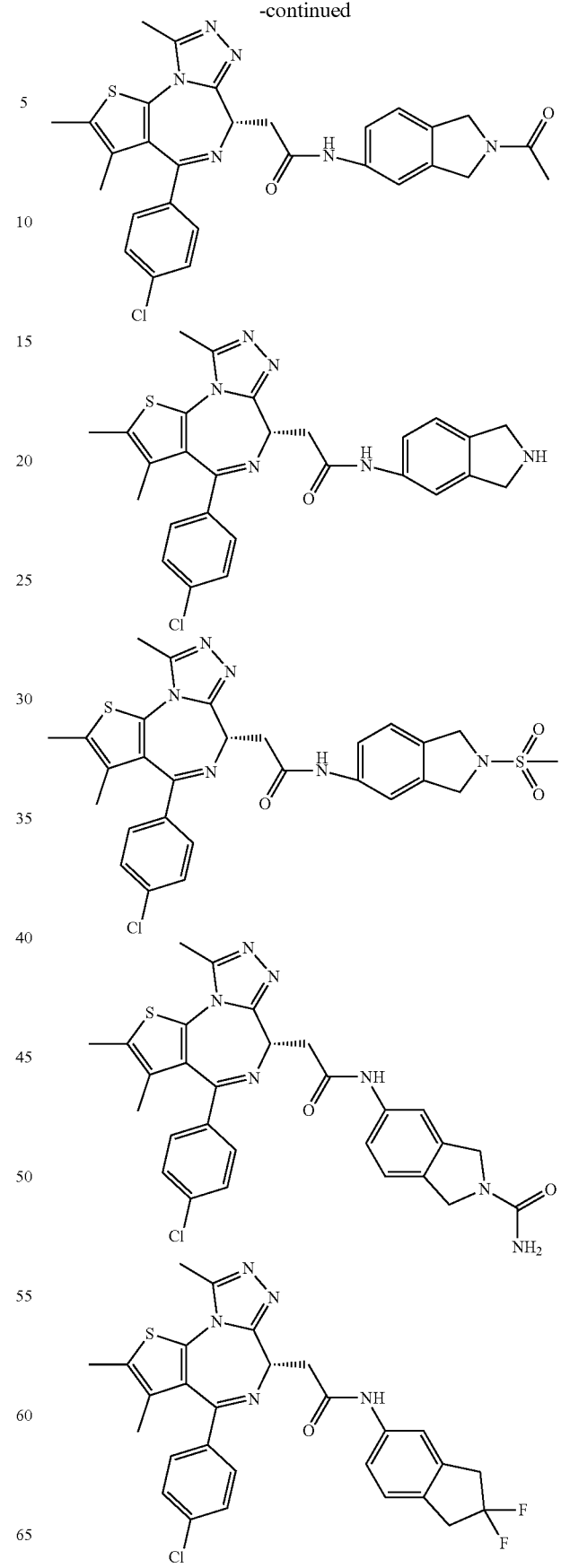

147
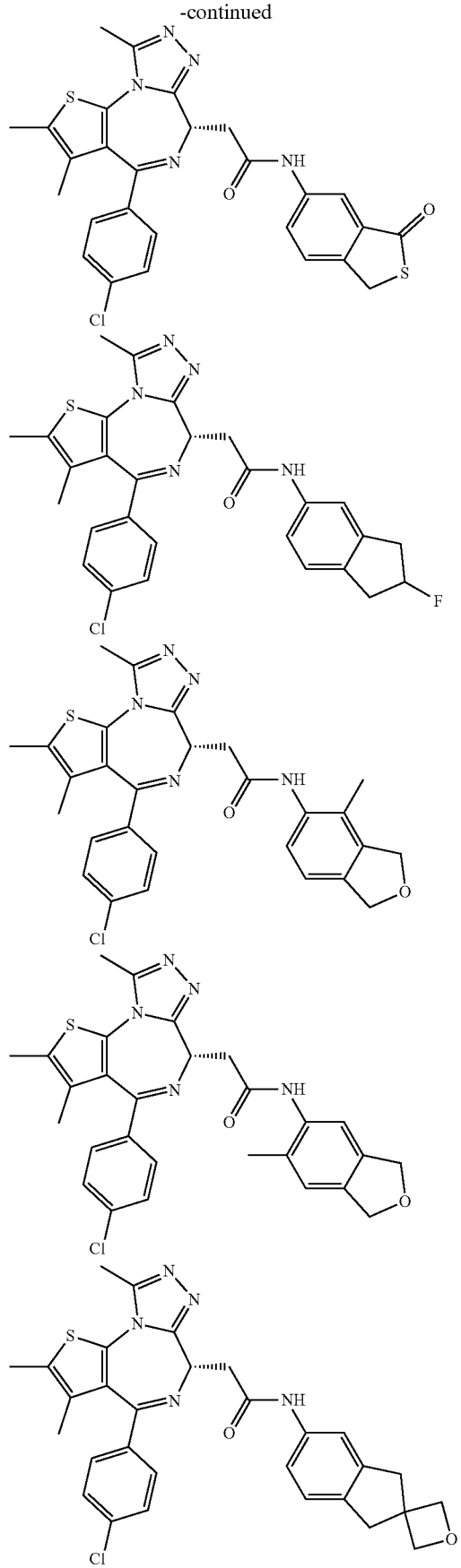
148
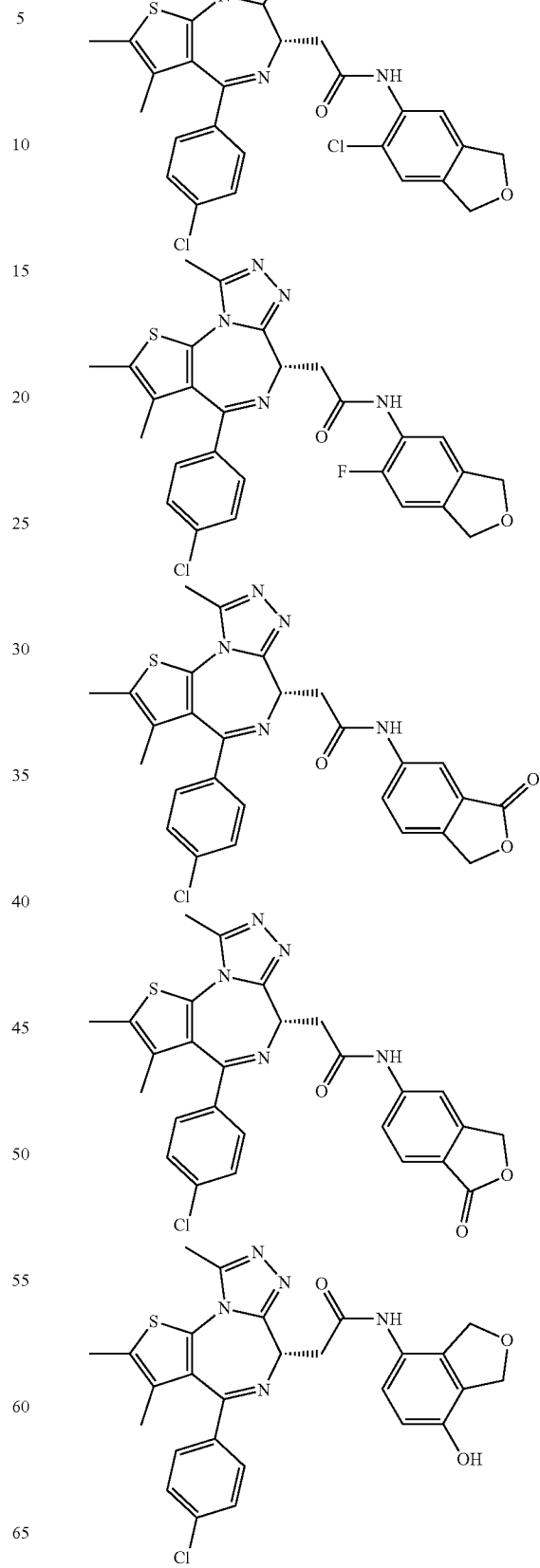

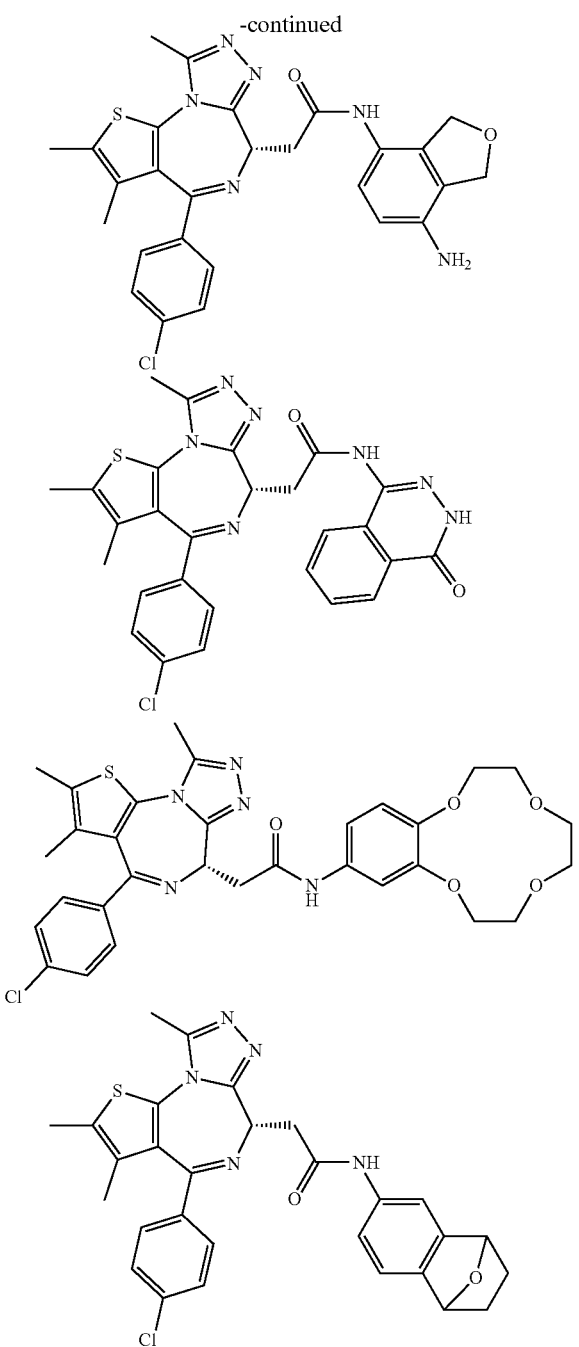
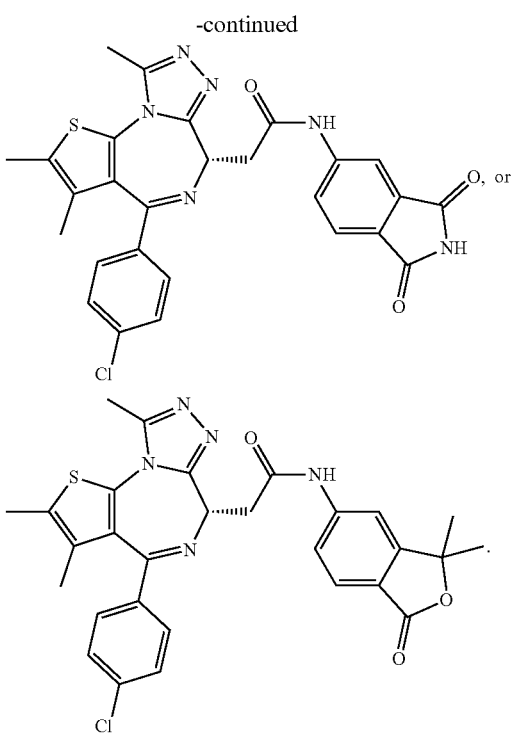

18. A pharmaceutical composition, comprising a therapeutically effective amount of the compound, geometric isomer, stereoisomer, tautomer, or pharmaceutically acceptable salt of claim 1 as an active ingredient and a pharmaceutically acceptable carrier.

19. A method of treating a disease, wherein the disease comprises breast cancer, triple negative breast cancer, colon cancer, rectal cancer, colorectal cancer or prostatic cancer, the method comprising administering a therapeutically effective amount of the compound, geometric isomer, stereoisomer, tautomer, or pharmaceutically acceptable salt of claim 1 to a subject in need thereof.

20. The method of claim 19, wherein the disease is a bromodomain extra-terminal (BET) protein-related disease.

21. A method of inhibiting BET bromodomain protein activity, comprising administering an effective amount of the compound, geometric isomer, stereoisomer, tautomer, or pharmaceutically acceptable salt of claim 1 to a subject in need thereof.

* * * * *